(12) United States Patent
Hsu et al.

(10) Patent No.: US 7,776,527 B2
(45) Date of Patent: Aug. 17, 2010

(54) METHODS AND COMPOSITIONS FOR REDUCING MICROBIAL INDUCED APOPTOSIS

(75) Inventors: Li-Chung Hsu, San Diego, CA (US); Michael Karin, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 478 days.

(21) Appl. No.: 10/578,976

(22) PCT Filed: Nov. 12, 2004

(86) PCT No.: PCT/US2004/038032
§ 371 (c)(1), (2), (4) Date: Apr. 23, 2007

(87) PCT Pub. No.: WO2005/046617
PCT Pub. Date: May 26, 2005

(65) Prior Publication Data
US 2007/0281328 A1    Dec. 6, 2007

Related U.S. Application Data

(60) Provisional application No. 60/519,485, filed on Nov. 12, 2003.

(51) Int. Cl.
*C12Q 1/18* (2006.01)
*C12Q 1/48* (2006.01)
*C12Q 1/68* (2006.01)

(52) U.S. Cl. .............. 435/6; 435/15; 435/32; 435/325; 435/375

(58) Field of Classification Search ............. None
See application file for complete search history.

(56) References Cited

OTHER PUBLICATIONS

Langland and Bertram. The role of the PKR-inhibitory genes, E3L and K3L, in determining vaccinia virus host range. Virology. 2002; 299(1): 133-41.*

Carlson, et al. Selection of small-molecule mediators of the RNA regulation of PKR, the RNA-dependent protein kinase. Chembiochem. 2002; 3(9):859-65.*

Sone T. Development of Fasudil Hydrochloride (ERIL(R))—A New-Protein Kinase Inhibitor.J SYN ORG CHEM. 1996; 54(9):794-800. Abstract Only.*

Waring, P. DNA Fragmentation Induced in Macrophages by Gliotoxin Does Not Require Protein Synthesis and Is Preceded by Raised Inositol Triphosphate Levels. J. Biol. Chem. 1990; vol. 265, No. 24, Issue of Aug. 25, pp. 14476-14480.*

Jesenberger, et al. Salmonella-induced Caspase-2 Activation in Macrophages: A Novel Mechanism in Pathogen-mediated Apoptosis. J. Exp. Med. 2000;192;(7):1035-1045.*

Liu, et al. Induction of Caspase-Dependent Apoptosis in Cultured Cells by the Avian Coronavirus Infectious Bronchitis Virus. J Virol. 2001; 75(14):6402-6409.*

* cited by examiner

*Primary Examiner*—Mary E Mosher
*Assistant Examiner*—Stuart W Snyder
(74) *Attorney, Agent, or Firm*—Medlen & Carroll, LLP

(57) ABSTRACT

The present invention relates to microbial infection, and in particular, the reduction of apoptosis associated with microbial infection, the screening of agents that reduce apoptosis, and the treatment and analysis of microbial infection in vivo. In one embodiment, the present invention relates to agents including but not limited to reducing the activity of Protein Kinase R.

2 Claims, 23 Drawing Sheets

SEQ ID No:01
Homo sapiens protein kinase, interferon-inducible double
stranded RNA dependent (PRKR), MAGDLSAGFFMEELNTYRQKQGVVLKYQELPNSGPPHDRRFTFQVIIDGREFPEGEGRS
KKEAKNAAAKLAVEILNKEKKAVSPLLLTTTNSSEGLSMGNYIGLINRIAQKKRLTVNY
EQCASGVHGPEGFHYKCKMGQKEYSIGTGSTKQEAKQLAAKLAYLQILSEETSVKSDYL
SSGSFATTCESQSNSLVTSTLASESSSEGDFSADTSEINSNSDSLNSSSLLMNGLRNNQ
RKAKRSLAPRFDLPDMKETKYTVDKRFGMDFKEIELIGSGGFGQVFKAKHRIDGKTYVI
KRVKYNNEKAEREVKALAKLDHVNIVHYNGCWDGFDYDPETSDDSLESSDYDPENSKNS
SRSKTKCLFIQMEFCDKGTLEQWIEKRRGEKLDKVLALELFEQITKGVDYIHSKKLIHR
DLKPSNIFLVDTKQVKIGDFGLVTSLKNDGKRTRSKGTLRYMSPEQISSQDYGKEVDLY
ALGLILAELLHVCDTAFETSKFFTDLRDGIISDIFDKKEKTLLQKLLSKKPEDRPNTSE
ILRTLTVWKKSPEKNERHTC SEQ ID No:02
Homo sapiens protein kinase, interferon-inducible double
stranded RNA dependent (PRKR),
GCGGCGGCGGCGGCGCAGTTTGCTCATACTTTGTGACTTGCGGTCACAGTGGCATTCAG
CTCCACACTTGGTAGAACCACAGGCACGACAAGCATAGAAACATCCTAAACAATCTTCA
TCGAGGCATCGAGGTCCATCCCAATAAAAATCAGGAGACCCTGGCTATCATAGACCTTA
GTCTTCGCTGGTATACTCGCTGTCTGTCAACCAGCGGTTGACTTTTTTAAGCCTTCTT
TTTTCTCTTTTACCAGTTTCTGGAGCAAATTCAGTTTGCCTTCCTGGATTTGTAAATTG
TAATGACCTCAAAACTTTAGCAGTTCTTCCATCTGACTCAGGTTTGCTTCTCTGGCGGT
CTTCAGAATCAACATCCACACTTCCGTGATTATCTGCGTGCATTTTGGACAAAGCTTCC
AACCAGGATACGGGAAGAAGAAATGGCTGGTGATCTTTCAGCAGGTTTCTTCATGGAGG
AACTTAATACATACCGTCAGAAGCAGGGAGTAGTACTTAAATATCAAGAACTGCCTAAT
TCAGGACCTCCACATGATAGGAGGTTTACATTTCAAGTTATAATAGATGGAAGAGAATT
TCCAGAAGGTGAAGGTAGATCAAAGAAGGAAGCAAAAAATGCCGCAGCCAAATTAGCTG
TTGAGATACTTAATAAGGAAAAGAAGGCAGTTAGTCCTTTATTATTGACAACAACGAAT
TCTTCAGAAGGATTATCCATGGGGAATTACATAGGCCTTATCAATAGAATTGCCCAGAA
GAAAAGACTAACTGTAAATTATGAACAGTGTGCATCGGGGGTGCATGGGCCAGAAGGAT
TTCATTATAAATGCAAAATGGGACAGAAAGAATATAGTATTGGTACAGGTTCTACTAAA
CAGGAAGCAAAACAATTGGCCGCTAAACTTGCATATCTTCAGATATTATCAGAAGAAAC
CTCAGTGAAATCTGACTACCTGTCCTCTGGTTCTTTTGCTACTACGTGTGAGTCCCAAA
GCAACTCTTTAGTGACCAGCACACTCGCTTCTGAATCATCATCTGAAGGTGACTTCTCA
GCAGATACATCAGAGATAAATTCTAACAGTGACAGTTTAAACAGTTCTTCGTTGCTTAT
GAATGGTCTCAGAAATAATCAAAGGAAGGCAAAAGATCTTTGGCACCCAGATTTGACC
TTCCTGACATGAAAGAAACAAAGTATACTGTGGACAAGAGGTTTGGCATGGATTTTAAA
GAAATAGAATTAATTGGCTCAGGTGGATTTGGCCAAGTTTTCAAAGCAAAACACAGAAT
TGACGGAAAGACTTACGTTATTAAACGTGTTAAATATAATAACGAGAAGGCGGAGCGTG
AAGTAAAAGCATTGGCAAAACTTGATCATGTAAATATTGTTCACTACAATGGCTGTTGG
GATGGATTTGATTATGATCCTGAGACCAGTGATGATTCTCTTGAGAGCAGTGATTATGA
TCCTGAGAACAGCAAAAATAGTTCAAGGTCAAAGACTAAGTGCCTTTTCATCCAAATGG
AATTCTGTGATAAAGGGACCTTGGAACAATGGATTGAAAAAAGAAGAGGCGAGAAACTA

Fig. 21 continued

```
GACAAAGTTTTGGCTTTGGAACTCTTTGAACAAATAACAAAAGGGGTGGATTATATACA
TTCAAAAAATTAATTCATAGAGATCTTAAGCCAAGTAATATATTCTTAGTAGATACAA
AACAAGTAAAGATTGGAGACTTTGGACTTGTAACATCTCTGAAAAATGATGGAAAGCGA
ACAAGGAGTAAGGGAACTTTGCGATACATGAGCCCAGAACAGATTTCTTCGCAAGACTA
TGGAAAGGAAGTGGACCTCTACGCTTTGGGGCTAATTCTTGCTGAACTTCTTCATGTAT
GTGACACTGCTTTTGAAACATCAAAGTTTTTCACAGACCTACGGGATGGCATCATCTCA
GATATATTTGATAAAAAAGAAAAAACTCTTCTACAGAAATTACTCTCAAAGAAACCTGA
GGATCGACCTAACACATCTGAAATACTAAGGACCTTGACTGTGTGGAAGAAAAGCCCAG
AGAAAAATGAACGACACACATGTTAGAGCCCTTCTGAAAAAGTATCCTGCTTCTGATAT
GCAGTTTTCCTTAAATTATCTAAAATCTGCTAGGGAATATCAATAGATATTTACCTTTT
ATTTTAATGTTTCCTTTAATTTTTTACTATTTTTACTAATCTTTCTGCAGAAACAGAAA
GGTTTTCTTCTTTTTGCTTCAAAAACATTCTTACATTTTACTTTTTCCTGGCTCATCTC
TTTATTCTTTTTTTTTTTTTTAAAGACAGAGTCTCGCTCTGTTGCCCAGGCTGGAGTGC
AATGACACAGTCTTGGCTCACTGCAACTTCTGCCTCTTGGGTTCAAGTGATTCTCCTGC
CTCAGCCTCCTGAGTAGCTGGATTACAGGCATGTGCCACCCACCCAACTAATTTTTGTG
TTTTTAATAAAGACAGGGTTTCACCATGTTGGCCAGGCTGGTCTCAAACTCCTGACCTC
AAGTAATCCACCTGCCTCGGCCTCCCAAAGTGCTGGGATTACAGGGATGAGCCACCGCG
CCCAGCCTCATCTCTTTGTTCTAAAGATGGAAAAACCACCCCCAAATTTTCTTTTTATA
CTATTAATGAATCAATCAATTCATATCTATTTATTAAATTTCTACCGCTTTTAGGCCAA
AAAAATGTAAGATCGTTCTCTGCCTCACATAGCTTACAAGCCAGCTGGAGAAATATGGT
ACTCATTAAAAAAAAAAAAAAAAGTGATGTACAACC
```

```
SEQ ID No:03
Mus musculus protein kinase, interferon-inducible double
stranded RNA dependent,
MASDTPGFYMDKLNKYRQMHGVAITYKELSTSGPPHDRRFTFQVLIDEKEFPEAKGKSK
QEARNAAAKLAVDILDNENKVDCHTSASEQGLPYGNYIGLVNSFAQKKKLSVNYEQCEP
NSELPQRFICKCKIGQTMYGTGSGVTKQEAKQLAAKEAYQKLLKSPPKTAGTSSSVVTS
TFSGFSSSSSMTSNGVSQSAPGSPSSENVFTNGLGENKRKSGVKVSPDDVQRNKYTLDA
RFNSDFEDIEEIGLGGFGQVFKAKHRIDGKRYAIKRVKYNTEKAEHEVQALAELNHVNI
VQYHSCWEGVDYDPEHSMSDTSRYKTRCLFIQMEFCDKGTLEQWMRNRNQSKVDKALIL
DLYEQIVTGVEYIHSKGLIHRDLKPGNIFLVDERHIKIGDFGLATALENDGKSRTRRTG
TLQYMSPEQLFLKHYGKEVDIFALGLILAELLHTCFTESEKIKFFESLRKGDFSNDIFD
NKEKSLLKKLLSEKPKDRPETSEILKTLAEWRNISEKKKRNTC
```

```
SEQ ID No:04
Mus musculus protein kinase, interferon-inducible double
stranded RNA dependent,
ACCGGCCAGGCCCGGACTTCCATGGGCAGCAGCAGCGGCAGGGAACGGAGGGCGAATAG
ATTTCAGAGCCTGCACCTGAAGTACAATTCGAATCCTGCTCCAGGGAGCGAGCCACTGT
CCGGATCCAGAAACTTTGGCCACTGGGAGGAAAAATGGCCAGTGATACCCCAGGTTTCT
ACATGGACAAACTTAATAAATACCGCCAGATGCACGGAGTAGCCATTACGTATAAAGAA
CTTAGTACTTCGGGACCTCCACATGACAGAAGGTTTACATTTCAAGTTTTAATAGATGA
GAAGGAATTTCCAGAAGCCAAAGGTAAATCAAAGCAGGAGGCAAGAAACGCTGCAGCCA
AATTAGCTGTTGATATACTTGATAACGAAAACAAGGTGGATTGTCACACGAGTGCATCT
GAGCAAGGCTTGCCCTATGGTAACTACATAGGCCTTGTCAATAGCTTTGCCCAGAAGAA
```

Fig. 21 continued

```
AAAGCTGTCTGTAAATTATGAACAGTGTGAGCCCAACTCTGAGTTGCCTCAAAGATTTA
TTTGTAAATGCAAAATTGGGCAGACGATGTATGGTACTGGTTCAGGTGTCACCAAACAG
GAGGCAAAGCAGTTGGCTGCGAAAGAAGCCTATCAGAAGCTGTTAAAGAGCCCGCCGAA
AACTGCCGGAACATCCTCTAGCGTTGTCACATCTACATTCAGTGGCTTTTCCAGCAGCT
CGTCTATGACAAGTAATGGTGTTTCCCAGTCAGCACCTGGAAGTTTTTCCTCAGAGAAC
GTGTTTACGAACGGTCTCGGAGAAAATAAAAGGAAATCAGGAGTAAAAGTATCCCCTGA
TGATGTGCAAAGAAATAAATATACCTTGGACGCCAGGTTTAACAGCGATTTTGAAGACA
TAGAAGAAATTGGCTTAGGTGGATTTGGTCAAGTTTTCAAAGCGAAACACAGAATTGAT
GGAAAGAGATACGCTATTAAGCGCGTTAAATATAACACGGAGAAGGCGGAGCACGAAGT
ACAAGCGCTGGCAGAACTCAATCACGTCAACATTGTCCAATACCATAGTTGTTGGGAGG
GAGTTGACTATGATCCTGAGCACAGCATGAGTGATACAAGTCGATACAAAACCCGGTGC
CTCTTTATTCAAATGGAATTCTGTGATAAAGGAACTTTGGAGCAATGGATGAGAAACAG
AAATCAGAGTAAAGTGGACAAAGCTTTGATTTTGGACTTATATGAACAAATCGTGACCG
GAGTGGAGTATATACACTCGAAAGGGTTAATTCACAGAGATCTTAAGCCAGGTAATATA
TTTTTAGTAGATGAAAGACACATTAAGATCGGAGACTTTGGCCTTGCAACAGCCCTGGA
AAATGATGGAAAATCCCGAACAAGGAGAACAGGAACTCTTCAATATATGAGTCCAGAAC
AGTTATTTTTAAAGCACTATGGAAAAGAAGTGGACATCTTTGCTTTGGGCCTTATTCTA
GCTGAACTTCTTCACACGTGCTTCACGGAGTCAGAGAAAATAAAGTTTTTCGAAAGTCT
AAGAAAAGGCGACTTCTCTAATGATATATTCGACAACAAAGAAAAAAGCCTTCTAAAAA
AACTACTCTCAGAGAAACCCAAGGACCGACCTGAGACATCTGAAATCCTGAAGACCTTG
GCTGAATGGAGGAACATCTCAGAGAAAAGAAAAGAAACACATGTTAGGGCCTTTCTGA
GAAAACATTCCTCTGCCGTGGTTTTCCTTTAACGATCTGCAGTCTGAGGGGAGTATCAG
TGAATATTATCCTTCTTTTCTTAATACCACTCTCCCAGACAGGTTTTGGTTAGGGTGAC
CCACAGACATTGTATTTATTAGGCTATGAAAAGTATGCCCATTTCCTCAATTGTTAAT
TGCTGGGCCTGTGGCTGGCTAGCTAGCCAAATATGTAAATGCTTGTTTCTCGTCTGCCC
AAAGAGAAAGGCAGGCTCCTGTGTGGGAAGTCACAGAGCCCCCAAAGCCAACTGGATGA
GGAAGGACTCTGGCTTTTGGCATAAAAAAGAGCTGGTAGTCAGAGCTGGGGCAGAAGGT
CCTGCAGACAGACAGACAGACAGACAGACAGAGACACAAAGACATGGACTAGAAT
GGAGGAGGGAGGGAGGAAGGGAGGGAGGGAGAGAGAGAGAGAGAAAGAAAGAGAGAG
ACCACATGGAGAGACAAAATGGCTTAAGTTAGCTGGGCTAACTGAGAGACTGTCCAGA
AAACAGGCCAACAACCTTCCTTATGCTATATAGATGTCTCAGTGTCTTTATCATTAAAC
ACCAAGCAGGACTGCTAAAAACTCTGCAATAGGGTTTTTTTTTCCTGTTACTTCAAAAG
CAAAAAAAAAAAAAAAAAAA
```

METHODS AND COMPOSITIONS FOR REDUCING MICROBIAL INDUCED APOPTOSIS

This application is a U.S. national entry of International Application No. PCT/US2004/038032, filed on Nov. 12, 2004, which claims benefit of U.S. Provisional Application Ser. No. 60/519,485, filed Nov. 12, 2003, the contents of which are incorporated herein in their entirety.

This invention was made, in part, with government support under grant number 5R21-AI53528-02 awarded by the National Institutes of Health. The U.S. government has certain rights in the invention.

FIELD OF THE INVENTION

The present invention relates to microbial infection, and in particular, the reduction of apoptosis associated with microbial infection, the screening of agents that reduce apoptosis, and the treatment and analysis of microbial infection in vivo. In one embodiment, the present invention relates to agents including but not limited to reducing the activity of Protein Kinase R and/or Toll-like receptor-4.

BACKGROUND

Current treatments for bacterial infections rely upon antibiotics. However widely spread published reports indicate that although antibiotics were initially miracle cures, they are now increasingly ineffective due to the emergence of new bacteria strains including many resistant "superbugs." Compounding the superbug phenomena is the observation that as quickly as new antibiotics are used, the pathogenic bacteria populations shift towards refractory strains. Furthermore, antibiotics are minimally if not contra-indicated in patients with co-existing viral infections. Antibiotic treatment in such patients, while potentially effective against the bacteria, may potentiate the viral infection.

Thus, there is a need to find new ways to identify drugs that will reduce bacteria infections, and in particular bacteria infections within patients with viral infections.

SUMMARY OF THE INVENTION

The present invention relates to microbial infection, and in particular, the reduction of apoptosis associated with microbial infection, the screening of agents that reduce apoptosis, and the treatment and analysis of microbial infection in vivo. In one embodiment, the present invention relates to agents including but not limited to reducing the activity of Protein Kinase R and/or Toll-like receptor-4.

In one embodiment, the present invention contemplates methods for identifying agents for reducing apoptosis of macrophage cells, particularly bacterial induced apoptosis mediated by Protein Kinase R and/or Toll-like receptor-4. Such methods serve to distinguish agents that would be drug candidates as anti-microbials. Certain embodiments of the method are designed to assess the apoptosis reduction potential of agents by virtue of their in vitro ability to reduce proteins associated with apoptosis, apoptotic pathways and apoptotic death.

In one embodiment, the invention provides a method for identifying a test agent as reducing apoptosis of macrophage cells, comprising: (a) providing: (i) macrophage cells; and (ii) test agent; (b) contacting said macrophage cells in the presence of said test agent to produce contacted macrophage cells and in the absence of said test agent to produce control cells; and (c) detecting reduced activity of Protein Kinase R in said contacted cells compared to Protein Kinase R in said control cells, wherein said detecting identifies said test agent as reducing apoptosis of macrophage cells. In another embodiment, the invention provides a method for identifying a test agent as reducing apoptosis of macrophage cells, further comprising the step of (d) identifying said test agent as anti-bacterial.

In one embodiment, the invention provides a method for identifying a test agent as reducing apoptosis of macrophage cells, comprising: (a) providing: (i) macrophage cells; and (ii) test agent; (b) contacting said macrophage cells in the presence of said test agent to produce contacted macrophage cells and in the absence of said test agent to produce control cells; and (c) detecting reduced activity of Toll-like Receptor-4 in said contacted cells compared to Toll-like Receptor-4 in said control cells, wherein said detecting identifies said test agent as reducing apoptosis of macrophage cells. In another embodiment, the invention provides a method for identifying a test agent as reducing apoptosis of macrophage cells, further comprising the step of (d) identifying said test agent as anti-bacterial.

In one embodiment, the invention provides a method for reducing apoptosis of macrophage cells, comprising reducing the activity of a Protein Kinase R.

In one embodiment, the invention provides a method for reducing apoptosis of macrophage cells, comprising reducing the activity of a Toll-like Receptor-4.

In one embodiment, the invention provides a method for reducing apoptosis of macrophage cells, comprising: (a) providing: (i) macrophage cells; and (ii) agent that reduces activity of Protein Kinase R; and (b) contacting said macrophage cells with said agent and without said agent under conditions such that said agent reduces activity of said Protein Kinase R. In another embodiment, the invention provides a method for reducing apoptosis of macrophage cells, wherein said macrophage cells are contacted with a bacterium. The present invention is not limited to any particular type of bacterium. Indeed, a variety of bacterium are contemplated, including, but not limited to gram-negative bacterium, gram-positive bacterium and pathogenic bacterium. Indeed, a variety of bacterium are contemplated, including, but not limited to *Bacillus* species, *Yersinia* species, *Salmonella* species, *Shigella* species, *Streptococcus* species and *Haemophilus* species. In a further embodiment, the invention provides a method for reducing apoptosis of macrophage cells, wherein said bacterium is gram-negative. In yet another further embodiment, the invention provides a method for reducing apoptosis of macrophage cells, wherein said bacterium is gram-positive. In another embodiment, the invention provides a method for reducing apoptosis of macrophage cells, wherein said macrophage cells are contacted with a molecule chosen from one or more of lipopolysaccharide, lipoteichoiec acid, *Yersinia pseudotuberculosis* YopJ protein, and protein expressed by the *Salmonella typhimurium* SP12 locus. In another embodiment, the invention provides a method for reducing apoptosis of macrophage cells, wherein said macrophage cells are contacted with one or more of a dsRNA and a virus prior to contacting with a molecule chosen from one or more of lipopolysaccharide, lipoteichoiec acid, *Yersinia pseudotuberculosis* YopJ protein, and protein expressed by the *Salmonella typhimurium* SP12 locus. In a further embodiment, the invention provides a method for reducing apoptosis of macrophage cells, wherein said macrophage cells are contacted with one or more of a dsRNA and a virus prior to contacting with a bacterium. In an additional embodiment, said virus comprises Influenzavirus.

In one embodiment, the invention provides a method for reducing apoptosis of macrophage cells, comprising: (a) providing: (i) macrophage cells; and (ii) agent that reduces activity of Toll-Like Receptor-4; and (b) contacting said macrophage cells with said agent and without said agent under conditions such that said agent reduces activity of said Toll-Like Receptor-4.

In one embodiment, the invention provides a method of treating or analyzing a microbial infection in a cell, comprising: a) providing: i) a cell with one or more symptoms of a microbial infection and ii) a formulation comprising a Protein Kinase R inhibitor; and b) exposing said formulation to said cell under conditions such that said one or more symptoms of a microbial infection are reduced. In another embodiment, the cell has a microbial infection associated with one or more symptoms of a viral infection. In another embodiment, the microbe is a bacterium. In a further embodiment, the bacterium is selected from a group comprising *Bacillus* species, *Yersinia* species, *Salmonella* species, *Shigella* species, *Streptococcus* species and *Haemophilus* species. In a further embodiment, the virus is selected from a group comprising Influenzavirus A, Influenzavirus B, and Influenzavirus C. In another embodiment, the infection is a multiple infection. In a further embodiment, the multiple infection comprises a bacteria infection and a virus infection. In yet a further embodiment, the virus is selected from a group comprising Influenzavirus A, Influenzavirus B, and Influenzavirus C. In another embodiment, the cell is in a tissue or a patient. In a further embodiment, the patient is an animal (e.g., a human). In another embodiment, the patient has a microbial infection associated with one or more symptoms of a pathogen infection.

In one embodiment, the invention provides a method of treating a microbial infection in a patient, comprising: a) providing: i) a patient with one or more symptoms of a microbial infection and ii) a formulation comprising a Protein Kinase R inhibitor; and b) administering said formulation to said patient under conditions such that said one or more symptoms of a microbial infection are reduced. In another embodiment, the patient has a microbial infection associated with one or more symptoms of a viral infection. In another embodiment, the infection is a bacterial infection. In yet a further embodiment, the bacterium is selected from a group comprising *Bacillus* species, *Yersinia* species, *Salmonella* species, *Shigella* species, *Streptococcus* species and *Haemophilus* species. In another embodiment, the virus is selected from a group comprising Influenzavirus A, Influenzavirus B, and Influenzavirus C. In another embodiment, the infection is a multiple infection. In a further embodiment, the multiple infection comprises a bacteria infection and a virus infection. In yet a further embodiment, the virus is selected from a group comprising Influenzavirus A, Influenzavirus B, and Influenzavirus C.

BRIEF DESCRIPTION OF THE DRAWINGS

FIG. 11 shows an exemplary embodiment in which *B. anthracis* induced macrophage apoptosis is TLR4-dependent.

FIG. 21 shows the polypeptide and nucleotides sequences of the protein kinase; interferon-inducible double stranded RNA dependent PKR (PRKR), GenBank Accession No. human: NM_002759 (SEQ ID NOs: 1 and 2), mouse: BC016422 (SEQ ID NOs: 3 and 4).

DEFINITIONS

Figure 1:
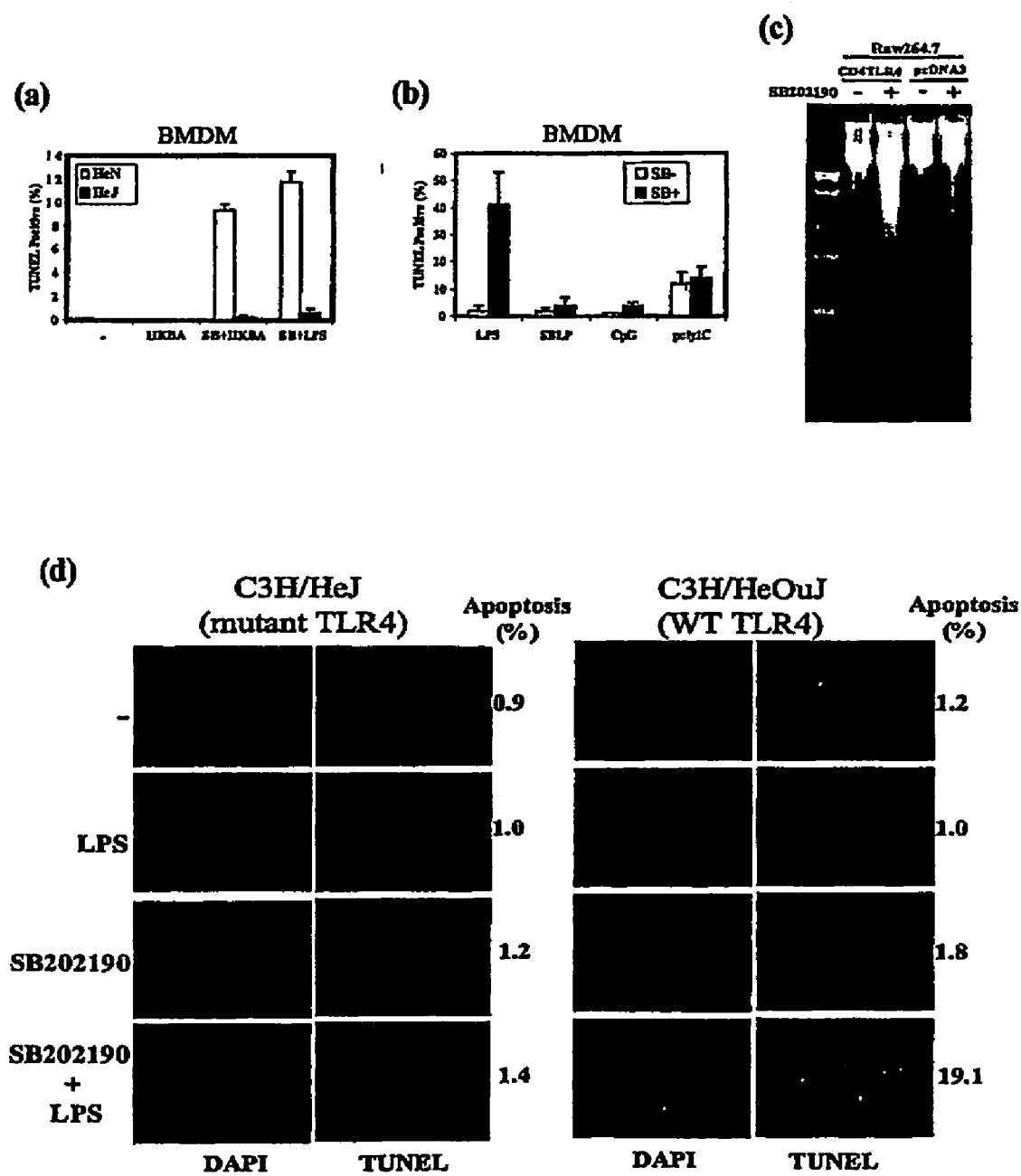
FIG. 1 shows exemplary embodiments in which heat killed *B. anthracis* and LPS induce macrophage apoptosis through TLR4.

To facilitate understanding of the invention, a number of terms are defined below.

As used herein including within this specification and the appended claims, the forms "a," "an" and "the" includes both singular and plural references unless the content clearly dictates otherwise.

As used herein, the term "or" when used in the expression "A or B," and where A and B refer to a composition, disease, product, etc., means one, or the other, or both.

As used herein, the terms "microorganism" and "microbe" refer to any organism of microscopic or ultramicroscopic size including, but not limited to, viruses, bacteria, fungi and protozoa.

Viruses are exemplified by, but not limited to, Arenaviridae, Baculoviridae, Birnaviridae, Bunyaviridae, Cardioviius, Corticoviridae, Cystoviridae, Epstein-Barr virus, Filoviridae, Hepadnviridae, Hepatitis virus, Herpesviridae, Influenza virus, Inoviridae, Iridoviridae, Metapneumovirus, Orthomyxoviridae, Papovavirus, Paramyxoviridae, Parvoviridae, Polydnaviridae, Poxyviridae, Reoviridae, Rhabdoviridae, Semliki Forest virus, Tetraviridae, Toroviridae, Vaccinia virus, Vesicular stomatitis virus, togaviruses, flaviviruses, coronaviruses, and picornaviruses (including Adenovirus, Enterovirus, Immunodeficiency virus, Poliovirus, and Retrovirus).

The term "bacteria" and "bacterium" refer to all prokaryotic organisms, including those within all of the phyla in the Kingdom Procaryotae. It is intended that the term encompass all microorganisms considered to be bacteria including but not limited to, *Mycoplasma* species, *Chlamydia* species, *Actinomyces* species, *Streptomyces* species, *Rickettsia* species, Enterobacteriaceae species, and *Enterococcus* species. All forms of bacteria are included within this definition including cocci, bacilli, spirochetes, spheroplasts, protoplasts, etc. and are exemplified by *Escherichia Coli, Haemophilus influenza, Mycobacterium tuberculosis, Neisseria gonorrhoeae, Pseudomonas aeruginosa, Shigella dysenteriae, Staphylococcus aureus*, and *Streptococcus pneumonia*. Also included within these terms are prokaryotic organisms that are gram negative or gram positive. "Gram-negative" and "gram-positive" refer to staining patterns with the Gram-staining process that is well known in the art (Finegold and Martin, Diagnostic Microbiology, 6th Ed. (1982), CV Mosby St. Louis, pp 13-15). "Gram-positive bacteria" are bacteria that retain the primary dye used in the Gram stain, causing the stained cells to appear dark blue to purple under the microscope. Exemplary gram-positive bacteria include *Staphylococcus aureus, Staphylococcus hemolyticus*, and *Streptococcus pneumoniae*. "Gram-negative bacteria" do not retain the primary dye used in the Gram stain, but are stained by the counterstain. Thus, gram-negative bacteria appear red. Exemplary gram-negative bacteria include *Escherichia coli, Klebsiella pneumoniae, Pseudomonas aeruginosa, Haemophilus influenzae*, and *Neisseriae gonorrhoeae*.

As used herein, the term "pathogen" refers to any microbe that is associated with infection, inflammation and disease. It is not meant to limit the pathogen to those traditionally considered bacterial pathogens (e.g., *B. anthracis, Y. pseudotuberculosis, S. typhimurium, K. pneumoniae, H. Influenza, S. aureus, S. pyogenes, S. dysenteriae, S. flexneri* etc.) or opportunistic bacterial pathogens (e.g., *P. aeruginosa, S. marcesens, S. mitis*, etc.) or a viral pathogen (Influenzavirus).

The terms "fungi" and "yeast" are used interchangeably herein and refer to the art recognized group of eukaryotic protists known as fungi. "Yeast" as used herein can encompass the two basic morphologic forms of yeast and mold and dimorphisms thereof. Exemplary fungal species include *Aspergillus* species (such as *Aspergillus fumigatus, Aspergillus flavus, Aspergillus niger, Aspergillus nidulans*, and *Aspergillus terreus*), *Blastomyces* species, *Candida* species (such as *Candida albicans, Candida stellatoidea, Candida glabrata, Candida tropicalis, Candida parapsilosis, Candida krusei, Candida pseudotropicalis, Candida guilliermondii*, and *Candida rugosa*), *Coccidioides* species, *Cryptococcus* species, *Epidermophyton* species, *Hendersonula* species, *Histoplasma* species, *Microsporum*, species, *Paecilomyces* species, *Paracoccidioides* species, *Pneumocystis* species such as *Pneumocystis carinii, Trichophyton* species, and *Trichosporium* species. Exemplary fungi include *Pneumocystis carinii, Cryptococcus neoformans, Histoplasma capsulatum, Coccidioides immitis*, and *Pneumocystis carinii*.

The term "protozoa" refers to the phylum of animals that have an essentially acellular structure through varying from simple uninucleate protoplasts (as most amoebas) to cell colonies (such as volvox), syncytia (such as pelomyxa), or highly organized protoplasts (such as various higher ciliates) that are more complex in organization and differentiation than most metazoan cells. Exemplary parasitic protozoa include the *Plasmodium* species (such as *Plasmodium vivax, Plasmodium falciparum, Plasmodium ovale* and *Plasmodium malariae*), *Leishmania* species, *Toxoplasma gondii, Trypanosoma cruzi, Pneumocystis carinii, Entameba histolytica, Cryptosporidium parvum, Giardia lamblia*, and amoebae. Parasitic protozoa also infect non-human animals such as fish. Protozoans can infect both external and internal portions of the fish including the gills, fins, skin, and digestive organs. External protozoa of major concern to aquaculturists include members of the genus *Costia, Chilodon, Scyphidia, Trichodina, Epistylis, Carchesium*, and *Trichophrya*. The external ciliate, *Ichthyophthirius multifiliis*, causes white spot disease known as Ick which is difficult to control and is often observed in crowded cultures of catfish and warm-water aquarium fish.

As used herein, the terms "infecting" and "infection" with a microorganism (such as bacterium and virus) refer to co-incubation of a target biological sample, (e.g., cell, tissue, etc.) with the microorganism under conditions such that nucleic acid sequences contained within the microorganism are introduced into one or more cells of the target biological sample. Infection may be in vitro and/or in vivo.

As used herein, the term "contacting" cells with an agent or microbe refers to placing the agent or a microbe in a location that will allow it to touch the cell in order to produce "contacted" cells. The contacting may be accomplished using any suitable method. For example, in one embodiment, contacting is by adding the agent or a microbe to a tube of cells. Contacting may also be accomplished by adding the agent to a culture of the cells. It is not meant to limit how the agent or microbe contacts the cells. In one embodiment, contacting may be accomplished by administration of agent or microbe to an animal in vivo.

As used herein, the term "anti-bacterial" and "antimicrobial" refers to any agent that reduces the growth of (including killing) microbes. It is intended that the term be used in its broadest sense, and includes, but is not limited to, agents described herein, for example those which are produced naturally or synthetically.

As used herein, the terms "antigen," "immunogen", "antigenic," "immunogenic," "antigenically active," and "immunologically active" refer to any substance that is capable of inducing a specific humoral or cell-mediated immune response. An immunogen generally contains at least one epitope. Immunogens are exemplified by, but not restricted to molecules which contain a peptide, polysaccharide, nucleic acid sequence, and/or lipid. Complexes of peptides with lipids, polysaccharides, or with nucleic acid sequences are also contemplated, including (without limitation) glycopeptide, lipopeptide, glycolipid, etc. These complexes are particularly useful immunogens where smaller molecules with few epitopes do not stimulate a satisfactory immune response by themselves.

As used herein, the term "antigen-presenting cell" and "APC" refers to a term most commonly used when referring to white blood cells that present processed antigenic peptide and MHC class I and/or II molecules to the T-cell receptor on lymphocytes, (e.g. macrophages, dendritic cells, B-cells and the like). However, other non-white blood cells can also be referred to as "antigen-presenting cells" since they present peptides within MHC class I and class II to T-cells and the like, e.g. as occurs with viral infected cells, cancer cells and the like.

As used herein, the terms "dendritic cell," "DC," and "professional antigen-presenting cells" can evoke an antigen response at least 10× greater in magnitude when compared to APCs under similar conditions (reviewed in Mellman et al. Trends Cell Biol. June; 8(6):231-7, 1998).

As used herein, the term "cell" refers to a single cell as well as to a population of (i.e., more than one) cells. The population may be a pure population comprising one cell type. Alternatively, the population may comprise more than one cell type. In the present invention, there is no limit on the number of cell types that a cell population may comprise.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

As used herein, the term "mixed cell culture," refers to a mixture of two or more types of cells. In some embodiments, the cells are cell lines that are not genetically engineered, while in other embodiments the cells are genetically engineered cell lines. In some embodiments the cells contain genetically engineered molecules. The present invention encompasses any combination of cell types suitable for the detection, identification, and/or quantitation of apoptosis in samples, including mixed cell cultures in which all of the cell types used are not genetically engineered, mixtures in which one or more of the cell types are genetically engineered and the remaining cell types are not genetically engineered, and mixtures in which all of the cell types are genetically engineered.

As used herein, the term "primary cell" is a cell that is directly obtained from a tissue (e.g. blood) or organ of an animal in the absence of culture. Typically, though not necessarily, a primary cell is capable of undergoing ten or fewer passages in vitro before senescence and/or cessation of proliferation. In contrast, a "cultured cell" is a cell that has been maintained and/or propagated in vitro for ten or more passages.

As used herein, the term "cultured cells" refer to cells that are capable of a greater number of passages in vitro before cessation of proliferation and/or senescence when compared to primary cells from the same source. Cultured cells include "cell lines" and "primary cultured cells."

As used herein, the term "cell line," refers to cells that are cultured in vitro, including primary cell lines, finite cell lines, continuous cell lines, and transformed cell lines, but does not require, that the cells be capable of an infinite number of passages m culture. Cell lines may be generated spontaneously or by transformation.

As used herein, the terms "primary cell culture," and "primary culture," refer to cell cultures that have been directly obtained from cells in vivo, such as from animal or insect tissue. These cultures may be derived from adults as well as fetal tissue.

As used herein, the terms "monolayer," "monolayer culture," and "monolayer cell culture," refer to a cell that has adhered to a substrate and grow as a layer that is one cell in thickness. Monolayers may be grown in any format, including but not limited to flasks, tubes, coverslips (e.g., shell vials), roller bottles, etc. Cells may also be grown attached to microcarriers, including but not limited to beads.

As used herein, the term "suspension" and "suspension culture" refers to cells that survive and proliferate without being attached to a substrate. Suspension cultures are typically produced using hematopoietic cells, transformed cell lines, and cells from malignant tumors.

As used herein, the terms "culture media," and "cell culture media," refers to media that are suitable to support the growth of cells in vitro (i.e., cell cultures). It is not intended that the term be limited to any particular culture medium. For example, it is intended that the definition encompass outgrowth as well as maintenance media. Indeed, it is intended that the term encompass any culture medium suitable for the growth of the cell cultures of interest.

As used herein the term, the term "in vitro" refers to an artificial environment and to processes or reactions that occur within an artificial environment. In vitro environments exemplified, but are not limited to, test tubes and cell cultures. The term "in vivo" refers to the natural environment (e.g., an animal or a cell) and to processes or reactions that occur within a natural environment.

As used herein, the term "proliferation" refers to an increase in cell number.

As used herein, the term "differentiation" refers to the maturation process cells undergo whereby they develop distinctive characteristics, and/or perform specific functions, and/or are less likely to divide.

As used herein, the terms "isolated," "to isolate," "isolation," "purified," "to purify," "purification," and grammatical equivalents thereof as used herein, refer to the reduction in the amount of at least one contaminant (such as protein and/or nucleic acid sequence) from a sample. Thus purification results in an "enrichment," i.e., an increase in the amount of a desirable protein and/or nucleic acid sequence in the sample.

As used herein, the term "amino acid sequence" refers to an amino acid sequence of a naturally occurring or engineered protein molecule. "Amino acid sequence" and like terms, such as "polypeptide," "peptide" or "protein" are not meant to limit the amino acid sequence to the complete, native amino acid sequence associated with the recited protein molecule.

As used herein, the term "Toll-like receptor proteins" and "membrane receptor proteins" refers to membrane spanning proteins that bind a ligand (e.g., a microbial molecule; endotoxin, such as LPS, LTA; dsRNA, and the like).

As used herein, the term "ligand" refers to a molecule that binds to a second molecule. A particular molecule may be referred to as either, or both, a ligand and second molecule. Examples of second molecules include a receptor of the ligand, and an antibody that binds to the ligand.

As is known in the art, "protein phosphorylation" is a common regulatory mechanism used by cells to selectively modify proteins carrying regulatory signals from outside the cell to the cytoplasm and ultimately the nucleus. The proteins that execute these biochemical modifications are a group of enzymes known as protein kinases. They may further be defined by the substrate residue that they target for phosphorylation. One group of protein kinases is the tyrosine kinases (TKs), which selectively phosphorylate a target protein on its tyrosine residues. Some tyrosine kinases are membrane-bound receptors (RTKs), and, upon activation by a ligand, can autophosphorylate as well as modify substrates. The initiation of sequential phosphorylation by ligand stimulation is a paradigm that underlies the action of such effectors as, for example, LPS, LTA, Lethal Toxin (LT), and interferons such as Interferon-$\beta$ (IFN-$\beta$). The receptors for these ligands are tyrosine kinases and provide the interface between the binding of a ligand (hormone, growth factor) to a target cell and the transmission of a signal into the cell by the activation of one or more biochemical pathways. Ligand binding to a receptor tyrosine kinase activates its intrinsic enzymatic activity (See, e.g., Ullrich and Schlessinger, Cell 61:203-212, 1990). Tyrosine kinases can also be cytoplasmic, non-receptor-type enzymes and act as a downstream component of a signal transduction pathway.

As used herein, the term "protein kinase" refers to a protein that catalyzes the addition of a phosphate group from a nucleoside triphosphate to an amino acid in a protein. Kinases comprise the largest known enzyme superfamily and vary widely in their target proteins. Kinases can be categorized as protein tyrosine kinases (PTKs), which phosphorylate tyrosine residues, and protein serine/threonine kinases (STKs), which phosphorylate serine and/or threonine residues and the like. Some kinases have dual specificity for both serine/threonine and tyrosine residues. Almost all kinases contain a conserved 250-300 amino acid catalytic domain. This domain can be further divided into 11 subdomains. N-terminal subdomains I-IV fold into a two-lobed structure that binds and orients the ATP donor molecule, and subdomain V spans the two lobes. C-terminal subdomains VI-XI bind the protein substrate and transfer the gamma phosphate from ATP to the hydroxyl group of a serine, threonine, or tyrosine residue. Each of the 11 subdomains contains specific catalytic residues or amino acid motifs characteristic of that subdomain. For example, subdomain I contains an 8-amino acid glycine-rich ATP binding consensus motif, subdomain II contains a critical lysine residue that contributes to maximal catalytic activity, and subdomains VI through IX comprise the highly conserved catalytic core. STKs and PTKs also contain distinct sequence motifs in subdomains VI and VIII, which may confer hydroxyamino acid specificity. Some STKs and PTKs possess structural characteristics of both families. In addition, kinases may also be classified by additional amino acid sequences, generally between 5 and 100 residues, which either flank or occur within the kinase domain.

Non-transmembrane PTKs form signaling complexes with the cytosolic domains of plasma membrane receptors. Receptors that signal through non-transmembrane PTKs include cytokine, hormone, and antigen-specific lymphocytic receptors. Many PTKs were first identified as oncogene products in cancer cells in which PTK activation was no longer subject to normal cellular controls. In fact, about one third of the known oncogenes encode PTKs. Furthermore, cellular transformation (oncogenesis) is often accompanied by increased tyrosine phosphorylation activity (See, e.g., Carbonneau, H. and Tonks, Annu. Rev. Cell Biol. 8:463-93, 1992). Regulation of PTK activity may therefore be an important strategy in controlling some types of cancer.

Examples of protein kinases include, but are not limited to, cAMP-dependent protein kinase, protein kinase C, and cyclin-dependent protein kinases (See, e.g., U.S. Pat. Nos. 6,034,228; 6,030,822; 6,030,788; 6,020,306; 6,013,455; 6,013,464; and 6,015,807, all of which are incorporated herein by reference).

As used herein, the term "protein phosphatase" refers to proteins that remove a phosphate group from a protein. Protein phosphatases are generally divided into two groups, receptor-type and non-receptor type (e.g. intracellular) proteins. An additional group includes dual specificity phosphatases. Most receptor-type protein tyrosine phosphatases contain two conserved catalytic domains, each of which encompasses a segment of 240 amino acid residues (See e.g., Saito et al. Cell Growth and Diff. 2:59, 1991). Receptor protein tyrosine phosphatases can be subclassified further based upon the amino acid sequence diversity of their extracellular domains (See e.g., Krueger et al. Proc. Natl. Acad. Sci. USA 89:7417-7421, 1992). Examples of protein phosphatases include, but are not limited to, human protein phosphatase (PROPHO), FIN13, cdc25 tyrosine phosphatase, protein tyrosine phosphatase (PTP) 20, PTP 1D, PTP-D1, PTP lambda., PTP-S31 (See e.g., U.S. Pat. Nos. 5,853,997; 5,976, 853; 5,294,538; 6,004,791; 5,589,375; 5,955,592; 5,958,719; and 5,952,212; all of which are incorporated herein by reference).

As used herein, the term "activating" when in reference to a biochemical response (such as kinase activity) and/or cellular response (such as cell proliferation) refers to increasing the biochemical and/or cellular response.

As used herein, the term "activated" when in reference to a cell, refers to a cell that has undergone a response that alters its physiology and shifts it towards making a biologically response and becoming biologically "active" hence "activated." For example, a monocyte becomes activated to mature into a macrophage. For another example, a macrophage becomes activated upon contact with an endotoxin (such as LPS) wherein the activated macrophage can produce an increased level and/or type of a molecule associated with activation (e.g. iNOS, MMP-12 Metalloelastase and the like). In another example, an immature dendritic cell becomes activated to mature into a functional dendritic cell. An "activated" cell does not necessarily, although it may, undergo growth or proliferation. Typically, activation of macrophages and DCs, unlike lymphocytes such as T-cells, B-cells and the like, does not stimulate proliferation. Activation can also induce cell death such as in activation-induced cell death (AICD) of T cells. In one embodiment of the present invention, activation can lead towards apoptotic death.

As used herein, the terms "naturally occurring," "wild-type" and "wt" as used herein when applied to a molecule or composition (such as nucleotide sequence, amino acid sequence, cell, apoptotic blebs, external phosphatidylserine, etc.), mean that the molecule or composition can be found in nature and has not been intentionally modified by man. For example, a naturally occurring polypeptide sequence refers to a polypeptide sequence that is present in an organism that can be isolated from a source in nature, wherein the polypeptide sequence has not been intentionally modified by man.

The terms "derived from" and "established from" when made in reference to any cell disclosed herein refer to a cell which has been obtained (e.g., isolated, purified, etc.) from the parent cell in issue using any manipulation, such as, without limitation, infection with virus, transfection with DNA sequences, treatment and/or mutagenesis using for example chemicals, radiation, etc., selection (such as by serial culture) of any cell that is contained in cultured parent cells. A derived cell can be selected from a mixed population by virtue of response to a growth factor, cytokine, selected progression of cytokine treatments, adhesiveness, lack of adhesiveness, sorting procedure, and the like.

As used herein, the term "biologically active," refers to a molecule (e.g. peptide, nucleic acid sequence, carbohydrate molecule, organic or inorganic molecule, and the like) having structured, regulatory, and/or biochemical functions.

Unless defined otherwise in reference to the level of molecules and/or phenomena, the terms "reduce," "inhibit," "diminish," "suppress," "decrease," and grammatical equivalents (or example, reducing, reduced, and the like) when in reference to the level of any molecule (e.g., nucleic acid sequence, protein sequence, apoptotic blebs, external phosphatidylserine, etc.), and/or phenomenon (e.g., apoptosis, cell death, cell survival, cell proliferation, caspase cleavage, receptor dimerization, receptor complex formation, phosphorylation, DNA fragmentation, molecule translocation, binding to a molecule, expression of a nucleic acid sequence, transcription of a nucleic acid sequence, enzyme activity, etc.) in a first sample relative to a second sample, mean that the quantity of molecule and/or phenomenon in the first sample is lower than in the second sample by any amount that is statistically significant using any art-accepted statistical method of analysis. In one embodiment, the reduction may be determined subjectively, for example when a patient refers to their subjective perception of disease symptoms, such as pain, difficulty in breathing, clarity of vision, nausea, tiredness, etc. In another embodiment, the quantity of molecule and/or phenomenon in the first sample is at least 10% lower than, at least 25% lower than, at least 50% lower than, at least 75% lower than, and/or at least 90% lower than the quantity of the same molecule and/or phenomenon in a second sample.

As exemplified herein, in one embodiment, the quantity of substance and/or phenomenon in the first sample is at least 5% lower than the quantity of the same substance and/or phenomenon in a second sample (e.g. FIG. 13b and the like). In another embodiment, the quantity of the substance and/or phenomenon in the first sample is at least 20% lower than the quantity of the same substance and/or phenomenon in a second sample (e.g. FIG. 3c, FIG. 6d, FIG. 11 and the like). In yet another embodiment, the quantity of the substance and/or phenomenon in the first sample is at least 50% lower than the quantity of the same substance and/or phenomenon in a second sample (e.g. FIG. 6a, FIG. 6d, and the like). In a further embodiment, the quantity of the substance and/or phenomenon in the first sample is at least 75% lower than the quantity of the same substance and/or phenomenon in a second sample (e.g. FIG. 6a, FIG. 6d, and the like). In yet another embodiment, the quantity of the substance and/or phenomenon in the first sample is at least 90% lower than the quantity of the same substance and/or phenomenon in a second sample (e.g. FIG. 3e, FIG. 4a and the like). In one embodiment, the reduction may be determined subjectively, for example when comparing DNA fragmentation (e.g. FIG. 1c and the like), mRNA levels (FIG. 3e and the like), etc.

As used herein, the term "apoptosis" refers to the process of non-necrotic cell death that takes place in metazoan animal cells following activation of an intrinsic cell suicide program: Apoptosis is a normal process in the proper development and homeostasis of metazoan animals and usually leads to cell death. Apoptosis is also triggered pathologically by microbial infections resulting in increasing susceptibility to apoptosis and/or outright death. Apoptosis involves sequential characteristic morphological and biochemical changes. One early marker of apoptosis is the flipping of plasma membrane phosphatidylserine, inside to outside, with cellular blebbing called "zeiosis," of plasma membrane releasing vesicles containing cellular material including RNA and DNA as apoptotic bodies. During apoptosis, there is cell expansion followed by shrinkage through release of apoptotic bodies and lysis of the cell, nuclear collapse and fragmentation of the nuclear chromatin, at certain intranucleosomal sites, due to activation of endogenous nucleases. Apoptotic bodies are typically phagocytosed by other cells, in particular immunocytes such as monocytes, macrophages, immature dendritic cells and the like. One of skill in the art appreciates that reducing the ability to undergo apoptosis results in increased cell survival, without necessarily (although it may include) increasing cell proliferation. Accordingly, as used herein, the terms "reduce apoptosis" and "increase survival" are equivalent. Also, as used herein, the terms "increase apoptosis" and "reduced survival" are equivalent.

Apoptosis may be determined but not limited to, the assays described herein and include methods known in the art. For example, apoptosis may be determined by techniques for detecting DNA fragmentation, (for example any version of the Terminal deoxynucleotidyl transferase (TdT)-mediated dUTP Nick End-Labeling TUNEL technique originally developed by Gavrieli et al. J Cell Biol. 1992 November; 119(3):493-501, nuclear staining with nucleic acid dyes such as Hoechst 33342, Acridine Orange and the like, and detecting DNA "ladder" fragmentation patterns associated with apoptosis (e.g. DNA gels and the like)). In one embodiment, apoptosis is measured by TUNEL (for example, Park et al. Science 297, 2048-51, 2002). In one embodiment apoptosis is measured by observing DNA fragmentation in a ladder pattern (for example, Park et al. Science 297, 2048-51, 2002). Apoptosis may be determined by morphological measurements including but not limited to measuring live cells, early apoptotic cells, late apoptotic cells and cell death via apoptosis. For example, the cells' increased display of externally flipped phosphatidylserine, an early indicator of apoptosis, binds external Annexin-V. Thus Annexin-V attached to fluorescent molecules can be used to stain non permeablized cells and often further combined with vital dyes (example propidium Iodide (PI), Ethidium Bromide (EtBr) and the like) allowing fluorescent activated cell sorting (FACS) analysis measuring of live, early apoptotic, late apoptotic and dead cells (Ozawa et al. J Exp Med. 1999 Feb. 15; 189(4):711-8). Further, general live v. dead assays may also be employed, for example double staining with EtBr and Calcein AM for live microscopy determinations and FACS. Apoptosis may be determined by the presence of molecular fragments in apoptotic cells not present in live nonapoptotic cells. For example, caspase molecules such as Caspases-3, 6, 7, and 9 and the like, are cleaved during apoptotic processes, release of cytochrome c, PARP (poly (ADP-ribose) polymerase) cleavage, and the like. Thus detecting the increased presence of predictable sizes of cleaved caspase subunits in apoptotic cells as compared to nonapoptotic cells indicate that cells are apoptotic. Furthermore, apoptosis may be monitored by changes in protein activity of molecules that decrease or increase cell survival and/or proliferation. For example, protein kinases and nuclear factors increase in activity during apoptosis and serve to either contribute to the apoptotic process or protect against apoptotic damage.

As used herein, the term "cellular response" refers to an increase or decrease of activity by a cell. For example, the "cellular response" may constitute but is not limited to apoptosis, death, DNA fragmentation, blebbing, proliferation, differentiation, adhesion, migration, DNA/RNA synthesis, gene transcription and translation, and/or cytokine secretion or cessation of such processes. A "cellular response" may comprise an increase or decrease of dephosphorylation, phosphorylation, calcium flux, target molecule cleavage, protein-protein interaction, nucleic acid-nucleic acid interaction, and/or protein/nucleic acid interaction and the like. As used herein, the term "target molecule cleavage" refers to the splitting of a molecule (for example in the process of apoptosis, cleavage of procaspases into fragments, cleavage of DNA into predicable sized fragments and the like). As used herein, the term "interaction" refers to the reciprocal action or influence of two or more molecules on each other.

As used herein, the term "phosphorylation" refers to the addition of phosphate groups. Protein phosphorylation is catalyzed by protein kinases that attach phosphate groups to hydroxyls of Ser, Thr and/or Tyr side chains. As used herein, the term "dephosphorylation" refers to the removal of a phosphate group. Protein dephosphorylation is catalyzed by protein phosphatases that remove phosphate groups from the side chains of Ser, Thr, and/or Tyr.

As used herein, the term "transgenic" when used in reference to a cell refers to a cell which contains a transgene, or whose genome has been altered by the introduction of a transgene. The term "transgenic" when used in reference to a tissue or to a plant refers to a tissue or plant, respectively, which comprises one or more cells that contain a transgene, or whose genome has been altered by the introduction of a transgene. Transgenic cells, tissues and plants may be produced by several methods including the introduction of a "transgene" comprising nucleic acid (usually DNA) into a target cell or integration of the transgene into a chromosome of a target cell by way of human intervention, such as by the methods described herein.

As used herein, the term "transgene" as used herein refers to any nucleic acid sequence that is introduced into the cell by experimental manipulations. A transgene may be an "endogenous DNA sequence" or a "heterologous DNA sequence" (i.e., "foreign DNA"). The term "endogenous DNA sequence" refers to a nucleotide sequence that is naturally found in the cell into which it is introduced so long as it does not contain some modification (e.g., a point mutation, the presence of a selectable marker gene, etc.) relative to the naturally-occurring sequence. Examples of Toll-like receptor 4 mutations and variants, herein incorporated by reference, are shown in U.S. Pat. No. 6,740,487, U.S. Patent Appln. No. 20020173001A1; mutations associated with atherosclerosis in U.S. Patent Appln. No. 20030232352A1, PCT publication WO03/050137 and PCT publication WO03/035110. The term "heterologous DNA sequence" refers to a nucleotide sequence that is ligated to, or is manipulated to become ligated to, a nucleic acid sequence to which it is not ligated in nature, or to which it is ligated at a different location in nature. Heterologous DNA is not endogenous to the cell into which it is introduced, but has been obtained from another cell. Heterologous DNA also includes an endogenous DNA sequence that contains some modification. Generally, although not necessarily, heterologous DNA encodes RNA and proteins that are not normally produced by the cell into which it is expressed. Examples of heterologous DNA include reporter genes, transcriptional and translational regulatory sequences, selectable marker proteins (e.g., proteins which confer drug resistance), etc.

As used herein, the terms "agent," "test agent," "molecule," "test molecule," "compound," and "test compound" as used interchangeably herein, refer to any type of molecule (for example, a peptide, nucleic acid, carbohydrate, lipid, organic molecule, and inorganic molecule, etc.) any combination molecule for example glycolipid, etc.) obtained from any source (for example, plant, animal, protist, and environmental source, etc.), or prepared by any method (for example, purification of naturally occurring molecules, chemical synthesis, and genetic engineering methods, etc.). Test agents are exemplified by, but not limited to individual and combinations of antibodies, chimeric molecules (for example, herein incorporated by reference, U.S. Patent Appln. No. 20040009167A1), nucleic acid sequences, and other agents as further described below.

In one embodiment, the term "test agent" refers to any chemical entity, pharmaceutical, drug, and the like that can be used to treat or prevent a disease, illness, sickness, or disorder of bodily function. Test agents comprise both known and potential therapeutic agents. A test agent can be determined to be therapeutic by screening using the screening methods of the present invention. A "known therapeutic agent" refers to a therapeutic agent that has been shown (e.g., through animal trials or prior experience with administration to humans) to be effective in such treatment or prevention. In other words, a known therapeutic agent is not limited to an agent efficacious in the treatment of disease (e.g., cancer). Agents are exemplified by, but not limited to, antibodies, nucleic acid sequences such as ribozyme sequences, and other agents as further described herein. Examples of using toll-like receptor-4 inhibitors, herein incorporated by reference, are shown in U.S. Patent Appln. Nos. 20030077279A1; 20020192217A1. Examples of identifying agents for an anti-tumor PKR assay are described in U.S. Pat. No. 5,670,330.

The test agents identified by and/or used in the invention's methods include any type of molecule (for example, a peptide, nucleic acid, carbohydrate, lipid, organic, and inorganic molecule, etc.) obtained from any source (for example, plant, animal, and environmental source, etc.), or prepared by any method (for example, purification of naturally occurring molecules, chemical synthesis, and genetic engineering methods, etc.).

The terms "chosen from A, B and C" and "chosen from one or more of A, B and C" are equivalent terms that mean selecting any one of A, B, and C, or any combination of A, B, and C.

As used herein, the term "comprising" when placed before the recitation of steps in a method means that the method encompasses one or more steps that are additional to those expressly recited, and that the additional one or more steps may be performed before, between, and/or after the recited steps. For example, a method comprising steps a, b, and c encompasses a method of steps a, b, x, and c, a method of steps a, b, c, and x, as well as a method of steps x, a, b, and c. Furthermore, the term "comprising" when placed before the recitation of steps in a method does not (although it may) require sequential performance of the listed steps, unless the content clearly dictates otherwise. For example, a method comprising steps a, b, and c encompasses, for example, a method of performing steps in the order of steps a, c, and b, the order of steps c, b, and a, and the order of steps c, a, and b, etc.

Unless otherwise indicated, all numbers expressing quantities of ingredients, properties such as molecular weight, reaction conditions, and so forth as used herein, are to be understood as being modified in all instances by the term "about." Accordingly, unless indicated to the contrary, the numerical parameters herein are approximations that may vary depending upon the desired properties sought to be obtained by the present invention. At the very least, and without limiting the application of the doctrine of equivalents to the scope of the claims, each numerical parameter should at least be construed in light of the number of reported significant digits and by applying ordinary rounding techniques. Notwithstanding that the numerical ranges and parameters describing the broad scope of the invention are approximations, the numerical values in the specific examples are reported as precisely as possible. Any numerical value, however, inherently contains standard deviations that necessarily result from the errors found in the numerical value's testing measurements.

The term "not" when preceding, and made in reference to, any particularly named molecule (e.g., nucleic acid sequence, protein sequence, apoptotic blebs, external phosphatidylserine, etc.), and/or phenomenon (e.g., apoptosis, cell death, cell survival, cell proliferation, caspase cleavage, receptor dimerization, receptor complex formation, DNA fragmentation, molecule translocation, binding to a molecule, expression of a nucleic acid sequence, transcription of a nucleic acid sequence, enzyme activity, etc.) means that only the particularly named molecule or phenomenon is excluded.

The term "altering" and grammatical equivalents as used herein in reference to the level of any molecule (e.g., nucleic acid sequence, protein sequence, apoptotic blebs, external phosphatidylserine, etc.), and/or phenomenon (e.g., apoptosis, cell death, cell survival, cell proliferation, caspase cleavage, receptor dimerization, receptor complex formation, DNA fragmentation, molecule translocation, binding to a molecule, expression of a nucleic acid sequence, transcription of a nucleic acid sequence, enzyme activity, etc.) refers to an increase and/or decrease in the quantity of the molecule and/or phenomenon, regardless of whether the quantity is determined objectively, and/or subjectively.

Unless defined otherwise in reference to the level of molecules and/or phenomena, the terms "increase," "elevate," "raise," and grammatical equivalents when in reference to the level of any molecule (e.g., nucleic acid sequence, protein sequence, apoptotic blebs, external phosphatidylserine, etc.), and/or phenomenon (e.g., apoptosis, cell death, cell survival, cell proliferation, caspase cleavage, receptor dimerization, receptor complex formation, DNA fragmentation, molecule translocation, binding to a molecule, expression of a nucleic acid sequence, transcription of a nucleic acid sequence, enzyme activity, etc.) in a first sample relative to a second sample, mean that the quantity of the molecule and/or phenomenon in the first sample is higher than in the second sample by any amount that is statistically significant using any art-accepted statistical method of analysis. In one embodiment, the increase may be determined subjectively, for example when a patient refers to their subjective perception of disease symptoms, such as pain, difficulty in breathing, clarity of vision, nausea, tiredness, etc. In another embodiment, the quantity of the molecule and/or phenomenon in the first sample is at least 10% greater than, at least 25% greater than, at least 50% greater than, at least 75% greater than, and/or at least 90% greater than the quantity of the same molecule and/or phenomenon in a second sample.

Reference herein to any specifically named protein (such as Protein Kinase R, Toll-like receptor-4, etc.) refers to any and all equivalent fragments, fusion proteins, and variants of the specifically named protein, having at least one of the biological activities (such as those disclosed herein and/or known in the art) of the specifically named protein, wherein the biological activity is detectable by any method.

The term "fragment" when in reference to a protein (such as Protein Kinase R, Toll-like receptor-4, etc.) refers to a portion of that protein that may range in size from four (4) contiguous amino acid residues to the entire amino acid sequence minus one amino acid residue. Thus, a polypeptide sequence comprising "at least a portion of an amino acid sequence" comprises from four (4) contiguous amino acid residues of the amino acid sequence to the entire amino acid sequence.

The term "fusion protein" refers to two or more polypeptides that are operably linked. The term "operably linked" when in reference to the relationship between nucleic acid sequences and/or amino acid sequences refers to linking the sequences such that they perform their intended function. For example, operably linking a promoter sequence to a nucleotide sequence of interest refers to ling the promoter sequence and the nucleotide sequence of interest in a manner such that the promoter sequence is capable of directing the transcription of the nucleotide sequence of interest and/or the synthesis of a polypeptide encoded by the nucleotide sequence of interest. The term also refers to the linkage of amino acid sequences in such a manner so that a, functional protein is produced.

The term "variant" of a protein (such as Protein Kinase R, Toll-like receptor-4, etc.) as used herein is defined as an amino acid sequence which differs by insertion, deletion, and/or conservative substitution of one or more amino acids from the protein of which it is a variant. The term "conservative substitution" of an amino acid refers to the replacement of that amino acid with another amino acid which has a similar hydrophobicity, polarity, and/or structure. For example, the following aliphatic amino acids with neutral side chains may be conservatively substituted one for the other: glycine, alanine, valine, leucine, isoleucine, serine, and threonine. Aromatic amino acids with neutral side chains which may be conservatively substituted one for the other include phenylalanine, tyrosine, and tryptophan. Cysteine and methionine are sulphur-containing amino acids which may be conservatively substituted one for the other. Also, asparagine may be conservatively substituted for glutamine, and vice versa, since both amino acids are amides of dicarboxylic amino acids. In addition, aspartic acid (aspartate) may be conservatively substituted for glutamic acid (glutamate) as both are acidic, charged (hydrophilic) amino acids. Also, lysine, arginine, and histidine may be conservatively substituted one for the other since each is a basic, charged (hydrophilic) amino acid. Guidance in determining which and how many amino acid residues may be substituted, inserted or deleted without abolishing biological and/or immunological activity may be found using computer programs well known in the art, for example, DNAStar™ software. In one embodiment, the sequence of the variant has at least 95% identity, at least 90% identity, at least 85% identity, at least 80% identity, at least 75% identity, at least 70% identity, and/or at least 65% identity with the sequence of the protein in issue.

Reference herein to any specifically named nucleotide sequence (such as a sequence encoding Protein Kinase R, Toll-like receptor-4, etc.) includes within its scope any and all equivalent fragments, homologs, and sequences that hybridize under highly stringent and/or medium stringent conditions to the specifically named nucleotide sequence, and that have at least one of the biological activities (such as those disclosed herein and/or known in the art) of the specifically named nucleotide sequence, wherein the biological activity is detectable by any method.

The "fragment" or "portion" may range in size from an exemplary 5, 10, 20, 50, or 100 contiguous nucleotide residues to the entire nucleic acid sequence minus one nucleic acid residue. Thus, a nucleic acid sequence comprising "at least a portion of" a nucleotide sequence (such as sequences encoding Protein Kinase R, Toll-like receptor-4, etc.) comprises from five (5) contiguous nucleotide residues of the nucleotide sequence to the entire nucleotide sequence.

The term "homolog" of a specifically named nucleotide sequence refers to an oligonucleotide sequence which exhibits greater than 50% identity to the specifically named nucleotide sequence (such as a sequence encoding Protein Kinase R, Toll-like receptor-4, etc). Alternatively, or in addition, a homolog of a specifically named nucleotide sequence is defined as an oligonucleotide sequence which has at least 95% identity, at least 90% identity, at least 85% identity, at least 80% identity, at least 75% identity, at least 70% identity, and/or at least 65% identity to nucleotide sequence in issue.

With respect to sequences that hybridize under stringent conditions to the specifically named nucleotide sequence (such as a sequence encoding Protein Kinase R, Toll-like receptor-4, etc), high stringency conditions comprise conditions equivalent to binding or hybridization at 68° C. in a solution containing 5×SSPE, 1% SDS, 5×Denhardt's reagent and 100 µg/ml denatured salmon sperm DNA followed by washing in a solution containing 0.1×SSPE, and 0.1% SDS at 68° C. "Medium stringency conditions" when used in reference to nucleic acid hybridization comprise conditions equivalent to binding or hybridization at 42° C. in a solution of 5×SSPE (43.8 g/l NaCl, 6.9 g/l $NaH_2PO_4$—$H_2O$ and 1.85 µl EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C.

The term "equivalent" when made in reference to a hybridization condition as it relates to a hybridization condition of interest means that the hybridization condition and the hybridization condition of interest result in hybridization of nucleic acid sequences which have the same range of percent (%) homology. For example, if a hybridization condition of interest results in hybridization of a first nucleic acid sequence with other nucleic acid sequences that have from 85% to 95% homology to the first nucleic acid sequence, then another hybridization condition is said to be equivalent to the hybridization condition of interest if this other hybridization condition also results in hybridization of the first nucleic acid sequence with the other nucleic acid sequences that have from 85% to 95% homology to the first nucleic acid sequence.

As will be understood by those of skill in the art, it may be advantageous to produce a nucleotide sequence encoding a protein of interest, wherein the nucleotide sequence possesses non-naturally occurring codons. Therefore, in some embodiments, codons preferred by a particular prokaryotic or eukaryotic host (Murray et al., Nucl. Acids Res., 17 (1989)) are selected, for example, to increase the rate of expression or to produce recombinant RNA transcripts having desirable properties, such as a longer half-life, than transcripts produced from naturally occurring sequence.

A "composition" comprising a particular polynucleotide sequence (such as a sequence encoding Protein Kinase R, Toll-like receptor-4, etc) and/or comprising a particular protein sequence (such as Protein Kinase R, Toll-like receptor-4, etc) as used herein refers broadly to any composition containing the recited polynucleotide sequence (and/or its equivalent fragments, homologs, and sequences that hybridize under highly stringent and/or medium stringent conditions to the specifically named nucleotide sequence) and/or the recited protein sequence (and/or its equivalent fragments, fusion proteins, and variants), respectively. The composition may comprise an aqueous solution containing, for example, salts (e.g., NaCl), detergents (e.g., SDS), and other components (e.g., Denhardt's solution, dry milk, salmon sperm DNA, etc.).

The terms nucleotide sequence "comprising a particular nucleic acid sequence" and protein "comprising a particular amino acid sequence" and equivalents of these terms, refer to any nucleotide sequence of interest (such as a sequence encoding Protein Kinase R, Toll-like receptor-4, etc.) and to any protein of interest (such as Protein Kinase R, Toll-like receptor-4, etc.), respectively, that contain the particularly named nucleic acid sequence (and/or its equivalent fragments, homologs, and sequences that hybridize under highly stringent and/or medium stringent conditions to the specifically named nucleotide sequence) and the particularly named amino acid sequence (and/or its equivalent fragments, fusion proteins, and variants), respectively. The invention does not limit the source (e.g., cell type, tissue, animal, etc.), nature (e.g., synthetic, recombinant, purified from cell extract, etc.), and/or sequence of the nucleotide sequence of interest and/or protein of interest. In one embodiment, the nucleotide sequence of interest and protein of interest include coding sequences of structural genes (e.g., probe genes, reporter genes, selection marker genes, oncogenes, drug resistance genes, growth factors, etc.).

DESCRIPTION OF THE INVENTION

The present invention relates to microbial infection, and in particular, the reduction of apoptosis associated with microbial infection, the screening of agents that reduce apoptosis, and the treatment and analysis of microbial infection in vivo. In one embodiment, the present invention relates to agents including but not limited to those agents capable of reducing the activity of Protein Kinase R and/or Toll-like receptor-4. The invention further provides methods for treating and/or analyzing microbial infections in cells, tissues, animals, etc. The methods of the invention are useful in, for example, in the diagnosis, prophylaxis, and reduction of symptoms of diseases and conditions that are associated with microbial infections including multiple infections (e.g., bacterial and viral infections). The methods of the present invention are also useful in identifying treatment agents, and in determining the mechanisms that underlie interactions of Protein Kinase R and/or Toll-like receptor-4 and macrophage apoptosis. For example, the identification of TRIF (see, FIG. 15), eIF2α (see, FIGS. 16 and 18), and interferon response factor 3 (see, FIG. 17) have been identified using the methods of the present invention.

In one embodiment, the agent that reduces activity of Protein Kinase R and/or Toll-like Receptor-4 alters activity of an adaptor protein. However, the present invention is not limited to alteration of adaptor protein. Other factors may also be regulated, including, but not limited to such molecules as MyD88 (myeloid differentiation factor 88), TIRAP (MAL; MyD88 adaptor-like protein), TRIF, TRAM (Toll-IL-1-resistance CM) domain-containing adaptor-inducing IFN-β (TRIF) related adaptor molecule) and the like. The terms "TRIF," "TIR domain containing adaptor inducing interferon-β," "Toll/IL-1 receptor-domain-containing adaptor inducing IFN-β," and "TICAM1" refer to equivalent Toll/IL1R (TIR) domain-containing adaptor molecules, RNA and DNA having homology (partial or complete). The terms "TIR" "Toll/IL-1R homologous region" refer to a molecule that share a whole or partial conserved amino acid domain also referred to as a "motif shared by the IL-1/Toll-like receptor (TLR) superfamily of receptors," for example, TLR4 and the like. An example of an agent that reduces activity of a TIR domain containing adaptor protein is demonstrated in Bartfai et al., PNAS 100(13), 7971-7976 (2003) herein incorporated by reference in its entirety. In one embodiment, reducing activity of an adaptor protein reduces Protein Kinase R and/or Toll-like Receptor-4 activity, see, for example, TRIF in FIG. 15). In one embodiment, the agent that reduces activity of Protein Kinase R and/or Toll-like Receptor-4 reduces activity of an adaptor protein.

Figure 17:
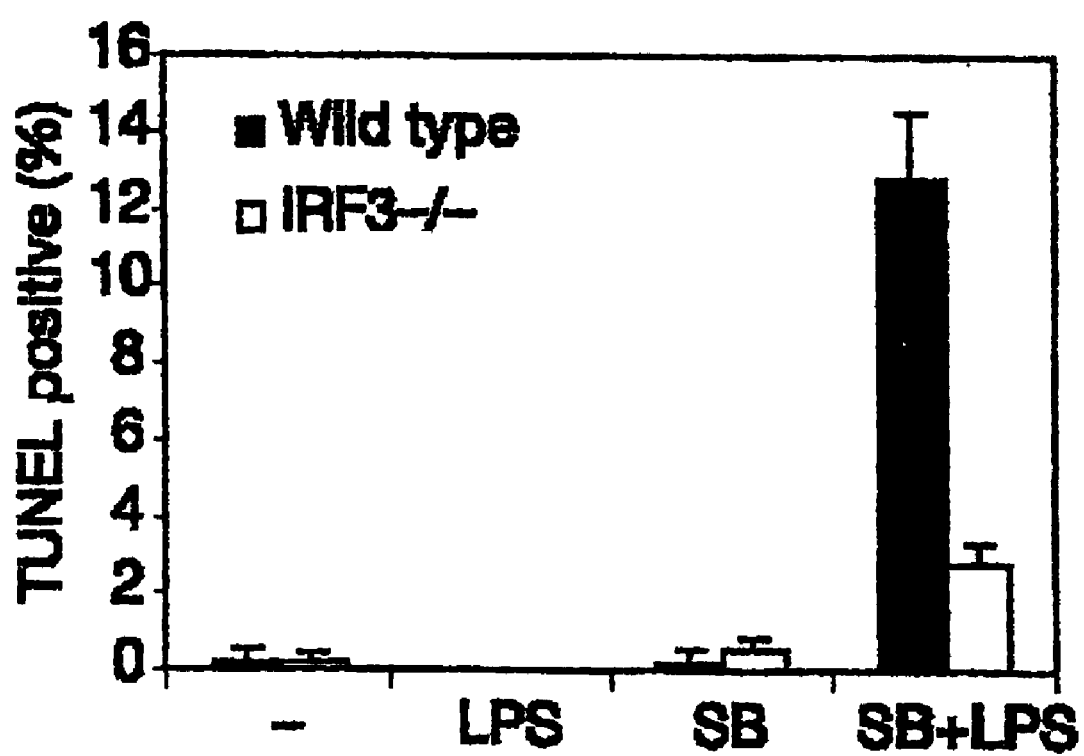
FIG. 17 shows an exemplary embodiment in which Interferon Response Factor 3 (IRF-3) is directly involved in induction of macrophage apoptosis.

In one embodiment, the agent that reduces activity of Protein Kinase R and/or Toll-like Receptor-4 is an agent that interferes with activation of interferon response factor 3 (IRF-3) (see, FIG. 17). Examples of agents that alter IRF-3 are disclosed in U.S. Patent Appln. No. 20020164694A1, herein incorporated by reference in its entirety. In one embodiment, the agent that reduces activity of Protein Kinase R and/or Toll-like Receptor-4 is an agent that reduces activation of interferon response factor 3 (IRF-3) (see, FIG. 17). In one embodiment, the agent that reduces activity of Protein Kinase R and/or Toll-like Receptor-4 is an agent that reduces interferon response factor 3 (IRF-3). The terms "interferon response factor 3," "IRF-3," "IRF3" refer to a member of the Interferon Regulatory Factor family. In one embodiment, IRF3 is a cytokine regulatory factor. In one embodiment, IRF3 is activated by dsRNA. In one embodiment, reducing activity of a IRF-3 molecule reduces Protein Kinase R and/or Toll-like Receptors activity, see, for example, IRF-3 in FIG. 17).

Figure 16:
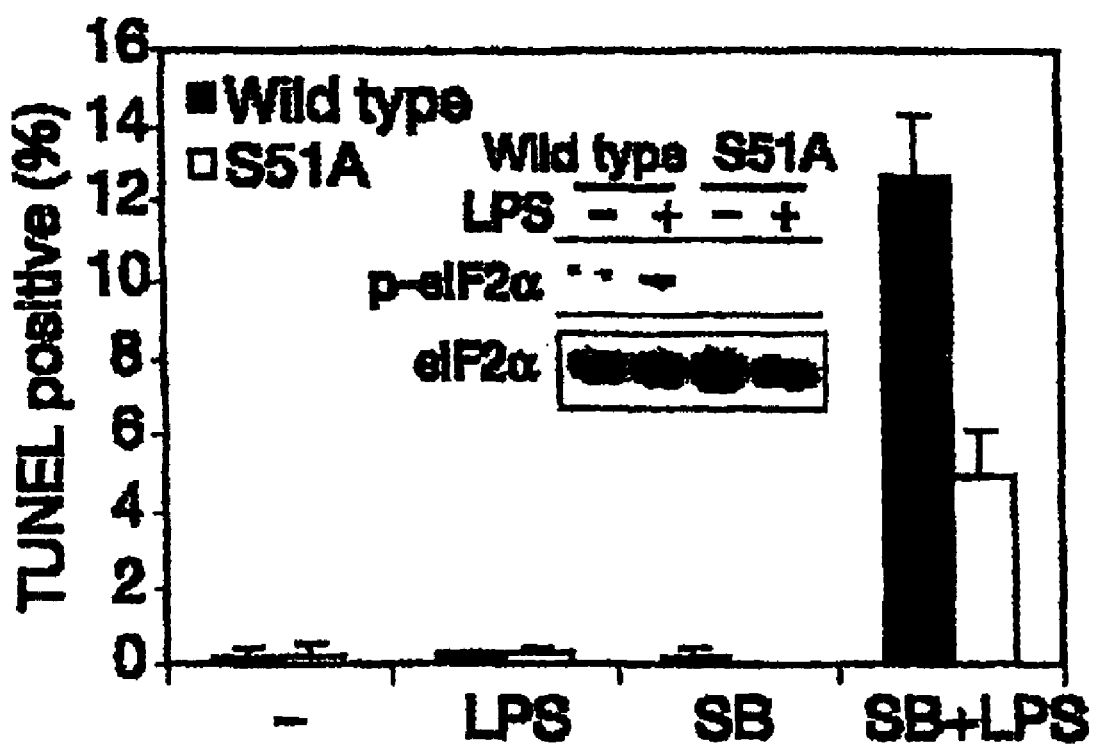
FIG. 16 shows an exemplary embodiment in which eIF2α phosphorylation is directly involved in induction of macrophage apoptosis.
Figure 18:
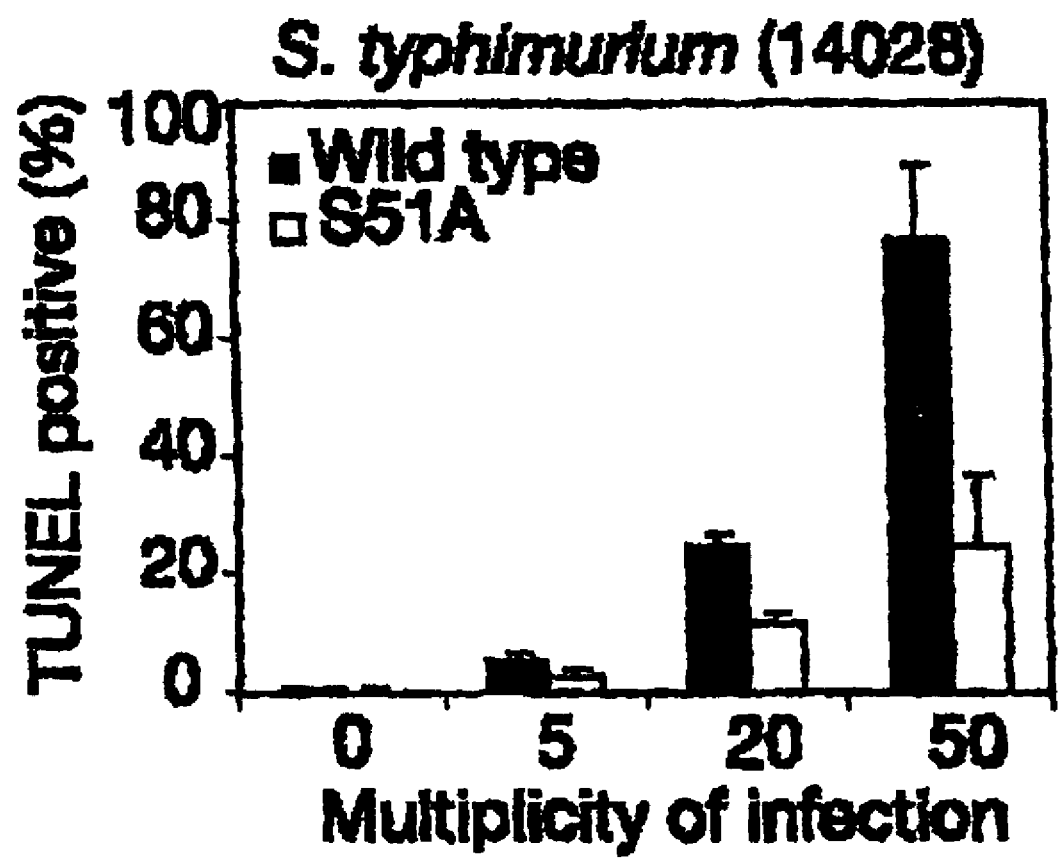
FIG. 18 shows an exemplary embodiment in which eIF2α-deficient macrophages are resistant to pathogen-induced apoptosis.

In one embodiment, the agent that reduces activity of Protein Kinase R and/or Toll-like Receptor-4 interferes with activation of eIF2α (see, FIGS. 16 and 18). Examples of methods for identifying agents that alter eIF2α are disclosed in U.S. Pat. Nos. 5,795,713 and 5,834,216. herein incorporated by reference in their entireties. The terms "eIF2α," "eukaryotic initiation factor 2-alpha," "eIF-2α" refers to a member of the Interferon Regulatory Factor family. In one embodiment, the agent that reduces activity of Protein Kinase R and/or Toll-like Receptor-4 promotes protein synthesis (see, FIGS. 16 and 18). In one embodiment, reducing activity of a eIF2α molecule reduces Protein Kinase R and/or Toll-like Receptor-4 activity, see, for example, eIF2α in FIGS. 16 and 18).

In one embodiment, the agent that reduces activity of Protein Kinase R and/or Toll-like Receptor-4 is a peptide, such as a peptide that interferes with apoptotic activity. The term "peptide" includes "peptide antagonist," "peptide agonist," "peptide inhibitor" and the like and refers to any length of amino acids in a synthesized amino acid sequence and natural sequence. An example of a peptide antagonist for Protein Kinase R is provided and incorporated herein by reference in U.S. Pat. No. 6,326,466 and PCT publication WO98/04717 wherein peptide agonist inhibit activation of PKR in order to stimulate eukaryotic cell proliferation. Another example is a PKR protein inhibitor based upon a natural protein produced by HSV-1, ICP34.5 herein incorporated by reference (Tallóczy et al. PNAS, Jan. 8, 2002, 99(1): 190-195). Further examples of natural proteins that act to inhibit PKR, herein incorporated by reference, include adenovirus VAI, vaccinia virus E3L, vaccinia virus encodes a protein, K3L, protein phosphatase PP1, herpes simplex virus type 1 encodes a protein that facilitates activation of PP1 including cellular inhibitors P58IPK, TRBP, Alu RNA, La antigen, p67 and the like (Kumar et al. Molecular and Cellular Biology, 19(2):1116-1125, February 1999).

In one preferred embodiment, the agent that reduces activity of Protein Kinase R and/or Toll-like Receptor-4 (PKR/TLR4), is an antibody, such as PKR or TLR4 peptide antibody, and/or PKR or TLR4 sequence antibody. The terms "antibody" and "immunoglobulin" are interchangeably used to refer to a glycoprotein or a portion thereof (including single chain antibodies), which is evoked in an animal by an immunogen and which demonstrates specificity to the immunogen, or, more specifically, to one or more epitopes contained in the immunogen. The term "antibody" includes polyclonal antibodies, monoclonal antibodies, naturally occurring antibodies as well as non-naturally occurring antibodies, including, for example, single chain antibodies, chimeric, bifunctional and humanized antibodies, as well as antigen-binding fragments thereof, including, for example, Fab, F(ab')$_2$, Fab fragments, Fd fragments, and Ev fragments of an antibody, as well as a Fab expression library. It is intended that the term "antibody" encompass any immunoglobulin (e.g., IgG, IgM, IgA, IgE, IgD, etc.) obtained from any source (e.g., humans, rodents, non-human primates, caprines, bovines, equines, ovines, etc.). The term "polyclonal antibody" refers to an immunoglobulin produced from more than a single clone of plasma cells; in contrast "monoclonal antibody" refers to an immunoglobulin produced from a single clone of plasma cells. Monoclonal and polyclonal antibodies may or may not be purified. For example, polyclonal antibodies contained in crude antiserum may be used in this unpurified state.

An example of a TLR antibody and an example of a contemplated TLR4 antibody, herein incorporated by reference in U.S. Patent Appln No. 20030032090A1, Hardiman et al. Feb. 13, 2003; Chiang and Beachy, Mech. Develop. 47, 225 (1994). An example of a target area on TLR4 for producing TLR4 antibodies is herein incorporated by reference, PCT publication WO00/77204 which discloses a biologically active fragment of TLR4 and variants thereof.

Naturally occurring antibodies may be generated in any species including murine, rat, rabbit, hamster, human, and simian species using methods known in the art. Non-naturally occurring antibodies can be constructed using solid phase peptide synthesis, can be produced recombinantly or can be obtained, for example, by screening combinatorial libraries consisting of variable heavy chains and variable light chains as previously described (Huse et al. Science 246:1275-1281, 1989). These and other methods of making, for example, chimeric, humanized, CDR-grafted, single chain, and bifunctional antibodies are well known to those skilled in the art (Winter and Harris, Immunol. Today 14:243-246, 1993; Ward et al. Nature 341:544-546, 1989; Hilyard et al. Protein Engineering: A practical approach (IRL Press 1992); and Borrabeck, Antibody Engineering, 2d ed. (Oxford University Press 1995)).

Those skilled in the art know how to make polyclonal and monoclonal antibodies which are specific to a desirable polypeptide. For the production of monoclonal and polyclonal antibodies, various host animals can be immunized by injection with the peptide corresponding to any molecule of interest in the present invention, including but not limited to rabbits, mice, rats, sheep, goats, chickens, etc. In one preferred embodiment, the peptide is conjugated to an immunogenic carrier (e.g., diphtheria toxoid, bovine serum albumin (BSA), or keyhole limpet hemocyanin (KLH)). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*.

For preparation of monoclonal antibodies directed toward molecules of interest in the present invention, any technique that provides for the production of antibody molecules by continuous cell lines in culture may be used (See, e.g., Harlow and Lane, *Antibodies: A Laboratory Manual, Cold Spring Harbor Laboratory Press*, Cold Spring Harbor, N.Y.). These include but are not limited to the hybridoma technique originally developed by Köhler and Milstein (Köhler and Milstein, Nature 256:495-497, 1975), as well as the trioma technique, the human B-cell hybridoma technique (See e.g., Kozbor et al. Immunol. Today 4:72, 1983), and the EBV-hybridoma technique to produce human monoclonal antibodies (Cole et al., in *Monoclonal Antibodies and Cancer Therapy*, Alan R. Liss, Inc., pp. 77-96, 1985). In some particularly preferred embodiments of the present invention, the present invention provides monoclonal antibodies of the IgG class.

In additional embodiments of the invention, monoclonal antibodies can be produced in germ-free animals utilizing technology such as that described in PCT/US90/02545. In addition, human antibodies may be used and can be obtained by using human hybridomas (Cote et al. Proc. Natl. Acad. Sci.

U.S.A. 80:2026-2030, 1983) or by transforming human B cells with EBV virus in vitro (Cole et al. in *Monoclonal Antibodies and Cancer Therapy*, Alan R. Liss, pp. 77-96, 1985).

Furthermore, techniques described for the production of single chain antibodies (See e.g., U.S. Pat. No. 4,946,778; herein incorporated by reference) can be adapted to produce single chain antibodies that specifically recognize a molecule of interest (e.g., at least a portion of an AUBP or mammalian exosome, as described herein). An additional embodiment of the invention utilizes the techniques described for the construction of Fab expression libraries (Huse et al. Science 246:1275-1281, 1989) to allow rapid and easy identification of monoclonal Fab fragments with the desired specificity for a particular protein or epitope of interest (e.g., at least a portion of an AUBP or mammalian exosome).

The invention also contemplates humanized antibodies. Humanized antibodies may be generated using methods known in the art, including those described in U.S. Pat. Nos. 5,545,806; 5,569,825 and 5,625,126, the entire contents of which are incorporated by reference. Such methods include, for example, generation of transgenic non-human animals which contain human immunoglobulin chain genes and which are capable of expressing these genes to produce a repertoire of antibodies of various isotypes encoded by the human immunoglobulin genes.

According to the invention, techniques described for the production of single chain antibodies (U.S. Pat. No. 4,946,778; herein incorporated by reference) can be adapted to produce specific single chain antibodies as desired. An additional embodiment of the invention utilizes the techniques known in the art for the construction of Fab expression libraries (Huse et al. Science, 246:1275-1281, 1989) to allow rapid and easy identification of monoclonal Fab fragments with the desired specificity.

Antibody fragments that contain the idiotype (antigen binding region) of the antibody molecule can be generated by known techniques. For example, such fragments include but are not limited to: the F(ab')2 fragment that can be produced by pepsin digestion of an antibody molecule; the Fab' fragments that can be generated by reducing the disulfide bridges of an F(ab')2 fragment, and the Fab fragments that can be generated by treating an antibody molecule with papain and a reducing agent.

In the production of antibodies, screening for the desired antibody can be accomplished by techniques known in the art (e.g., radioimmunoassay, ELISA [enzyme-linked immunosorbent assay], "sandwich" immunoassays, immunoradiometric assays, gel diffusion precipitin reactions, immunodiffusion assays, in situ immunoassays [e.g., using colloidal gold, enzyme or radioisotope labels], Western blots, precipitation reactions, agglutination assays (e.g., gel agglutination assays, hemagglutination assays, etc.), complement fixation assays, immunofluorescence assays, protein A assays, and immunoelectrophoresis assays, etc.

In an alternative embodiment, the agent that alters the level of binding of PKR and/or TLR4 with a PKR and/or TLR4 sequence, respectively, is a nucleic acid sequence. The terms nucleic acid sequence therein refer to two or more nucleotides which are covalently linked to each other. Included within this definition are oligonucleotides, polynucleotide, and fragments or portions thereof, DNA or RNA of genomic or synthetic origin which may be single- or double-stranded, and represent the sense or antisense strand. Nucleic acid sequences which are particularly useful in the instant invention include, without limitation, antisense sequences and ribozymes. In an example herein incorporated by reference, Flavell et al. Aug. 21, 2003 U.S. Patent Appln No, 20030157539A1, a nucleic acid inhibitor comprising IRAK-M reduces toll-like receptor signaling.

In one embodiment, the agent that alters the level of PKR and/or TLR4 with a PKR and/or TLR4 sequence, is an antisense nucleic acid sequence. Antisense sequences have been successfully used to inhibit the expression of several genes (Markus-Sekura, Anal. Biochem. 172:289-295, 1988; Hambor et al. J. Exp. Med. 168:1237-1245, 1988; and patent EP140308, incorporated in its entirety by reference) including the gene encoding VCAM1, one of the integrin $\alpha$-4/$\beta$-1 ligands (U.S. Pat. No. 6,252,043, incorporated in its entirety by reference). Further, in the Karras et al. U.S. Patent Appln No. 20030125272 A1, Jul. 3, 2003, PCT publication WO03/044163, herein incorporated by reference, antisense sequences were used to modulate Toll-like receptor-4 expression through function of nucleic acid molecules encoding Toll-like receptor-4, Human Toll-like receptor-4 (also known as TLR4 and hToll), the human homolog to the *Drosophila* protein known as Toll, was cloned from a human fetal liver/spleen library (Medzhitov et al. Nature, 1997, 388, 394-397), characterized, and mapped to chromosome 9q32-33 (Rock et al. Proc. Natl. Acad. Sci. U.S.A., 1998, 95, 588-593). Wherein Toll-like receptor-4 mRNA expression can be detected in the cells of the immune system: monocytes, macrophages, dendritic cells, $\gamma$.delta. T-cells, Th1 and Th2, $\alpha\beta$ T-cells, $\beta\beta$ T-cells, and B-cells (Sieling and Modlin, Scand. J. Infect. Dis., 2001, 33, 97-100). The terms "antisense DNA sequence" and "antisense sequence" as used herein interchangeably refer to a deoxyribonucleotide sequence whose sequence of deoxyribonucleotide residues is in reverse 5' to 3' orientation in relation to the sequence of deoxyribonucleotide residues in a sense strand of a DNA duplex. A "sense strand" of a DNA duplex refers to a strand in a DNA duplex which is transcribed by a cell in its natural state into a "sense mRNA." Sense mRNA generally is ultimately translated into a polypeptide. Thus, an "antisense DNA sequence" is a sequence which has the same sequence as the non-coding strand in a DNA duplex, and which encodes an "antisense RNA" (i.e., a ribonucleotide sequence whose sequence is complementary to a "sense mRNA" sequence). The designation (−) (i.e., "negative") is sometimes used in reference to the antisense strand, with the designation (+) sometimes used in reference to the sense (i.e., "positive") strand. Antisense RNA may be produced by any method, including synthesis by splicing an antisense DNA sequence to a promoter which permits the synthesis of antisense RNA. The transcribed antisense RNA strand combines with natural mRNA produced by the cell to form duplexes. These duplexes then block either the further transcription of the mRNA or its translation, or promote its degradation. One example of an antisense sequence used to modulate Protein kinase R, herein incorporated by reference, is U.S. Patent Appln No. 20030087855A1 and PCT publication WO03022222.

Antisense oligonucleotide sequences may be synthesized using any of a number of methods known in the art (such as solid support and commercially available DNA synthesizers, standard phosphoramidate chemistry techniques, and commercially available services, e.g., Genta, Inc.).

In some alternative embodiments, the agent that alters the level of PKR and/or TLR4 sequence is a ribozyme nucleic acid sequence, for example, a ribozyme, a hammerhead ribozyme, Inozyme, Zinzyme, G-cleaver, Amberzyme, or DNAzyme, and the like, herein incorporated by reference as described in U.S. Patent Appln. No. 20030119017A1, McSwiggen, Jun. 26, 2003. Ribozyme sequences have been successfully used to inhibit the expression of several genes including the gene encoding VCAM1, which is one of the integrin α-4/β-1 ligands (U.S. Pat. No. 6,252,043, incorporated in its entirety by reference). The term "ribozyme" refers to an RNA sequence that hybridizes to a complementary sequence in a substrate RNA and cleaves the substrate RNA in a sequence specific manner at a substrate cleavage site. Typically, a ribozyme contains a "catalytic region" flanked by two "binding regions." The ribozyme binding regions hybridize to the substrate RNA, while the catalytic region cleaves the substrate RNA at a "substrate cleavage site" to yield a "cleaved RNA product." Examples of ribosomes that modulate genes related to apoptosis are NF-KappaB genes, such as REL-A, REL-B, REL (c-rel), NFκB1 (p105/p50) and NFκB2 (p100)/p52/p49), herein incorporated by reference, are demonstrate in U.S. Patent Appln No. 20020177568A1, Stinchcomb, et al. Nov. 28, 2002. Further types of nucleic acid molecules used to modulate other types of apoptotic molecules including PKR and IKK genes, herein incorporated by reference, are demonstrated in U.S. Patent Appln. No. 20030119017A1, McSwiggen, et al. Jun. 26, 2003.

Molecules which find use as agents for specifically altering the level of specific binding of PKR and/or TLR4 with effector molecule sequences include organic molecules, inorganic molecules, and libraries of any type of molecule, which can be screened using a method of the invention, and which may be prepared using methods known in the art. These agents are made by methods for preparing oligonucleotide libraries (Gold et al. U.S. Pat. No. 5,270,163, herein incorporated by reference); peptide libraries (Koivunen et al. J. Cell Biol., 124: 373-380, 1994); peptidomimetic libraries (Blondelle et al. Trends Anal. Chem. 14:83-92, 1995); oligosaccharide libraries (York et al. Carb. Res. 285:99-128, 1996; Liang et al. Science 274:1520-1522, 1996; and Ding et al. Adv. Expt. Med. Biol. 376:261-269, 1995); lipoprotein libraries (de Kruif et al. FEBS Lett., 399:232-236, 1996); glycoprotein or glycolipid libraries (Karaoglu et al. J. Cell Biol. 130:567-577, 1995); or chemical libraries containing, for example, drugs or other pharmaceutical agents (Gordon et al. J. Med. Chem. 37:1385-1401, 1994; Ecker and Crook, Bio/Technology 13:351-360, 1995; U.S. Pat. No. 5,760,029, herein incorporated by reference). Libraries of diverse molecules also can be obtained from commercial sources.

Macrophages are pivotal effector cells of the innate immune system, vital for recognition and elimination of microbial pathogens (Aderem et al. Nature 406, 782-7, 2000). As used herein, the term "macrophage" and "macrophage cells" refers to a phagocytic cell of the myeloid lineage in the mononuclear phagocyte system (a system comprising blood monocytes and tissue macrophages). Macrophages are derived from the myeloid precursors such as those found in the bone marrow and thus share characteristics such as cell surface markers with many other myeloid derived cells (e.g., human macrophages can express numerous markers that are used to distinguish maturation stages, activation levels and functional characteristics such as CD11b, CD11c, CD16, CD68, CD14, CD80, CD86, HLA-DR and the like, mouse macrophages can express Mac-1, F4/80, and the like). As a further example, macrophages and dendritic cells are derived from similar primordial cells and thus share many characteristics with each other including identifying markers, capacity for becoming "activated" in response to antigens, phagocytic functions and the like for the greater purpose of responding to stimuli requiring a particular response. Macrophages and DCs are so closely related that CD34+ precursors in normal human bone marrow (BM) can be selectively cultured to generate populations of macrophages or DCs or mixed cultures of both (Szabolcs et al. Blood. June 1; 87(11):4520-30, 1996; Szabolcs et al. J Leukoc Biol. 1999 August; 66(2):205-8). Further, monocytes are known to develop into dendritic cells (DCs) that migrate to lymph nodes (LNs) and present antigens to T cells (see Chapts. 15-16, Fundamental Immunology Ed., Paul, Fifth Edition, September 2003). Macrophages are found throughout an organism in various stages of maturation and activation (e.g. monocytes, macrophages, activated macrophages, cytokine and/or chemokine activated macrophages (also referred to as Activated Killer Monocytes) and the like). Macrophages have a variety of morphological forms, phenotypes and functions suited for residing within each type of tissue (e.g. Kupffer cells in the liver, alveolar macrophages in the lungs, microglial in the brain and the like). Macrophages have different stages of attachment ranging from non-attached (e.g. suspension, free floating, monocytes in early stages of culture, and the like) as when circulating within the blood stream, to various intermediate stages of attachment (when migrating into and out of endothelium, in cell cultures and the like) and attached (e.g. within specific tissues, attached cultures and the like). Macrophages display a range of functional activities depending upon their maturation stage, activation state, tissue location, and attachment level. It is not intended that the present invention be limited to a particular function or phenotype or maturation stage of macrophage cells. In one embodiment, macrophages are cultured from bone marrow cells Park et al. Science 297, 2048-51, 2002; Chu et al. Cell 103, 909-18, 2000). In one embodiment, the macrophage cells are activated macrophages (for example mature macrophages, infected macrophages, cultured macrophages, cytokine induced macrophage, lymphocyte activated macrophages and the like). In one embodiment macrophage cells are phagocytic. In one embodiment macrophage cells contain numerous granules of bactericidal molecules. In one embodiment, the macrophage cells are monocytes (for example immature macrophages, and the like). In yet another embodiment, macrophages are immunocytes of myeloid lineage (for example, dendritic cells, myeloid dendritic cells and the like). In another embodiment, the macrophage cells are immunocytes functionally equivalent to macrophages (for example, Kupffer cells, microglia, astrocytes, and the like). In another embodiment, macrophage cells are immunocytes of lymphoid origin (for example, splenic cells, lymphoid derived dendritic cells, and the like). In one embodiment, macrophages are precursors to dendritic cells (Rotta et al. J Exp Med. 2003, Oct. 20; 198(8):1253-63). However they globally function as phagocytes that ingest microbes and particles for destruction and particularly in triggering microbial immune responses. Macrophages can trigger immune responses by presenting microbial antigens to immunocompetent cells while in an activated state. Many factors contribute to activating macrophages including microbial infection wherein said microbe is killed and degraded within the phagosome, cytokines and chemokines are being produced to recruit lymphoid cells and other types of leukocytes to sites of infection, and components of the pathogen are presented to T cells, resulting in adaptive immunity (Aderem et al. Nature 406, 782-7, 2000).

It is not intended that the present invention be limited to a particular source of macrophage cells. In one embodiment, macrophage cells are derived from bone-marrow cells (BMDM). In one embodiment, macrophage cells are derived from fetal-liver (FLDMs). In one embodiment, macrophage cells are located within an animal. In one embodiment, macrophages are located within the red pulp area of spleens.

It is not intended that the present invention be limited to a particular stage of development of the macrophage cell host. In one embodiment, macrophages cells are derived from mature (adult) animals. In one embodiment, macrophage cells are derived from embryonic day 14.5.

In one embodiment, the macrophage cells are activated macrophages (for example mature macrophages, infected macrophages, cultured macrophages, cytokine induced macrophages, lymphocyte activated macrophages and the like). In one embodiment macrophage cells are phagocytic. In one embodiment macrophage cells contain numerous granules of bactericidal molecules. In one embodiment, the macrophage cells are monocytes (for example immature macrophages, and the like). In yet another embodiment, macrophages are immunocytes of macrophage lineage (for example, dendritic cells, Langerhans cells, dermal dendritic cells and the like). In another embodiment, the macrophage cells are immunocytes functionally equivalent to macrophages (for example, Kupffer cells, microglia, astrocytes, and the like). In another embodiment, macrophage cells are immunocytes of lymphoid origin (for example, lymphoid derived dendritic cells, and the like).

Macrophages and other myeloid cells use Toll-like receptors (TLRs) as primary sensors that detect pathogen associated molecular patterns (PAMPs), which include components of bacterial cell walls, such as lipopolysaccharide (LPS) or lipoteichoiec acid (LTA), and viral nucleic acids, such as dsRNA2 (Medzhitov, Nat Rev Immunol 1, 135-45, 2001).

As used herein, "Toll-like receptor," "TLR," "pattern recognition receptors" and "PRRs" refer to molecules of the immune system to that respond to microbes and microbial molecules. In one embodiment, a TLR binds to microbial ligands. In one embodiment, a TLR binds to a PAMP. As used herein, "PAMP" and "pathogen-associated molecular pattern" refers to any molecule expressed by microbial pathogens that contain repetitive motifs "patterns" (e.g. lipopolysaccharide (LPS), peptidoglycan, mannan, and the like). It is not intended that the present invention be limited to a particular PAMP. In one embodiment, a PAMP is a molecule that activates a TLR. In one embodiment, a PAMP is a molecule that activates a TLR-4. In one embodiment, a PAMP is a LPS. In one embodiment, a PAMP is a LPS that activates TLR-4. In one embodiment, a PAMP is lipoteichoic acid (LTA). In one embodiment, macrophage cells express TLR. In one embodiment, macrophage cells express TLR4. In another embodiment, macrophage cells are any cell that is LPS-responsive. In another embodiment, the macrophage cells are any closely related immunocytes expressing TLR-4 (for example, white blood cells, undifferentiated immunocytes, immature dendritic cells of lymphoid lineage and the like). TLRs are involved in activation of macrophages and their effector functions, including anti-apoptotic signaling pathways. Certain pathogens, however, such as *Salmonella* spp., *Shigellae* spp., and *Yersiniae* spp. use specialized virulence factors to overcome these protective responses and induce macrophage apoptosis (Weinrauch and Zychlinsky, Annu Rev Microbiol 53, 155-87, 1999).

Apoptosis was also observed upon pretreatment of myeloid cells with type I interferons (IFN) followed by incubation with LPS (Adler et al. Biochem Biophys Res Commun 215, 921-7, 1995; Lehner et al. Blood 98, 736-42, 2001). Type I IFNs are produced in response to viral infections and it is well established that such infections, for instance with influenza virus, predispose affected individuals to excess mortality from common microbial pathogens, such as *Haemophilus influenzae* or *Streptococcus pneumoniae* (Abrahams et al. Lancet 1, 1-11, 1919; Oxford, Rev Med Virol 10(2):119-33, 2000). As used herein, the term "virus" and "viral" refers to obligate, ultramicroscopic, intracellular parasites incapable of autonomous replication (i.e., replication requires the use of the host cell's machinery). Although such microbes do not induce macrophage apoptosis on their own, it was observed that influenza virus infection can markedly enhance the susceptibility of myeloid cells to bacterial-induced apoptosis (Colamussi et al. Blood 93, 2395-403, 1999). It is the inventor's opinion that such an effect may contribute to the immunodeficiency that is commonly associated with viral infections (Ray, G. C. *Influenza, Respiratory Syncytial Virus, Adenovirus, and Other Respiratory Viruses*, ed. K. J., R.), Appleton & Lange, Newwalk, Conn., 1994).

As used herein, "double stranded RNA" and "dsRNA" refer to a double stranded ribonucleotide sequence. Double stranded RNA may be chemically synthesized and/or naturally occurring. For example naturally occurring dsRNA includes dsRNA segments (also referred to as dsRNA portions) that are found in, and may be isolated from, virus infected cells. Examples of synthesized segments are presented herein.

An example of a test agent that reduces apoptosis is an agent that interacts with Protein Kinase R to reduce the translation of viral RNA. An example of a screen for such an agent is described and incorporated by reference in U.S. Pat. Nos. 6,623,961, 5,738,985, 6,156,496, 6,579,674, 6,667,152 and 6,777,179; U.S. Patent Appln. Nos. 2002160976, 2002160977, 2003144226, 2003144226; and PCT publications WO9423041. Additionally, the test agent reduces apoptosis by inhibiting replication of viral dsRNA binding to Protein Kinase R. Recently, it was found that the anthrax bacterium, *B. anthracis*, which gained notoriety as a bioterrorism agent, can selectively induce apoptosis of activated macrophages (Park et al. Science 297, 2048-51, 2002). Induction of apoptosis by *B. anthracis* is mediated by its lethal toxin (LT), a complex between lethal factor (LF) and protective antigen (PA) (Hanna and Ireland, Trends Microbiol 7, 180-2, 1999). LF is a metalloprotease that cleaves and inactivates MAP kinase (MAPK) kinases (MKKs), the most critical of which for macrophage apoptosis is MKK6, an activator of p38 MAPK (Park et al. Science 297, 2048-51, 2002). Inhibition of p38 MAPK in activated macrophages also results in a robust apoptotic response (Park et al. Science 297, 2048-51, 2002). The mechanism by which anthrax LT or p38 inhibitors trigger apoptosis of activated macrophages has not been determined. Here, it is shown that the dsRNA responsive protein kinase (PKR) acts downstream to TLR4 in the pathway through which LT kills activated macrophages.

As used herein, the terms "Toll-like receptor-4," "TLR4," "TLR4," "human homologue of *Drosophila* Toll," "hToll" refers to equivalent proteins, RNA and DNA having homology (partial or complete) (Medzhitov et al. 1997, Nature. 388: 394-397; Rock et al. 1997, Proc. Natl. Acad. Sci. USA. 95: 558-592). TLR-4 was identified as the receptor for LPS, LTA, fibronectin, F protein from syncytial virus, and taxol, a plant diterpene structurally unrelated to LPS but possessing potent LPS-mimetic effects on murine cells. It is not intended that the present invention be limited to an individual TLR4 molecule for reducing TLR-4 activity. In one embodiment, TLR4 activity includes the serum protein LPS-binding protein (LBP) and the like. In one embodiment, TLR4 activity includes any molecules of the TLR4 signaling complex (for example, soluble CD14, GPI-anchored CD14, MD-2, heat shock protein (HSP) 70, HSP90, chemokine receptor 4, growth differentiation factor-5, CD11b and CD18 and the like). In another embodiment TLR4 includes any apoptotic molecules that are in functional contact with TLR4. In one embodiment, TLR4 includes functional portions within TLR4. In one embodiment TLR4 includes a TLR-4 receptor homodimer. In one embodiment TLR4 includes molecules involved with TLR4 homodimerization. In one embodiment, macrophage cells express TLR4.

As used herein, the terms "Protein Kinase R," "PKR," "double-stranded RNA dependent protein kinase," "dsRNA dependent kinase," "double-stranded RNA dependent eIF-2α kinase", "double-stranded RNA activated inhibitor," "DAI" (Jimenez-Garcia, et al. J. Cell Sci. 106:11-12, 1993), "dSI", "p68 kinase" (Lee, et al. J. Interferon Cytokine Res. 16:1073-1078, 1996), "dsRNA-PK" (Clemens, et al. J. Interferon Res. 13:241, 1993), and "interferon (IFN)-inducible serine/threonine protein that regulates protein synthesis through the phosphorylation of the alpha subunit of translation initiation factor 2 (eIF-2α)," refers to equivalent functions, proteins, RNA and DNA having homology (partial or complete). For example, homology comparisons between human and mouse PKR, Feng, et al. Proc. Natl. Acad. Sci. USA 89: 5447-5451, 1992). These terms also refer to equivalent functions in various organisms (for example human, rodent, primate, plants, microorganisms, etc.) (for example, human PKR (Meurs, et al. Cell 62:379-390, 1990) and murine PKR (Feng, et al. Proc. Natl. Acad. Sci. USA 89: 5447-5451, 1992); Baier, et al. Nucleic Acids Res. 21:4830-4835, 1993). In one embodiment, PKR is a monomer. It is not intended that PKR activity is limited to one PKR molecule. In one embodiment, PKR is an alternatively spliced molecule. In one embodiment, PKR is a dimer. In one embodiment, PKR is autophosphorylated. In one embodiment, PKR activity is inhibited by ribosomal protein L18. In one embodiment, PKR activates eIF-2 kinase activity.

TLR4 and PKR are also involved in induction of macrophage apoptosis by *Y. pseudotuberculosis*, a relative of the plague bacterium, which uses its YopJ virulence factor to inhibit MAPK signaling (Orth et al. Science 290, 1594-7, 2000), and *S. typhimurium* strains deficient in the SipB virulence factor. Furthermore, PKR preactivation by synthetic dsRNA potentiates TLR4-induced macrophage apoptosis ex vivo and interferes with clearance of systemic *S. typhimurium* infection in vivo. PKR-deficient mice are resistant to this immunosuppressive effect. The ability of activated PKR to induce macrophage apoptosis is dependent on inhibition of new protein synthesis, which is necessary for induction of anti-apoptotic proteins.

Microbial-induced macrophage apoptosis is thought to represent a major mechanism that allows pathogenic bacteria to avoid detection and destruction by the innate immune system (Weinrauch et al. Annu Rev Microbiol 53, 155-87, 1999). Virulence factors used by certain pathogens to dismantle host defenses were identified and in some cases shown to act through inhibition of antiapoptotic signaling pathways (Park et al. Science 297, 2048-51, 2002; Orth et al. Science 290, 1594-7, 2000; Rosenberger and Finlay, Nature Rev. Mol. Cell. Biol. 4, 385-396, 2003). The results described above shed further light on this phenomenon and identify what appears to be a general mechanism used by three different exemplary bacterial pathogens, *B. anthracis, Yersinia* and *Salmonella*, to specifically kill activated macrophages.

The inventors demonstrate that macrophage apoptosis by either gram-positive (*B. anthracis*) or gram-negative (*Yersinia, Salmonella*) pathogens requires activation via TLR4. It is not intended that the present invention be limited to a particular "bacterium," portion of bacterium or stage of bacterium lifecycle. In one embodiment, said bacterium is chosen from one or more of infectious bacterium. As used herein, the term "infectious" refers to bacterium that are capable of at least one cell division. In another embodiment said bacterium is selected from one or more of whole, intact, inactivated, dead, lysate, fractionated, secreted molecules, endotoxins, outer cell membrane components, pili parts, cell wall parts, coat parts, glycoproteins, glycolipids, polysaccharides, M protein, external parts, membrane parts, internal parts, peptides, lipids, and nucleic acids. In one embodiment, bacterium is a gram-positive bacterium (e.g. *Bacillus anthracis* Sterne, and the like) (Welkos et al, J Med Microbiol 51, 821-31, 2002). In one embodiment, bacterium is a gram-negative bacterium (e.g. *Yersinia* species, *Salmonella typhimurium, H. influenza*, and the like). In one embodiment, bacterium is wild-type bacterium (e.g. *S. typhimurium* strains SL1344 and 14028). Further, it is not intended that the said bacterium is limited to wild-type bacterium. In one embodiment, bacterium are mutant bacterium and contain one or more inactive genes (e.g. *Yersinia pseudotuberculosis* YP26 (YopJ-), *Salmonella typhimurium* 14028 ssaV (contain mutations in genes that code for components of the SPI2 type III protein secretion system) and *Salmonella typhimurium* 14028 sipB (contain mutations in SipB), and *Salmonella typhimurium* SL1344/SipB⁻ (Browne et al, Infect Immun 70, 7126-35, 2002), etc.).

It is not intended that the present invention be limited to a particular method of bacterium culture. In one embodiment, *B. anthracis* Sterne strain (Welkos et al. J Med Microbiol 51, 821-31, 2002) was grown overnight on BHI (brain-heart infusion) agar: a single colony was inoculated into BHI broth and grown with vigorous shaking to an OD600 of 0.4. In one embodiment, heat killed *B. anthracis*, were prepared by resuspending bacterium in PBS as above and heated to 65° C. for 30 min (Welkos et al. J Med Microbiol 51, 821-31, 2002).

It is not intended that the present invention be limited to a particular method of obtaining bacterium. In one embodiment, *Y. pseudotuberculosis* strains YP126 (wt) and YP26 (YopJ-) (Zhang and Bliska, Infect Immun 71, 1513-9, 2003) were obtained from Dr. J. Bliska (SUNY at Stony Brook, N.Y.)

Curiously, however, TLR4 is not a typical death receptor with death domains that cause caspase-8 activation (Strasser et al. Annu Rev Biochem 69, 217-45, 2000). In fact, TLR4 engagement results in activation of both antiapoptotic and pro-apoptotic signaling pathways. Normally, the anti-apoptotic pathways, which seem to depend on the MyD88 and TIRAP/MAL adaptor proteins, dominate and exposure of macrophages to bacterial cell wall components, such as LPS, does not result in considerable cell death.

However, at least two of the pathogens the inventors examined (*B. anthracis* and *Y. pseudotuberculosis*) produce specific virulence factors that inhibit survival pathways (p38, IKK/NF-κβ) and thereby tilt the balance in favor of cell killing. Most importantly, the inventors identified an essential component of the TLR4-triggered macrophage apoptosis pathway, the protein kinase PKR. Based on phenotypic and biochemical similarities in the behavior of PKR- and TRIF- or TRAM-deficient macrophages (Hoebe et al. Nature 424, 743-748, 2003; Yamamoto et al. Science 301, 640-643, 2003), and the direct involvement of TRIF for PKR activation, the inventors propose that TLR4 activates PKR through the newly described adaptors TRIF, TRAM (Hoebe et al. Nature 424, 743-748, 2003; Yamamoto et al. Science 301, 640-643, 2003; Yamamoto et al. Nat Immunol 4, 1144-1150, 2003), and the like. Although PKR is an important contributor to antiviral defenses under certain circumstances (Durbin et al. Viral Immunol. 15, 41-51, 2002), its overall contribution to host defenses in the case of bacterial infections has not been explored. The results described above suggest that PKR-inhibition may strongly augment macrophage-mediated antibacterial responses that do not depend on production of type I IFN and induction of IFN-responsive genes such as iNOS.

The decreased expression of iNOS, a major inducer of vasodilation upon PKR inhibition, may also be taken advantage of for prevention of septic shock.

Figure 7:
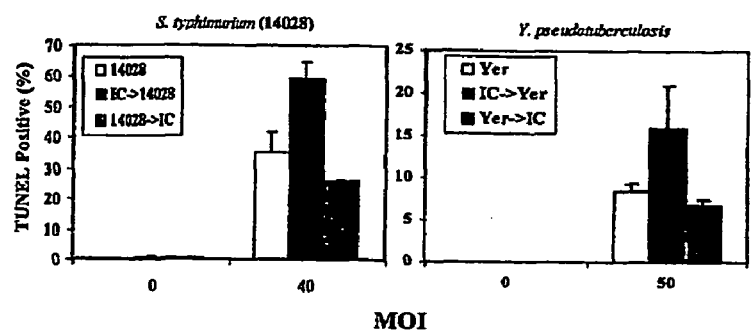
FIG. 7 shows an exemplary embodiment in which pretreatment with dsRNA potentiates pathogen-induced macrophage apoptosis and increases bacterial load in a PKR-dependent manner.
Figure 7:
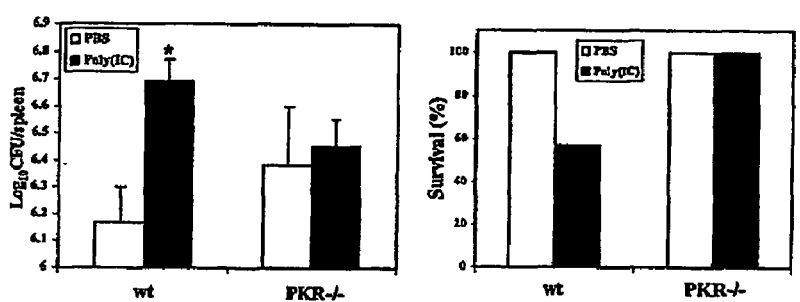
Figure 7:
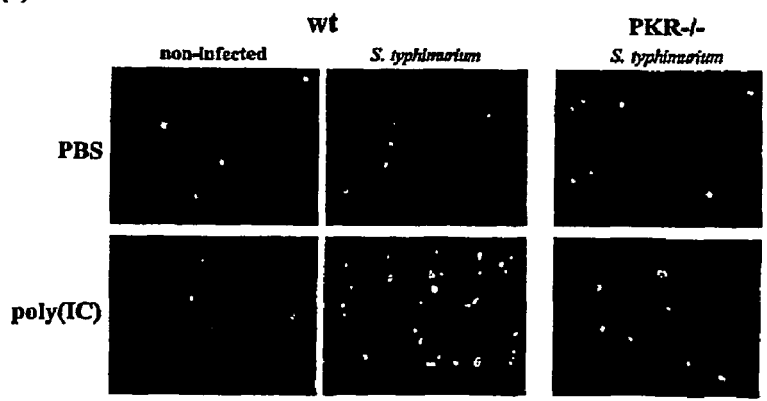
Figure 7:
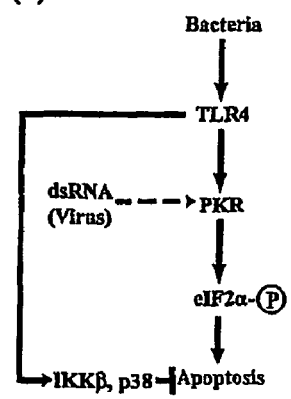

Despite being essential for macrophage apoptosis, a low level of PKR activation does not lead to cell killing. Although macrophage stimulation with exogenous poly(IC), leads to at least as much PKR activity as LPS exposure, only little macrophage apoptosis ensues. TLR4 stimulation on its own is also not sufficient for triggering the apoptotic program. However, preincubation of macrophages with poly(IC), which causes both direct (Samuel et al. Clin Microbiol Rev 14, 778-809, 2001) and TLR3-dependent (Jiang et al. J Biol Chem 278, 16713-9, 2003). PKR activation, strongly potentiates TLR4-mediated apoptosis. An even greater potentiation of the apoptotic response is seen upon poly(IC) transfection, which bypasses TLR3 activation (Diebold et al. Nature 424, 324-328, 2003). Interestingly, this potentiation was also observed when poly(IC) was introduced into mice before exposure to LPS or live bacteria. Pretreatment of mice with poly(IC) led to marked increase in bacterial load and splenocyte apoptosis after *S. typhimurium* infection (FIG. 7). Although based on a simplified system, which omits other virus produced factors, these findings are similar to those made about viral-bacterial synergy. Only when viral infection or treatment with type I IFN preceded bacterial infection, but not the other way around, excess mortality (McCullers et al. J Infect Dis 186, 341-50, 2002; Doughty et al. J Immunol 166, 2658-64, 2001) and macrophage apoptosis (Adler et al. Biochem Biophys Res Commun 215, 921-7, 1995; Lehner et al. Blood 98, 736-42, 2001) were observed.

Figure 5:
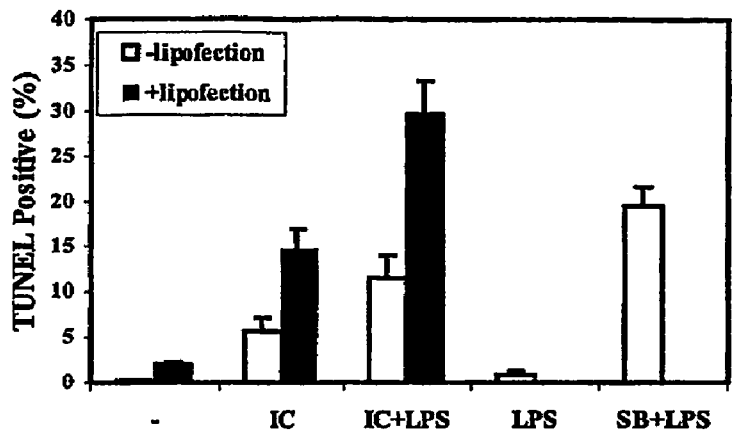
FIG. 5 shows an exemplary embodiment in which PKR induces macrophage apoptosis by inhibiting synthesis of anti-apoptotic proteins.
Figure 5:
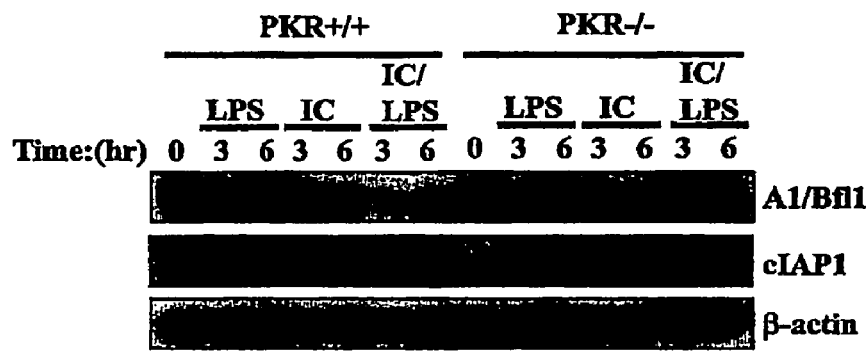
Figure 5:
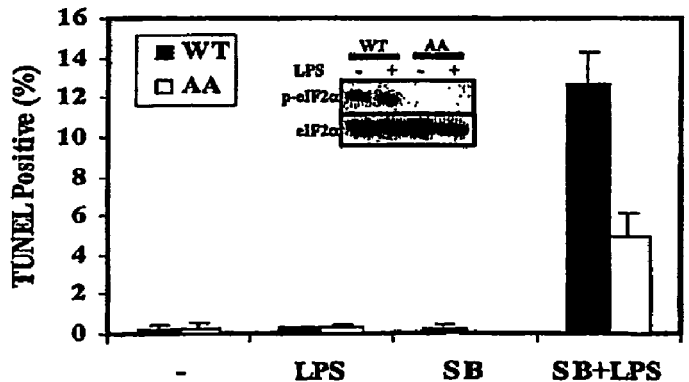
Figure 12:
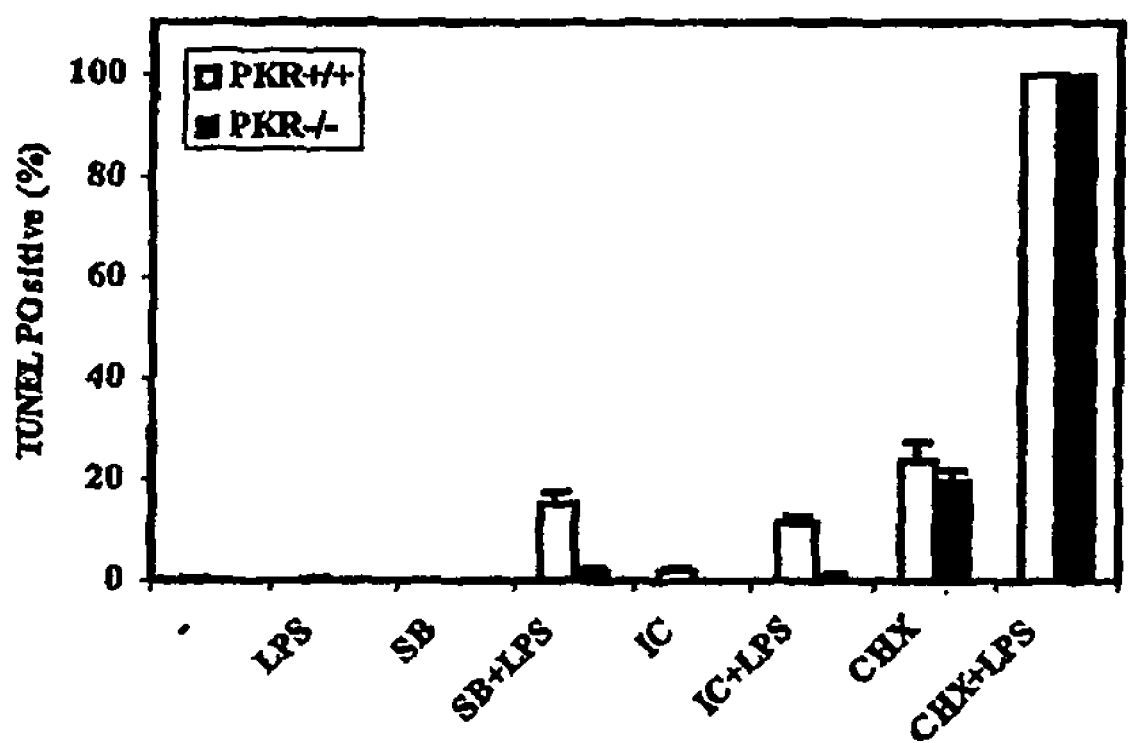
FIG. 12 shows an exemplary embodiment in which protein synthesis is involved in macrophage survival.
Figure 13:
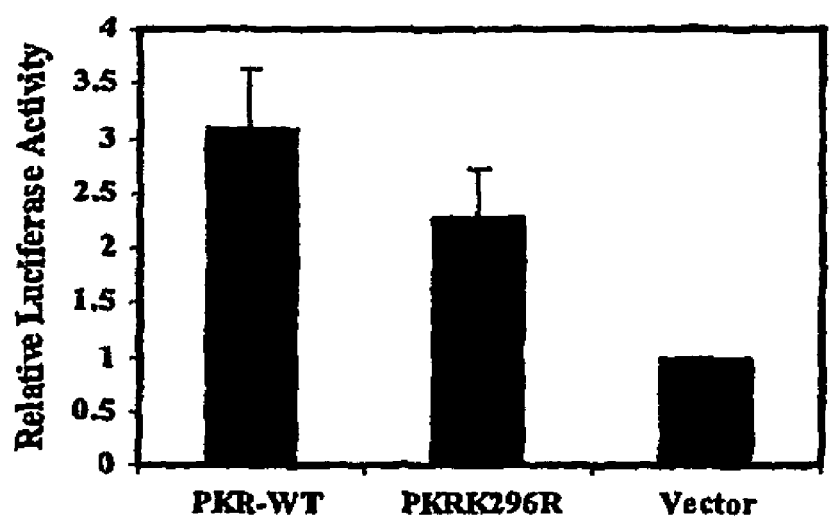
FIG. 13 shows an exemplary embodiment in which the kinase activity of PKR is involved in macrophage apoptosis induced by LPS, but not for NF-κB activation.
Figure 13:
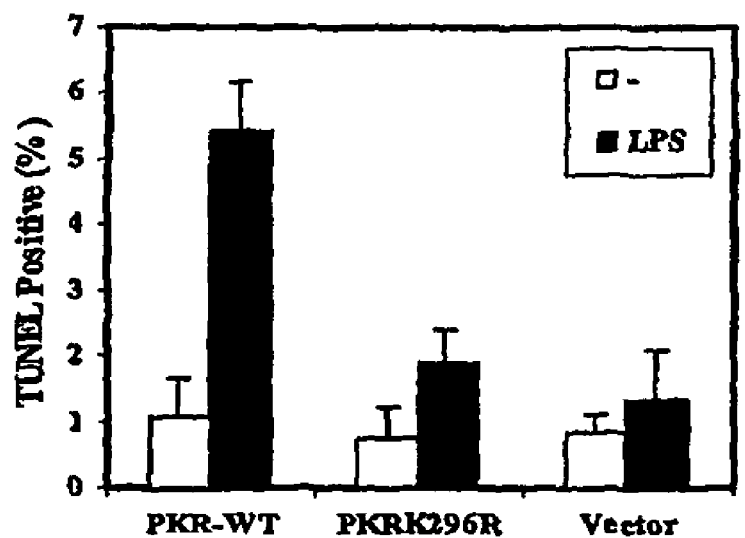

The dependence of the potentiating effect of poly(IC) on its introduction prior to LPS administration is most likely related to the mechanism of PKR-induced apoptosis. The inventors found that strong PKR activation inhibited expression of A1, key anti-apoptotic members of the Bcl2 family in myeloid cells (Hamasak et al. J Exp Med 188, 1985-1992, 1998) whose expression was strongly induced upon LPS treatment, but only modestly in response to poly(IC) exposure (FIG. 5b). Macrophages whose eIF2α is refractory to PKR phosphorylation were resistant both (Dunne et al. Sci STKE 2003, re3, 2003) to LPS- and *Salmonella*-induced apoptosis and lost inhibition of A1 expression. It is also interesting to note that transcription of the A1a gene is dependent on p38 activity (Park et al. Science 297, 2048-51, 2002) (FIG. 3d), thus suggesting why inhibition of p38 synergizes with TLR4-mediated PKR activation to induce macrophage apoptosis. PKR can also cause NF-kappaB activation, but unlike the apoptotic response (Gil et al. Apoptosis 5, 107-14, 2000) this response does not require its catalytic activity (Chu et al. Immunity 11, 721-31, 1999) (FIG. 13). It should be also noted that macrophage survival is highly dependent on ongoing protein synthesis and the mere incubation of either wt or PKR-/- BMDMs with cycloheximide triggered apoptosis (FIG. 12). Based on our results with the poly(IC)-*Salmonella* model, the inventors propose that PKR inhibition may be useful for boosting the innate immune response to both highly virulent pathogens, such as the anthrax and plague bacteria, as well as more common infections with *Streptococus* spp., *S. aureus*, and *H. influenza* that follow viral infections. Rather surprisingly, ablation of PKR expression in mice did not result in a considerable increase in susceptibility to several viruses (Yang et al. Embo J 14, 6095-106, 1995). Thus PKR-inhibition may not interfere with certain anti-viral responses, while strongly augmenting certain macrophage-mediated antibacterial responses. Given the decreased iNOS expression in PKR-/- macrophages, these anti-bacterial responses are likely to be iNOS independent. However, the decreased expression of iNOS, a major inducer of vasodilation, can be taken advantage of in the prevention of septic shock.

TLR4 can Trigger Macrophage Apoptosis

More than 10 TLRs are known, and some of the PAMPs that cause their activation were identified (Dunne et al. Sci STKE 2003, re3, 2003). The inventors found that LT or p38 inhibitors induce apoptosis in macrophages that were activated by either LPS or LTA, derived from gram-negative and gram-positive bacteria, respectively (Park et al. Science 297, 2048-51, 2002). The inventors also found that heat-inactivated *B. anthracis*, a gram-positive bacterium, can induce extensive macrophage apoptosis in the presence of SB202190, a p38 inhibitor, but bone marrow derived macrophages (BMDMs) from C3H/HeJ mice, which have an inactivating point mutation in the Tlr4 gene (Poltorak et al. Science 282, 2085-8, 1998) are resistant to such killing (FIG. 1a). To investigate which TLR is most capable of triggering macrophage apoptosis upon p38 inhibition the inventors used BMDMs from C57BL/6J mice. A strong apoptotic response dependent on p38 inhibition was detected in BMDMs treated with the TLR4 agonist, LPS (FIG. 1b). As used herein, the term "agonist" refers to a molecule that when interacting with a biologically active molecule, causes a change (e.g., signal, activation, enhancement, and the like) in the biologically active molecule, which modulates the activity of the biologically active molecule. Agonists may include proteins, nucleic acids, carbohydrates, or any other molecules which bind or interact with biologically active molecules. For example, an agonist can alter the activity of gene transcription by interacting with RNA polymerase directly of through a transcription factor. For example, a TLR4 agonist are certain form of LPS, TLR2 agonist is synthetic bacterial lipopeptide (SBLP; Pam3CSK4), a TLR9 agonist is immunostimulatory DNA, which contains non-methylated CpG dinucleotides, a TLR3 agonist, synthetic dsRNA [poly(IC)], etc. As used herein, the terms "antagonist" and "inhibitor" refer interchangeably to a molecule that, when interacting with a biologically active molecule, blocks or modulates the biological activity of the biologically active molecule. Antagonists and inhibitors may include proteins, nucleic acids, carbohydrates, or any other molecules that bind or interact with biologically active molecules. Inhibitors and antagonists can affect the biology of entire cells, organs, or organisms (e.g., an inhibitor that slows tumor growth). In one embodiment, an antagonist acts as a competitive inhibitor, or as a noncompetitive inhibitor of ligand binding. Little apoptosis in p38-inhibited macrophages was seen after incubation with the TLR2 agonist synthetic bacterial lipopeptide (SBLP; Pam3CSK4) or the TLR9 agonist immunostimulatory DNA, which contains non-methylated CpG dinucleotides (FIG. 1b). The TLR3 agonist, synthetic dsRNA [poly(IC)], induced a weak apoptotic response even without p38 inhibition. To confirm the role of TLR4 in macrophage apoptosis, a CD4-hToll chimera (Medzhitov et al. Nature 388, 394-7, 1997), in which the intracellular TIR (Toll-IL-1 Receptor) domain (Dunne et al. Sci STKE 2003, re3, 2003) of TLR4 was fused to the extracellular and transmembrane domains of CD4, was expressed in macrophage-like RAW264.7 cells. As seen with LPS, CD4-hToll expression caused apoptosis only after p38 inhibition (FIG. 1c). Consistent with the critical role of TLR4, BMDMs from C3H/HeJ mice, but not from the equivalent wild type (wt) strain, C3H/HeOuJ, were resistant to apoptosis induced by LPS plus SB202190 (FIG. 1d).

TLR4 Transduces Anti-Apoptotic Signals Via MyD88, TRAF6 and IKKβ

Figure 2:
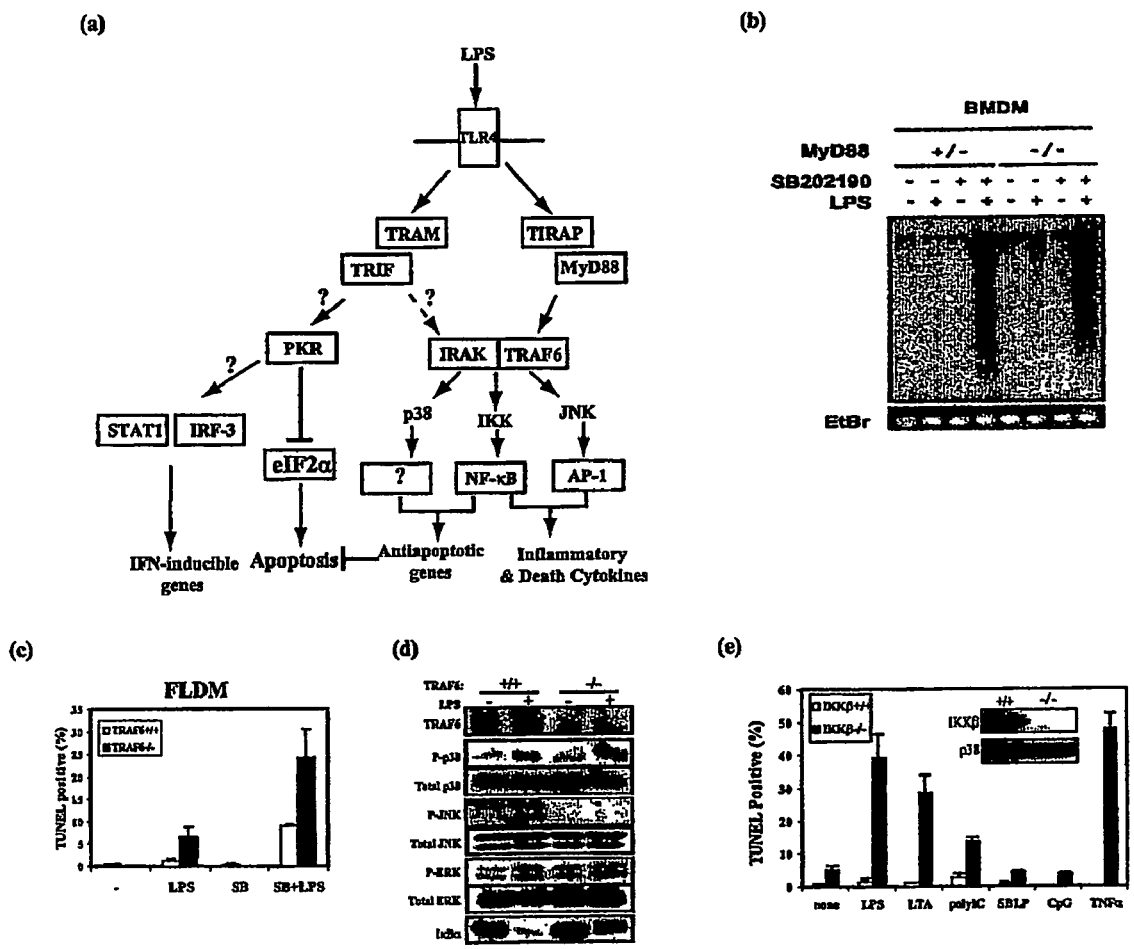
FIG. 2 shows exemplary embodiments demonstrating the role of effector molecules in TLR4-induced apoptosis.
Figure 8:
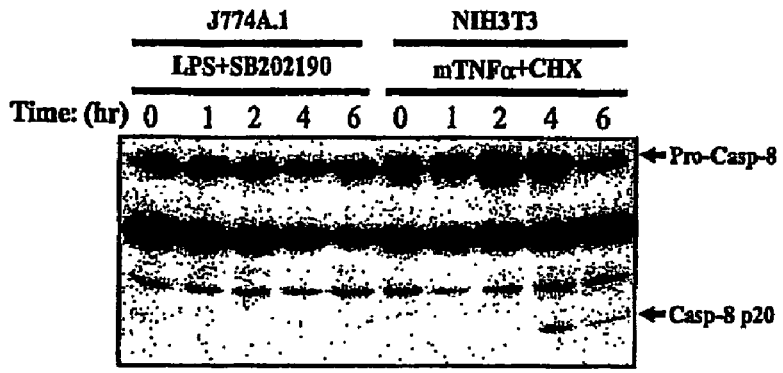
FIG. 8 shows an exemplary embodiment in which caspase activation occurs during LPS-induced macrophage apoptosis.
Figure 8:
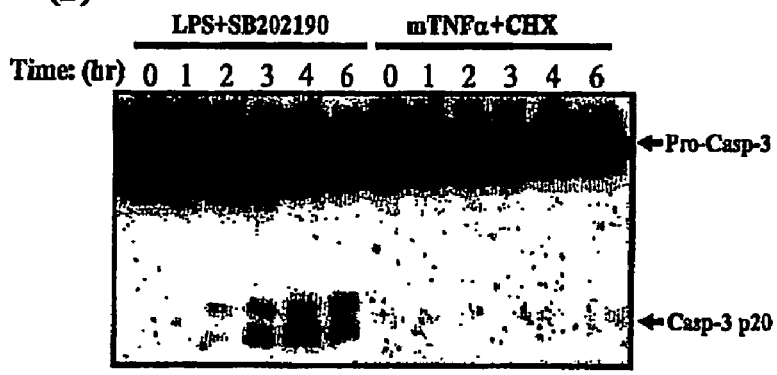
Figure 8:
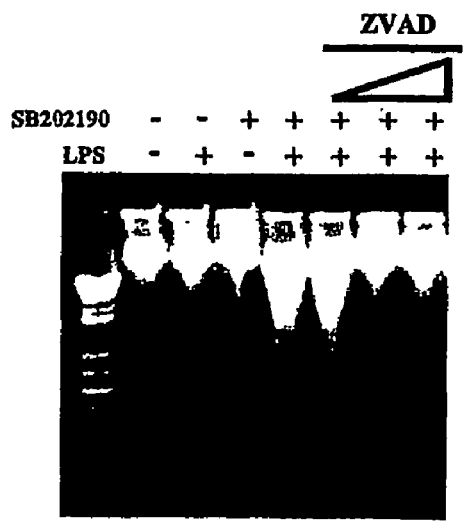

The TLR4 cytoplasmic domain uses several adaptor proteins, including MyD88, MAL/TIRAP, TRIF and TRAM to engage downstream signaling proteins and eventually activate IkappaB kinase (IKK) and MAPKs (Dunne et al. Sci STKE 2003, re3, 2003; Hoebe et al. Nature 424, 743-748, 2003; Yamamoto et al. Science 301, 640-643, 2003; Yamamoto et al. Nat Immunol 4, 1144-1150, 2003) (FIG. 2a). To determine the role of some of these effectors in macrophage apoptosis the inventors used different mutant mouse strains. Macrophages from mice deficient in MyD88 (Kawai et al. Immunity 11, 115-22, 1999) or TRAF6, a signaling protein that acts downstream of MyD88 (Naito et al. Genes Cells 4, 353-62, 1999) and TIRAP (Dunne et al. Sci STKE 2003, re3, 2003), still undergo apoptosis after LPS stimulation and p38 MAPK inhibition (FIGS. 2b, 2c). In fact, both MyD88−/− and TRAF6−/− macrophages exhibit an elevated apoptotic response. NF-κβ activation or I κβ degradation, which depend on (Karin et al. Nat Immunol 3, 221-27, 2002) are reduced in both MyD88−/−(Kawai et al. Immunity 11, 115-22, 1999) and TRAF6−/− macrophages (FIG. 2d). As NF-kappaB activates anti-apoptotic genes (Karin et al. Nat Immunol 3, 221-7, 2002), these defects may explain the enhanced apoptosis of MyD88−/− and TRAF6−/− macrophages. To examine this point, the inventors generated IKKα-deficient macrophages by crossing Iκκβ F/F mice (Li et al. J Immunol 170, 4630-4637, 2003) with mice expressing Cre recombinase from the IFN-inducible MX1 promoter (Kuhn et al. Science 269, 1427-9, 1995). IKKβ was absent in BMDMs of Iκκβ F/F MX1-Cre mice treated with poly(IC) (to induce IFN and consequently Cre expression) (FIG. 2e). IKKβ-deficient macrophages were defective in NF-kappaB activation and underwent apoptosis upon incubation with LPS, LTA, or TNF-α, even without p38 inhibition (FIG. 2e). IKKβ-deficient macrophages were also more susceptible to poly(IC) induced apoptosis. Deletion of IKKβ in macrophages did not affect p38 expression (FIG. 2e) or activation. Although TLR4 activation results in TNF-α production, the apoptosis observed in TLR4-activated and p38-inhibited macrophages is not TNF-α mediated, as it was not prevented by ablating type I TNF-α receptor (unpublished results). Furthermore, unlike apoptosis induced by TNF-α, caspase-8 was not activated during LPS-induced macrophage apoptosis (FIG. 8a). Yet, cleavage of caspases 3, 6, 7, and 9 and cytochrome c release were readily observed (FIG. 8b), and apoptosis was inhibited by a pan-caspase inhibitor (FIG. 8c). Hence, inhibition of p38 or IKKβ unleashes the ability of TLR4 to deliver a cell death signal through the mitochondrial-dependent pathway (Strasser et al. Annu Rev Biochem 69, 217-45, 2000).

PKR is Directly Involved in TLR4-Triggered Macrophage Apoptosis

Figure 3:
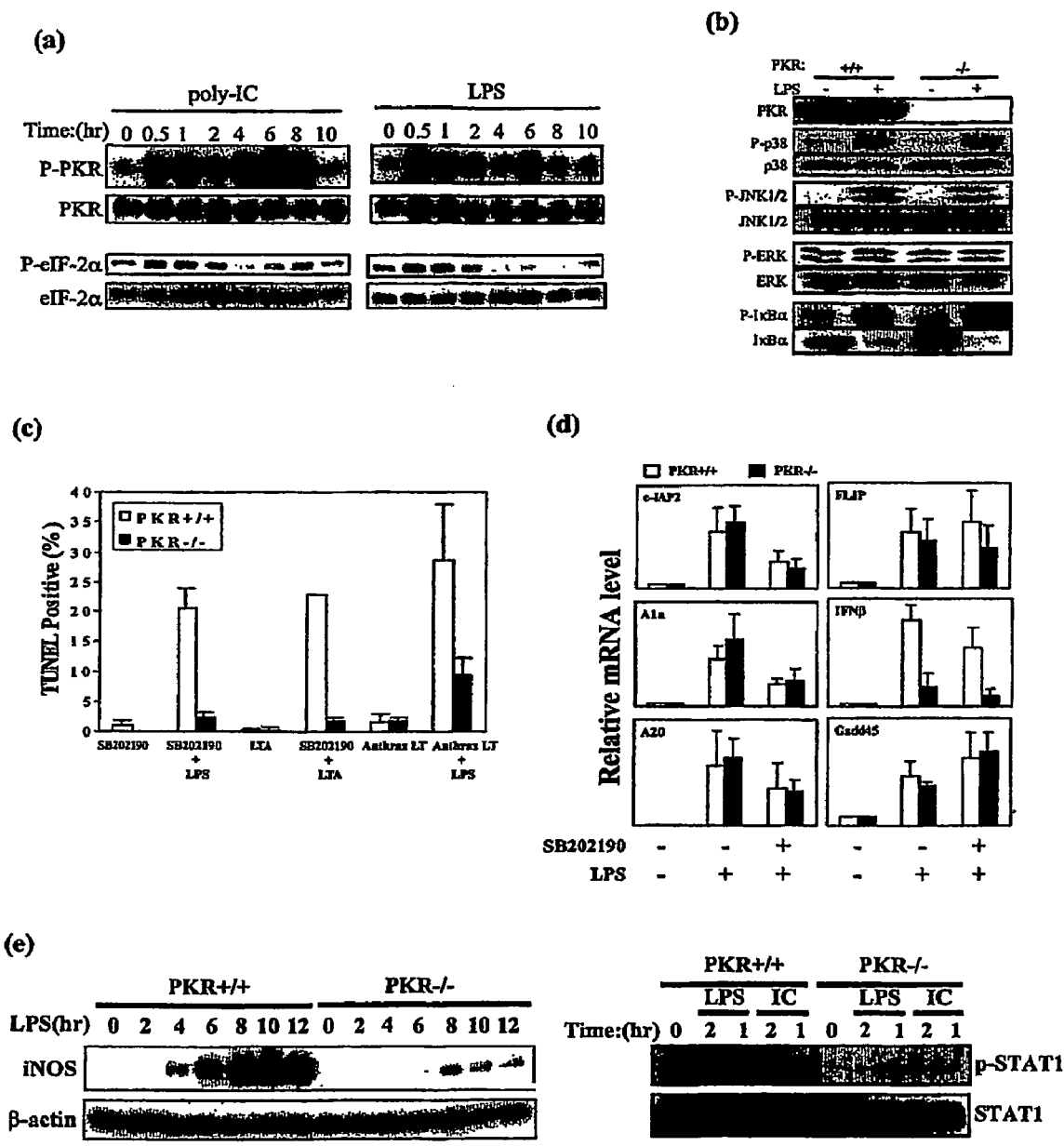
FIG. 3 shows an exemplary embodiment in which PKR is directly involved in LPS-induced macrophage apoptosis and activation of the interferon-signaling pathway.
Figure 9:
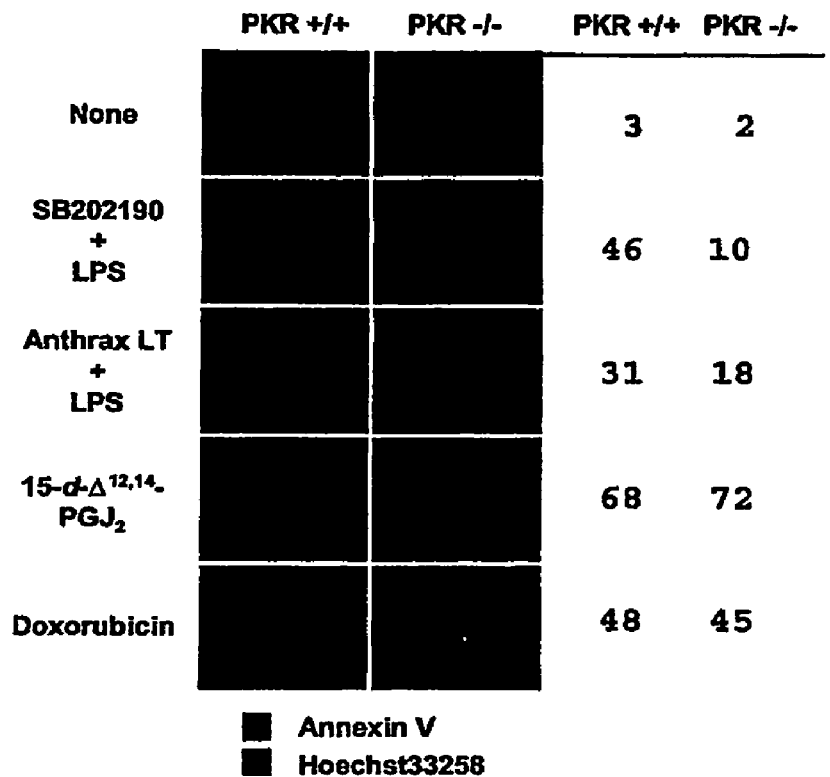
FIG. 9 shows an exemplary embodiment in which PKR is directly involved in LPS induced apoptosis.
Figure 9:
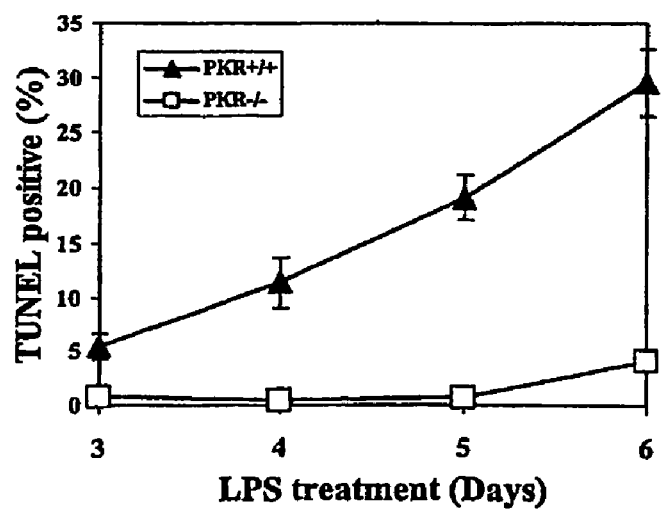
Figure 10:
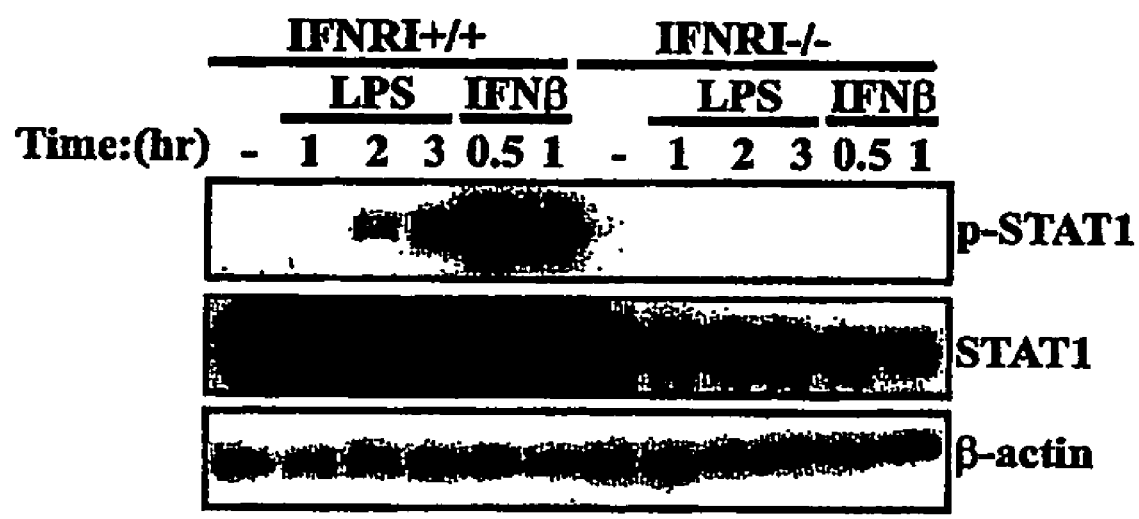
FIG. 10 shows an exemplary embodiment in which LPS-induced STAT1 phosphorylation depends on autocrine IFN signaling.

Another protein involved in TLR signaling is the dsRNA responsive kinase PKR (Dunne et al. Sci STKE 2003, re3, 2003). PKR was suggested to mediate apoptosis in fibroblasts in response to viral infection, inflammatory cytokines, and UV light (Gil et al. Apoptosis 5, 107-14, 2000; Der et al. Proc Natl Acad Sci USA 94, 3279-83, 1997). However, PKR also activates IKK and NF-kappaB (Chu et al. Immunity 11, 721-31, 1999) and thereby suppresses apoptosis. To determine the role of PKR in macrophage apoptosis, the inventors used BMDMs from PKR−/− mice (Yang et al. Embo J 14, 6095-106, 1995). In wt macrophages, PKR was rapidly activated after stimulation by either LPS or poly(IC), as demonstrated both by its autophosphorylation and phosphorylation of its substrate, eukaryotic translation initiation factor 2α (eIF2α) (FIG. 3a). Ablation of PKR did not affect p38 MAPK or IKK activation in response to LPS (FIG. 3b), but it strongly inhibited the induction of apoptosis by LPS or LTA in combination with either the p38 inhibitor or anthrax LT (FIG. 3c). The resistance of PKR−/− BMDMs to apoptosis induced by TLR4 activation and p38 inhibition was not due to a general resistance to apoptosis, as these cells still underwent apoptosis after incubation with doxorubicin or 15-deoxy-12,14-prostaglandin J2 (FIG. 9a). Prolonged incubation of wt BMDMs with LPS without p38 inhibition also resulted in apoptosis, but PKR−/− cells remained apoptosis-resistant even after 6 days with LPS (FIG. 9b). With the exception of decreased IFN-β gene expression, PKR−/− BMDMs did not exhibit a significant change in induction of numerous NF-kappaB target genes, including those coding for anti-apoptotic proteins, such as c-IAP2, c-FLIP, A1a, A20, and Gadd45β (FIG. 3d). In addition to defective IFN-β gene induction, PKR−/− BMDMs exhibited defective induction of NO synthase (iNOS) and STAT1 phosphorylation in response to LPS (FIG. 3e). LPS-induced STAT1 phosphorylation is dependent on autocrine production of type I IFNs because it was not observed in macrophages deficient in type I IFN receptor (IFNRI) (FIG. 10).

Figure 4:
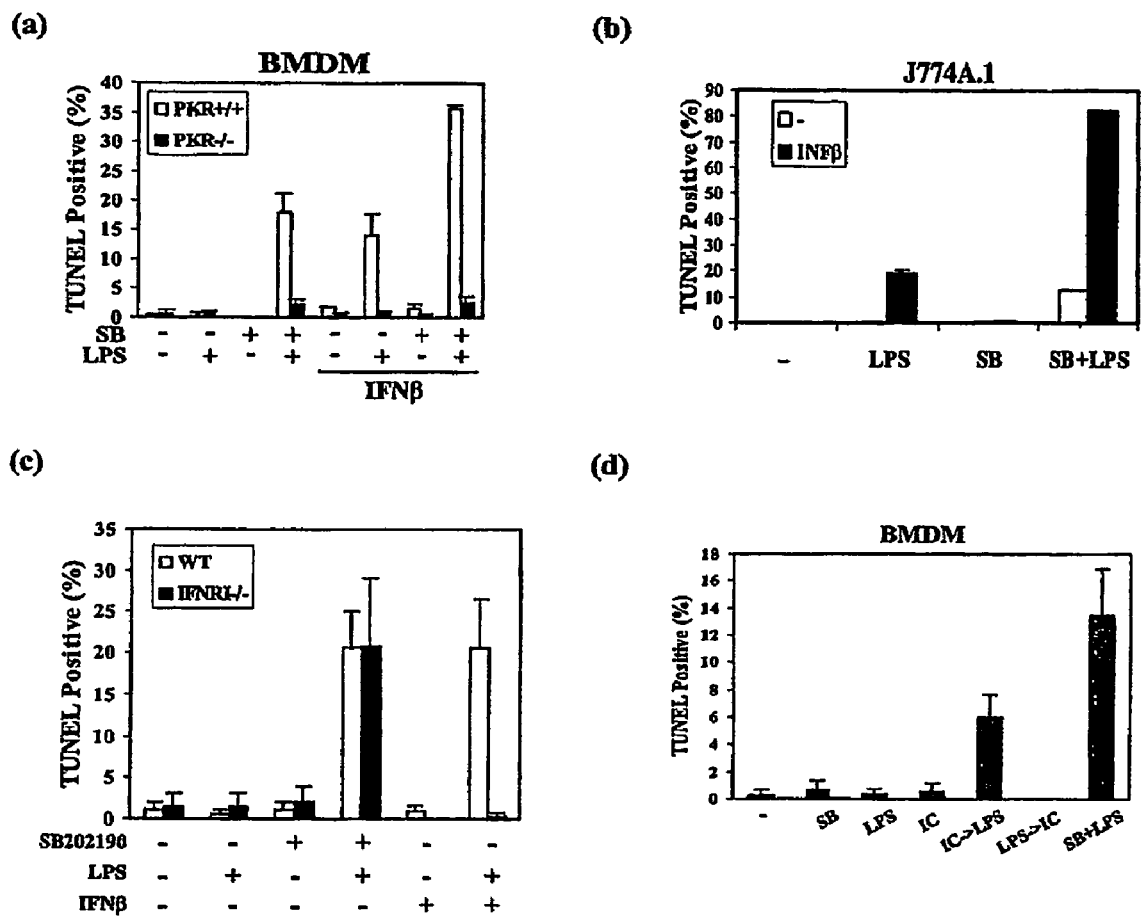
FIG. 4 shows an exemplary embodiment in which IFN-β signaling is not involved in macrophage apoptosis but can sensitize macrophages to LPS.

PKR activation potentiates macrophage apoptosis through inhibition of protein synthesis PKR activation contributes to induction of type I IFNs, such as IFN-β which can further increase its expression (Yang et al. Embo J 14, 6095-106, 1995; Samuel et al. Clin Microbiol Rev 14, 778-809, 2001). Type I IFNs sensitize myeloid cells to LPS, LTA, or bacterial-induced apoptosis (Adler et al. Biochem Biophys Res Commun 215, 921-7, 1995; Lehner et al. Blood 98, 736-42, 2001). Therefore, the inventors checked the role of type I IFNs in LPS induced macrophage apoptosis. Although IFN-β alone did not induce apoptosis in BMDMs, it rendered them susceptible to LPS-induced apoptosis even without SB202190 (FIG. 4a). IFN-β also potentiated the apoptosis of wt BMDMs (FIG. 4a) or J774A.1 macrophage-like cells (FIG. 4b) upon incubation with LPS+SB202190. But PKR−/− BMDMs were resistant to the pro-apoptotic effect of IFN-β (FIG. 4a). Nevertheless, BMDMs from IFNRI−/− mice (Muller, et al. Science 264, 1918-21, 1994) still underwent apoptosis when incubated with LPS and SB202190, and exhibited normal PKR activation by LPS (FIG. 20) but were unresponsive to IFN-β (FIG. 4c). These experiments suggest that although PKR contributes to IFN-β production, which can potentiate macrophage apoptosis, IFN-β signaling per se is not essential for TLR4-induced PKR activation or macrophage apoptosis.

PKR is activated by poly(IC), which renders BMDMs susceptible to LPS-induced apoptosis even without p38 inhibition (FIG. 4d). Interestingly, the potentiating effect of poly (IC) is seen only when macrophages are first treated with poly(IC) and then with LPS. Activated PKR phosphorylates eIF2α at serine 51 and thereby inhibits protein synthesis (Gil et al. Apoptosis 5, 107-14, 2000; Saelens et al. J Biol Chem 276, 41620-8, 2001). It is plausible that PKR activation causes macrophage apoptosis by inhibiting the synthesis of anti-apoptotic proteins. To enhance PKR activation and bypass TLR3, which may activate anti-apoptotic pathways, the inventors introduced poly(IC) into macrophages by transfection (Diebold et al. Nature 424, 324-328, 2003). This resulted in higher levels of PKR activity in comparison to simple addition of poly(IC) to the culture medium and caused a higher level of apoptosis (FIG. 5a). Transfection of wt BMDMs with poly(IC) followed by incubation with LPS inhibited the accumulation of A1/Bfl1, and to a lesser extent c-IAP1, but the same treatment of PKR−/− BMDMs did not reduce the level of either protein (FIG. 5b). A1/Bfl1 is an anti-apoptotic member of the Bcl2 family previously shown in neutrophils to be involved in inhibition of LPS-induced apoptosis (Hamasak et al. J Exp Med 188, 1985-1992, 1998). To examine the role of eIF2α phosphorylation in macrophage apoptosis, the inventors transplanted fetal liver hematopoietic progenitors from homozygote eIF2α (S51A) knockin mice, which die shortly after birth, to lethally irradiated wt mice to obtain macrophages that express a variant form of eIF2α in which serine 51, the major PKR phosphorylation site, was replaced with an alanine (Scheuner, et al. Mol. Cell. 7, 1165-1176, 2001). As shown in FIG. 5c, eIF2α (A/A) BMDMs are considerably less sensitive than wt BMDMs to apoptosis caused by incubation with LPS and SB202190 (FIGS. 16 and 18). As used herein, the term "knockin" refers to replacement or mutation of nucleotide(s) of a gene in a mouse or other laboratory animal or any cells within an animal, that when including the germ cells, creates a line of animals that can produce gene product with mutation.

PKR is Directly Involved in Pathogen-Induced Apoptosis

Figure 19:
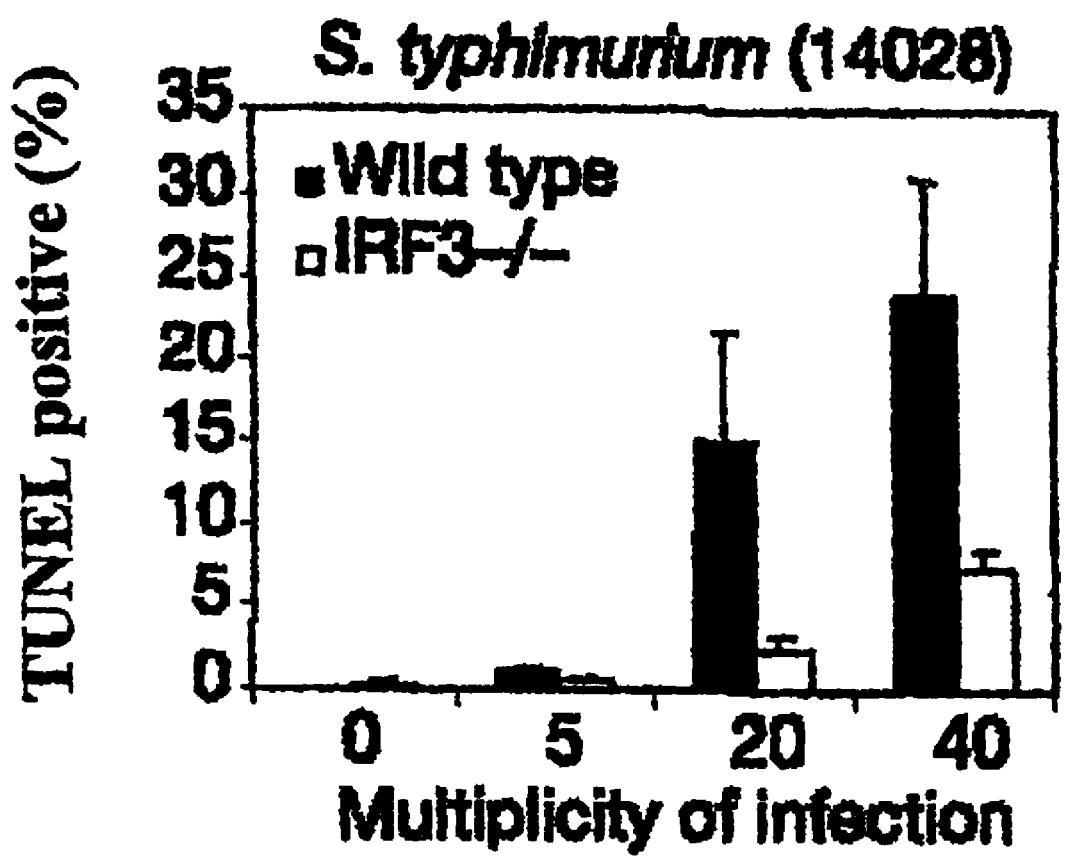
FIG. 19 shows an exemplary embodiment in which the PKR-deficient macrophages are resistant to *S. typhimurium*-induced apoptosis.

The role of TLR4 and PKR in apoptosis induced by live pathogenic bacteria was investigated using BMDMs infected with *B. anthracis, Yersinia,* and *Salmonella*. Macrophages derived from PKR−/− mice showed markedly reduced levels of apoptosis compared to wt PKR+/+ cells after infection with each of these pathogens (FIG. 6a, b). The result with live anthrax bacilli was similar to the one obtained with LT regarding the PKR dependence of apoptosis, but did not require addition of LPS (compare FIG. 6a to FIG. 3c). Pathogens that induce macrophage apoptosis activate TLR4 through cell wall components, but apoptosis also requires a specific contribution from the bacteria. *Yersinia* spp., including the plague bacillus, *Y. pestis*, induce apoptosis by injecting YopJ, an inhibitor of MAPK and IKK activation (Orth et al. Science 290, 1594-7, 2000), into the host cell cytoplasm. As expected, a yopJ mutant strain of *Y. pseudotuberculosis* did not induce apoptosis in PKR+/+macrophages. For *Salmonella* infections, PKR-dependent macrophage apoptosis was found to require the SPI2 locus, which is responsible for translocation of bacterial virulence proteins from the phagosome into the macrophage cytoplasm (Rosenberger et al. Nat Rev Mol Cell Biol 4, 385-96, 2003; Paesold et al. Cell Microbiol 4, 771-81, 2002). However, the *Salmonella* SipB protein, an activator of caspase-1 (Hersh, et al. Proc Natl Acad Sci U S A 96:2396-401, 1999), was not essential for PKR-dependent apoptosis, a finding consistent with the distinct mechanism of SipB-mediated cell death that differs from classical apoptosis (Boise and Collins Trends Microbiol 9, 64-7, 2001). Consistent with the results described above, eIF2(A/A) macrophages were also less susceptible to *Salmonella*-induced apoptosis (FIGS. 6c, 18 and 19). In addition to PKR, pathogen-induced macrophage apoptosis depends on functional TLR4. BMDMs from TLR4-deficient mice (C57BL/10ScCr) exhibited a dramatically reduced apoptotic response after infection with *B. anthracis* (FIG. 11) and as shown in FIG. 1a, the Tlr4 mutation in the C3H/HeJ strain prevented macrophage apoptosis by heat-killed *B. anthracis*. The apoptotic response to *Salmonella* and *Yersinia* was also considerably reduced in BMDMs from C3H/HeJ mice (FIG. 6d). Thus, the TLR4 to PKR pathway is crucial for macrophage apoptosis elicited by both gram-positive and gram-negative pathogens.

dsRNA potentiates pathogen-induced macrophage apoptosis and increases bacterial load Viral infections predispose humans or mice to severe morbidity and mortality from bacterial pathogens (McCullers et al. J Infect Dis 186, 341-50, 2002; Doughty et al. J Immunol 166, 2658-64, 2001). Viral infections can lead to PKR activation through production of dsRNA and type I IFN production was suggested to be involved in virus-bacteria synergy (Lehner et al. Blood 98,736-42, 2001; Doughty et al. J Immunol 166, 2658-64, 2001). Preincubation of BMDMs with the synthetic dsRNA, poly(IC), potentiated apoptosis not only in response to LPS (FIG. 4d) but also in response to infection with live *S. typhimurium* or *Y. pseudotuberculosis* (FIG. 7a). Again, the order of treatment was of importance and the cells needed to be incubated with poly(IC) first. Curiously, viral-bacterial synergy also depends on order of exposure: only viral preinfection increases morbidity in response to bacterial infection (McCullers et al. J Infect Dis 186, 341-50, 2002). To extend these studies to an in vivo model, the inventors injected mice with either 200-300 µg of poly(IC) or PBS prior to systemic infection with *S. typhimurium* and examined the number of bacteria in their spleens 24 hrs later. Poly(IC) pretreatment resulted in large increase (3.5-fold) in the number of live bacteria recovered from the spleen (FIG. 7b). Poly(IC) pretreatment also increased the number of apoptotic cells in the red pulp of the spleens, where macrophages reside, from *S. typhimurium* infected wt mice (FIG. 7c) and increased the mortality caused by *S. typhimurium* infection (FIG. 7b). When the same experiments were repeated in PKR−/− mice, little enhancement of bacterial load, apoptosis or mortality were detected. Unlike wt mice pretreated with poly(IC), the poly(IC)-pretreated PKR−/− mice infected with *Salmonella* exhibited few visible signs of distress.

It is not intended to convey that any of these cells, proteins, molecules and receptors have only one function. Physiological pathways are in flux, for example apoptotic pathways, and not usually isolated from each other. There are several apoptotic pathways leading towards apoptotic death that overlap with several other pathways leading towards cell survival and proliferation. For example, apoptotic pathways overlap in that one protein, such as TLR4, under some circumstances contributes to increasing apoptosis while under other circumstances TLR4 will contribute to decreasing apoptosis. The same is true for PKR. Often these counteractive results are found between different cells types. Furthermore, compensatory mechanisms and/or redundancies within apoptotic pathways often counteract and/or mask the ability of any one protein to contribute to either apoptosis or cell survival. Therefore, the present invention is unique in clearly showing the contributions of TLR4 and PKR towards decreasing microbial induced apoptosis of macrophages and the value thereof.

EXPERIMENTAL

The following examples serve to illustrate certain preferred embodiments and aspects of the present invention and are not to be construed as limiting the scope thereof. In the experimental disclosure which follows, the following abbreviations apply: M (molar); mM (millimolar); µM (micromolar); nM (nanomolar); mol (moles); mmol (millimoles); µmol (micromoles); nmol (nanomoles); gm (grams); mg (milligrams); µg (micrograms); pg (picograms); L (liters); ml (milliliters); µl (microliters); cm (centimeters); mm (millimeters); µm (micrometers); nm (nanometers); ° C. (degrees Centigrade/Celsius).

Example 1

Materials and Methods

The following is a description of exemplary materials and methods that were used in subsequent Examples.

Sources of Mice:

It is not intended to limit the source of mice. In one embodiment, mice were obtained by personal donations (for example, PKR−/− mice (Yang et al. Embo J 14, 6095-106, 1995), IFNRI−/− (A129) and wild-type mice of the same genetic background (129/SvEv)19 (Muller et al. Science 264, 1918-21 (1994) were obtained from Dr. E. Raz (UCSD); C3H/HeJ, C3H/HeOuJ and C3H/HeN mice (Poltorak et al. Science 282, 2085-8, 1998), and bone marrow from lps2 mice (Hoebe et al. Nature 424, 743-748, 2003) were obtained from Dr. B. Beutler (The Scripps Research Institute, La Jolla, Calif.); TRAF6+/− mice (Naito et al. Genes Cells 4, 353-62, 1999), MyD88+/− (Kawai et al. Immunity 11, 115-22 (1999) and IRF3−/− mice were received from Drs. J. Inoue (U. Tokyo, Japan), S. Akira (Osaka U, Japan), and T. Taniguchi, respectively. In one embodiment, mice were obtained from commercial sources (for example, C57BL/6J and C57BL/10ScCr (TLR4−/−) mice were purchased from the Jackson Laboratory, etc.). In one embodiment, mice were obtained by breeding mice (for example, IKKβ knockouts were produced by crossing IκκB F/F mice, harboring a floxed IκκB allele (Li et al. J Immunol 170, 4630-7 (2003) with MX1-Cre mice (Kuhn et al. Science 269, 1427-9, 1995) (Jackson Laboratory, Bar Harbor, Me.). As used herein, the term "transgenic" when used in reference to a tissue or to a plant refers to a tissue or plant, respectively, which comprises one or more cells that contain a transgene, or whose genome has been altered by the introduction of a transgene. Transgenic cells, tissues and plants may be produced by several methods including the introduction of a "transgene" comprising nucleic acid (usually DNA) into a target cell or integration of the transgene into a chromosome of a target cell by way of human intervention, such as by the methods described herein. In one embodiment, knockout mice were of the C57BL/6 background, which is resistant to LT-induced necrosis. As used herein, the term "knockout" refers to a deletion or deactivation or ablation of a gene or deficient gene in a mouse or other laboratory animal or any cells in an animal. When said knockout includes the germ cells, subsequent breeding can create a line of animals that are incapable of or produce significantly less of said gene product. As used herein, the term "transgenic" when used in reference to a cell refers to a cell which contains a transgene, or whose genome has been altered by the introduction of a transgene.

Bone Marrow-Derived Macrophages (BMDM) and Infections:

Bone Marrow-Derived Macrophages were prepared and cultured as described (Park et al. Science 297, 2048-51, 2002; Chu et al. Cell 103, 909-18, 2000).

S. typhimurium BMDM infection was as described (Browne et al. Infect Immun 70, 7126-35, 2002), while Y. pseudotuberculosis infection was done as described (Zhang et al. Infect Immun 71, 1513-9, 2003) with slight modifications: BMDMs were infected with bacteria for 1 hr, and then cultured in fresh medium containing gentamicin (20 μg/ml) for another 18 hours.

Macrophage cultures were infected as indicated and incubated for 1 hr at 37° C. in 5% $CO_2$/95% air. Gentamicin was added to a final concentration of 20 μg/ml. After 20 hrs, the medium was removed and the cells were fixed with 4% paraformaldehyde in PBS.

Mouse Infections:

Mice (7-10 weeks old) were injected i.p. with either PBS or 200-300 μg poly(IC) in PBS. After 20 hrs, mice were injected i.p. with $10^6$ S. typhiumurium 14028 in PBS. Mice that were still alive were sacrificed after 24 hrs and their spleens removed. For certain experiments, tissue was homogenized in PBS+0.1% Triton X-100. To determine bacterial counts, tissue homogenates were diluted in PBS and plated on LB agar and colonies were counted after overnight incubation at 37° C.

Bacterial Strains and Macrophage Infections:

Wild-type Salmonella typhimurium strains used were SL1344 and 14028. Salmonella typhimurium 14028 ssaV and sipB contain mutations in genes that code for components of the SPI2 type III protein secretion system and SipB, respectively. In one embodiment, Y. pseudotuberculosis strains YP126 (wild type) and YP26 (YopJ2) were obtained from J. Bliska.

The B. anthracis Sterne strain was grown overnight on BHI (brain-heart infusion) agar. A single colony was inoculated into BHI broth or RPMI medium plus 10% fetal calf serum (FCS) (endotoxinfree) in disposable tubes and grown with vigorous shaking to an OD600 of 0.4. Bacteria were washed with PBS and resuspended in PBS. To prepare heat-killed B. anthracis, bacterial suspensions in PBS were heated to 65° C. for 30 minutes. A macrophage culture was infected as indicated and incubated for 1 h at 37° C. in 5% CO2/95% air. Gentamicin was added to a final concentration of 20 mgml (Diebold et al. Nature 424, 324-328, 2003). After 20 h, the medium was removed and cells were fixed with 4% paraformaldehyde in PBS.

TUNEL and DNA Assays:

TUNEL and DNA fragmentation assays were performed as described (Park et al. Science 297, 2048-51, 2002).

Real-Time PCR:

Total cellular RNA was prepared using TRIzol (Invitrogen; Carlsbad, Calif.) as recommended by the manufacturer. RNA was quantitated by UV absorption and analyzed by real-time PCR (Park et al. Science 297, 2048-51, 2002). Primer sequences are available upon request. All values were normalized to the level of cyclophilin mRNA expression.

Analysis of Cell Signaling:

Whole cell extracts were prepared and PKR activity was measured by autophosphorylation (Gusella et al. J Immunol 154, 345-54, 1995) after immunoprecipitation with anti-PKR antibody (Santa Cruz).

PKR Recovery was Assessed by Immunoblotting:

Phosphorylation of eIF2α was detected by immunoblotting with antibody against phosphorylated eIF2α (Biosource, Camarillo, Calif.). The same blot was stripped and probed with antibody against total eIF2αIKK and MAPK activation were measured as described (Park et al. Science 297, 2048-51, 2002). Phosphorylation of STAT1 (Medzhitov et al. Nature 388, 394-7 (1997) was monitored by immunoblotting with anti-phospho-STAT1 antibody (Cell Signaling, Beverly, Mass.).

Analysis of Gene Expression and Cell Signalling:

Total cellular RNA was prepared using TRIzol (Invitrogen), quantified by ultraviolet absorption and analysed by real-time polymerase chain reaction (PCR) (Park et al. Science 297, 2048-51, 2002). Primer sequences are available upon request. Values were normalized to the level of cyclophilin messenger RNA expression. Whole-cell extracts were prepared and PKR activity was measured by autophosphorylation (Saelens et al., J. Biol. Chem. 276, 41620-41628, 2001) after immunoprecipitation with anti-PKR antibody (Santa Cruz).

Example 2

Heat Killed *B. anthracis* and LPS Induce Macrophage Apoptosis Through TLR4

A. Heat Killed *B. anthracis* (HKBA) Induces Macrophage Apoptosis in a TLR4-Dependent Manner Bone marrow derived macrophages ((BMDMs)) from C3H/HeN (Tlr4 wt; □) or C3H/HeJ (Tlr4 mutant; ■) were incubated with HKBA or LPS (100 ng/ml) with or without the p38 inhibitor SB202190 (10 µM. After 18 hrs, apoptotic cell death was measured by TUNEL staining. Results in this and subsequent similar experiments were repeated several times and one representative done in triplicate is shown. Values represent averages ±S.D. (FIG. 1a)

B. TLR4 Agonists Induce Apoptosis in the Presence of a p38 Inhibitor

C57BL/6 BMDMs were treated with different TLR agonists: LPS (100 ng/ml), synthetic bacterial lipopeptide (SBLP; Pam3CSK4; 1 µg/ml), synthetic CpG-containing DNA (1 µM), or poly(IC) (10 µg/ml), with (■) or without (□) SB202190 (10 µM). After 18 hrs, apoptotic cell death was measured as above. (FIG. 1b)

C. The TLR4 Cytoplasmic Domain Transduces an Apoptotic Signal

RAW264.7 cells were transfected with a vector encoding a CD4-hTLR4 fusion protein, or an empty vector (pcDNA3). After 24 hrs, transfectants were incubated with or without SB202190, genomic DNA was isolated after 18 hrs and analyzed by agarose gel electrophoresis and ethidium bromide (EtBr) staining for a nucleosomal ladder indicative of apoptosis. (FIG. 1c)

D. TLR4 is Directly Involved in Induction of Apoptosis

Bone marrow derived macrophages from C3H/HeJ or C3H/HeOuJ mice were incubated with or without LPS in the presence or absence of SB202190 for 18 hrs and analyzed by DAPI (blue; to detect nuclear DNA) and TUNEL (green) staining for presence of apoptotic cells. The percentage of TUNEL-positive cells is shown on the right. (FIG. 1d)

Example 3

Role of Effector Molecules in TLR4-Induced Apoptosis

A. A Diagram of a TLR4-Stimulated Signaling Pathways in Macrophages

Question marks denote connections that have not been fully established. (FIG. 2a)

B. Role of MyD88

Bone marrow derived macrophages from MyD88+/– and MyD88–/– mice were incubated with or without LPS in the presence or absence of SB202190. After 18 hrs, genomic DNA was isolated and end-labeled with [α-P32]-dATP and Taq polymerase, followed by agarose gel electrophoresis and autoradiography. Gel loading was examined by EtBr staining. (FIG. 2b) The macrophage genotype was confirmed by PCR analysis.

C. Role of TRAF6

Embryonic day (E) 14.5 fetal liver-derived macrophages (FLDMs) from TRAF6+/+(□) and TRAF6–/–(■) mice were incubated for 18 hrs with or without LPS in the presence or absence of SB202190, and apoptotic cell death was quantitated by TUNEL staining. (FIG. 2c)

D. Characterization of LPS Signaling

TRAF6+/+ and TRAF6–/– FLDMs were untreated or treated with LPS. After 20 min, cell lysates were prepared and analyzed by immunoblotting with antibodies specific to TRAF6, IkappaBα, different MAPKs and their phosphorylated forms. (FIG. 2d)

E. Role of IKKβ

Bone marrow derived macrophages from Ikkβ F/F (IKKβ+/+) or MX1Cre-Ikkβ F/F (IKKβ–/–) mice were untreated or treated with LPS (100 ng/ml), LTA from *B. subtilis* (10 µg/ml), poly(IC) (10 µg/ml), SBLP (Pam3CSK4, 1 µg/ml), CpG-containing DNA (1 µM), and mouse TNF-α (10 ng/ml). After 12 hrs, apoptotic cell death was quantitated by TUNEL staining. Inset, macrophage lysates were analyzed by immunoblotting with antibodies specific to IKKβ and p38. (FIG. 2e)

Example 4

PKR is Directly Involved in LPS-Induced Macrophage Apoptosis and Activation of the Interferon Signaling Pathway Ablation of PKR did not affect p38 or IKK activation in response to LPS (FIG. 3b) and with the exception of decreased IFN-β (FIG. 3d) or inducible NO synthase (iNOS; FIG. 3e) expression, PKR–/– BMDMs did not exhibit reduced induction of numerous NF-κβ target genes, including those coding for anti-apoptotic proteins, such as c-IAP2, c-FLIP, A1a, A20, and Gadd45β (FIG. 3d).

A. Activation of PKR by LPS

Bone marrow derived macrophages (BMDMs) (wt) were stimulated with LPS (100 ng/ml) or poly(IC) (10 µg/ml) or left unstimulated. At the indicated time points cells were lysed and PKR activation was monitored by autophosphorylation. Gel loading was controlled by immunoblotting for PKR. The same lysates were monitored for eIF-2α phosphorylation by immunoblotting with antibodies specific for phosphorylated eIF-2a (P-eIF-2α) and total eIF-2α (FIG. 3a)

B. Normal MAPK and IKK Activation in PKR–/– Macrophages

PKR+/+ and PKR–/– BMDMs were left unstimulated or stimulated with LPS. After 20 min, cell lysates were prepared and immunoblotted with antibodies specific to different MAPKs or Ikappaβα and their phosphorylated forms. (FIG. 3b)

C. PKR-Deficient BMDMs are Resistant to Apoptosis Induced by Bacterial Products

PKR+/+(□) and PKR–/–(■) BMDMs were left unstimulated or stimulated with either LPS or LTA in the presence or absence of either SB202190 or LT (500 ng/ml LF and 2.5 µg/ml PA), and the extent of apoptosis was determined after 18 hrs by TUNEL staining. (FIG. 3c)

D. PKR is Involved in IFN-β Induction but is Dispensable for Induction of Anti-Apoptotic Genes PKR+/+(□) and PKR-/- (■) BMDMs were incubated with or without LPS (100 ng/ml) in the absence or presence of SB202190 (10 µM) After 4 hrs, total cellular RNA was isolated, and relative gene expression was determined by real-time PCR. The results shown are averages of three separate experiments normalized to the level of cyclophilin mRNA. (FIG. 3d)

E. PKR is Involved in iNOS Induction and STAT1 Phosphorylation

PKR+/+ and PKR-/- BMDMs were incubated with LPS or poly(IC) At the indicated time points, cell lysates were prepared and iNOS expression and STAT1 phosphorylation were examined by immunoblotting. (FIG. 3e)

Example 5

IFN-β Signaling is not is Involved in Macrophage Apoptosis but can Sensitize Macrophages to LPS A. IFN-β Sensitizes Bone Marrow Derived Macrophages (BMDMs) to LPS-Induced Apoptosis PKR+/+ and PKR-/- BMDMs were incubated with or without LPS in the absence or presence of SB202190 or IFN-β (1000 U/ml) for 18 hrs. The extent of apoptosis was determined by TUNEL staining. (FIG. 4a)

B. Macrophage-like J774A.1 cells were incubated with or without LPS in the presence or absence of SB202190 and IFN-β for 18 hrs and apoptosis was quantitated as above. (FIG. 4b)

C. Type I IFN Signaling is not Involved in LPS+SB202190-Induced Macrophage Apoptosis Bone marrow derived macrophages from IFNR1+/+(□) or IFNR1-/-(■) mice were incubated with or without LPS in the presence or absence of SB202190 and IFNβ for 18 hrs. The extent of apoptosis was determined as above. (FIG. 4c)

D. Bone marrow derived macrophages from PKR+/+ mice were pre-treated with either poly(IC) or LPS for 6 hrs or with SB202190 for 2 hrs, as indicated, and the second stimulus [LPS or poly(IC)] was added. After 18 hrs, apoptosis was quantitated as above. (FIG. 4d)

Example 6

PKR Induces Macrophage Apoptosis

A. PKR Induces Macrophage Apoptosis by Inhibiting Synthesis of Anti-Apoptotic Proteins PKR+/+ BMDMs were preincubated with poly(IC) in the absence or presence of lipofectamine, as indicated. LPS was added 6 hrs later and apoptosis was measured after 18 hrs. (FIG. 5a)

B. PKR Activation Inhibits A1/Bfl1 Expression

PKR+/+ and PKR-/- BMDMs were transfected with or without poly(IC) using Lipofectamine (Diebold et al. Nature 424, 324-328, 2003). After 6 hrs, LPS was added and the levels of A1/Bfl1 and cIAP-1 were examined by immunoblotting. (FIG. 5b)

C. eIF2α Phosphorylation is Required for Induction of Macrophage Apoptosis

Bone marrow derived macrophages (BMDMs) were derived from lethally irradiated mice reconstituted with fetal liver stem cells from either wt (S/S) or eIF2α (A/A) E15 mice (Scheuner et al. Mol Cell 7, 1165-1176, 2001). The macrophages were incubated with LPS with or without SB202190 and the extent of apoptosis analyzed as described above. The inset shows the absence of eIF2α phosphorylation in knockin cell macrophages. (FIG. 5c)

Example 7

PKR-Deficient Macrophages are Resistant to Pathogen-Induced Apoptosis

A. PKR+/+ and PKR-/- BMDMs were infected with *S. typhimurium* (SL1344/SipB-), *S. typhimurium* (14028), *Y. pseudotuberculosis*, or *B. anthracis* at the indicated multiplicity of infection (MOI). Apoptotic TUNNEL-positive cells were counted at 18 hrs postinfection. (FIG. 6a)

B. Representative DAPI (blue) and TUNEL (green) staining of PKR+/+ and PKR-/- BMDMs 18 hrs post-infection with the indicated pathogens. (FIG. 6b)

C. eIF2α (S/S) and eIF2α (A/A) BMDMs were infected with *S. typhimurium* (14028) as above and the extent of apoptosis was determined 18 hrs later. (FIG. 6c)

D. Bone marrow derived macrophages from C3H/HeN (Tlr4 wt) and C3H/HeJ (Tlr4 mutant) mice were infected with the indicated pathogens. After 18 hrs, the extent of apoptosis was determined as above. (FIG. 6d)

Example 8

Pretreatment with dsRNA Potentiates Pathogen-Induced Macrophage Apoptosis and Increases Bacterial Load in a PKR-Dependent Manner A. Bone Marrow Derived Macrophages (BMDMs) from wt C57BL/6J Mice were Pretreated or not with Poly(IC) for 6 hrs and then Infected with *S. typhimurium* (14028) or *Y. pseudotuberculosis*

Alternatively, BMDMs were infected with bacteria first and after 1 hr incubated with poly(IC) After 18 hrs the extent of apoptosis was determined by TUNEL assays. (FIG. 7a)

B. Mice (wt and PKR-/-) were Injected i.p. with PBS or 200-300 µg Poly(IC) in PBS After 20 hrs the mice were injected i.p. with $10^6$ *S. typhimurium* (14028) bacteria suspended in PBS. After 24 hrs, survival was monitored and mice that were still alive were sacrificed and the numbers of live bacteria within their spleens determined. * represents p=0.007. (FIG. 7b)

C. Mice were Treated as Above and Parts of their Spleens Analyzed for the Presence Of Apoptotic Cells by TUNEL Staining Photograph was taken from the splenic red pulp where macrophages reside. (FIG. 7c)

D. A proposed mechanism for bacterial induced macrophage apoptosis and its potentiation by virus derived dsRNA Bacterial infection leads to activation of TLR4 and consequently IKKβ, p38 and PKR. Whereas IKKβ and p38 are anti-apoptotic, PKR is pro-apoptotic. PKR may exert its proapoptotic activity through phosphorylation of eIF2α and subsequent inhibition of host protein synthesis. This apoptotic mechanism may be augmented by preinfection with a ds(RNA)-producing virus, which further reduces expression of antiapoptotic proteins through PKR activation. (FIG. 7d)

Example 9

Caspase Activation During LPS-Induced Macrophage Apoptosis

A. J774A.1 macrophage-like cells were incubated with LPS plus SB202190 (10 µM) whereas NIH3T3 fibroblasts were incubated with mouse TNF-α (10 ng/ml) plus cycloheximide (25 µg/ml). At the indicated time points cell lysates were prepared and analyzed by immunoblotting with antibodies specific to caspase-8. (FIG. 8a)

B. J774A.1 macrophage-like cells were incubated with LPS plus SB202190 (10 µm), whereas NIH3T3 fibroblasts were incubated with mouse TNF-α (10 ng/ml) plus cycloheximide (25 µg/ml). At the indicated time points cell lysates were prepared and analyzed by immunoblotting with antibodies specific to caspase-3. (FIG. 8b)

C. J774A.1 macrophage-like cells were incubated with or without LPS in the absence or presence of SB202190. When indicated, increasing concentrations (10, 100, and 200 µM) of a pan-caspase inhibitor (ZVAD-FMK) were added. After 18 hrs, genomic DNA was isolated and analyzed by agarose gel electrophoresis and EtBr staining for appearance of nucleosomal ladders indicative of apoptosis. (FIG. 8c)

Example 10

PKR is Involved in LPS Induced Apoptosis

A. Bone marrow derived macrophages (BMDMs) from PKR+/+ and PKR−/− mice were left untreated or treated with LPS plus SB202190 or LT (2.5 µg/ml PA+500 ng/ml LF), 15-deoxy-12,14-prostaglandin J2 (5 µM), or doxorubicin (10 µg/ml), as indicated. After 16 hrs, the cells were stained with Hoechst 33258 (blue) or annexin V-Alexa568 (red). The number of annexin V-positive cells (i.e. apoptotic cells) is shown on the right. (FIG. 9a)

B. Bone marrow derived macrophages (BMDMs) from PKR+/+ or PKR−/− mice were incubated with LPS for various time periods (in days) and analyzed by TUNEL staining to determine the extent of apoptosis. The number of annexin V-positive cells (i.e. apoptotic cells) is shown on the right. (FIG. 9b)

Example 11

LPS-Induced STAT1 Phosphorylation Depends on Autocrine IFN Signaling

PKR−/− BMDMs exhibited defective STAT1 phosphorylation in response to LPS (FIG. 3f), which depends on autocrine production of type I IFNs because it was not observed in macrophages deficient in type I IFN receptor (IFNRI). (FIG. 10)

IFNR1+/+ and IFNR1−/− bone marrow derived macrophages (BMDMs) were stimulated with LPS (100 ng/ml) or IFN-β (1000 U/ml). At the indicated time points, cell lysates were prepared and analyzed by immunoblotting with antibodies specific to β-actin, STAT1 and phosphorylated STAT1. (FIG. 10)

Example 12

B. Anthracis Induced Macrophage Apoptosis is TLR4-Dependent

Figure 11:
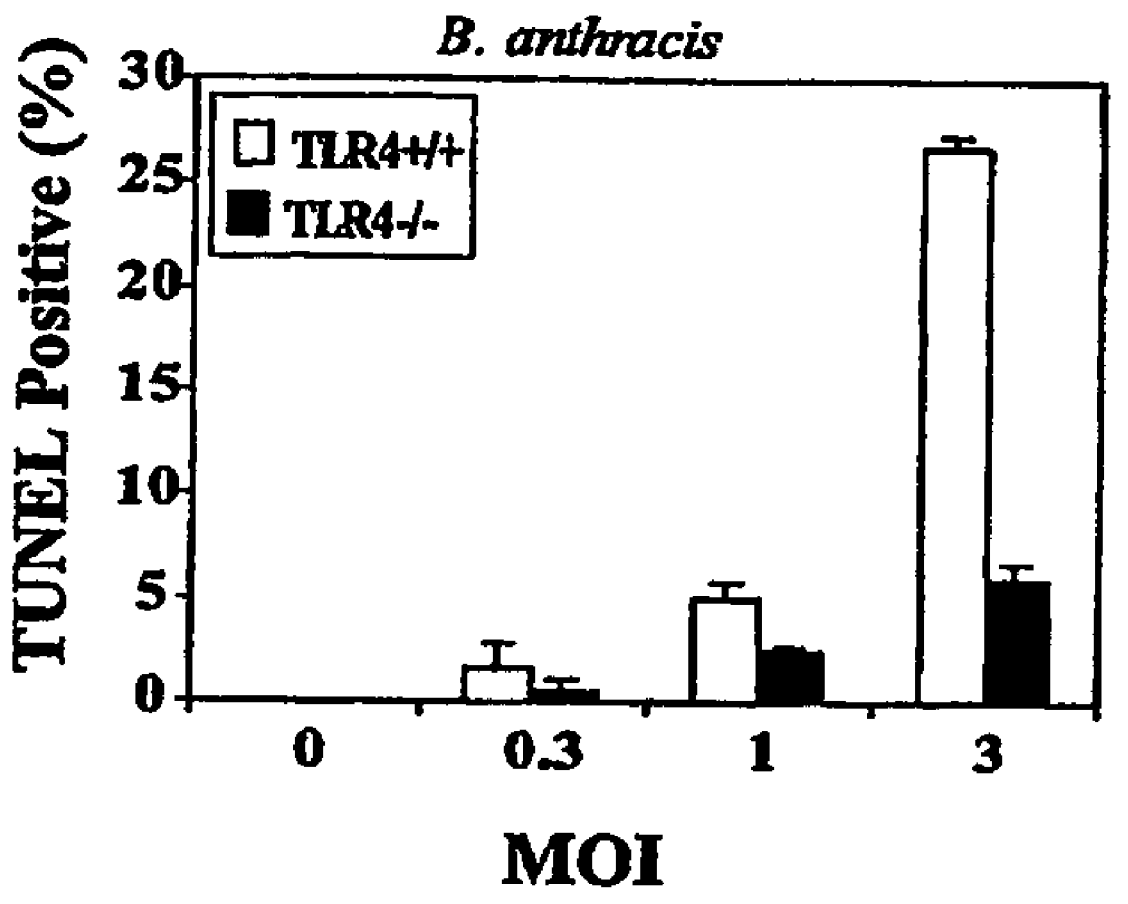

Bone marrow derived macrophages (BMDMs) from C57BL/6J (TLR4+/+), or C57BL/10ScCr (TLR4−/−) mice were infected with the indicated pathogens. After 18 hrs, the extent of apoptosis was determined by TUNEL staining. (FIG. 11)

Example 13

Protein Synthesis is Involved in Macrophage Survival

PKR+/+ and PKR−/− BMDMs were pretreated or not with poly(IC) for 6 hrs or with either SB202190 or cycloheximide (10 µg/ml) for 2 hrs, as indicated, and then LPS was added. The extent of apoptosis was determined after 18 hrs by TUNEL staining. (FIG. 12)

Example 14

The Kinase Activity of PKR is Involved in Macrophage Apoptosis Induced by LPS, but not for NF-kappaB Activation A. RAW264.7 macrophage-like cells were transfected with expression vectors encoding either wt PKR (PKR-WT), or a kinase-dead variant (PKRK296R) protein, or an empty vector (pcDNA3). A luciferase reporter containing two copies of NF-κβ binding sites and a β-galactosidase expression vector were also included. After 40-48 hrs, cell lysates were collected and luciferase activity was measured. Transfection efficiency was monitored by β-galactosidase activity. (FIG. 13a)

B. RAW264.7 cells were transfected with expression vectors encoding either wt PKR (PKRWT), or a kinase-dead version (PKRK296R), or an empty vector (pcDNA3). After 24 hrs, transfectants were incubated in the absence or presence of LPS (100 ng/ml), and after an additional 18 hrs, incubation were analyzed by TUNEL staining. (FIG. 13b)

Example 15

Role of Effector Molecules in TLR4-Induced Apoptosis

Figure 14:
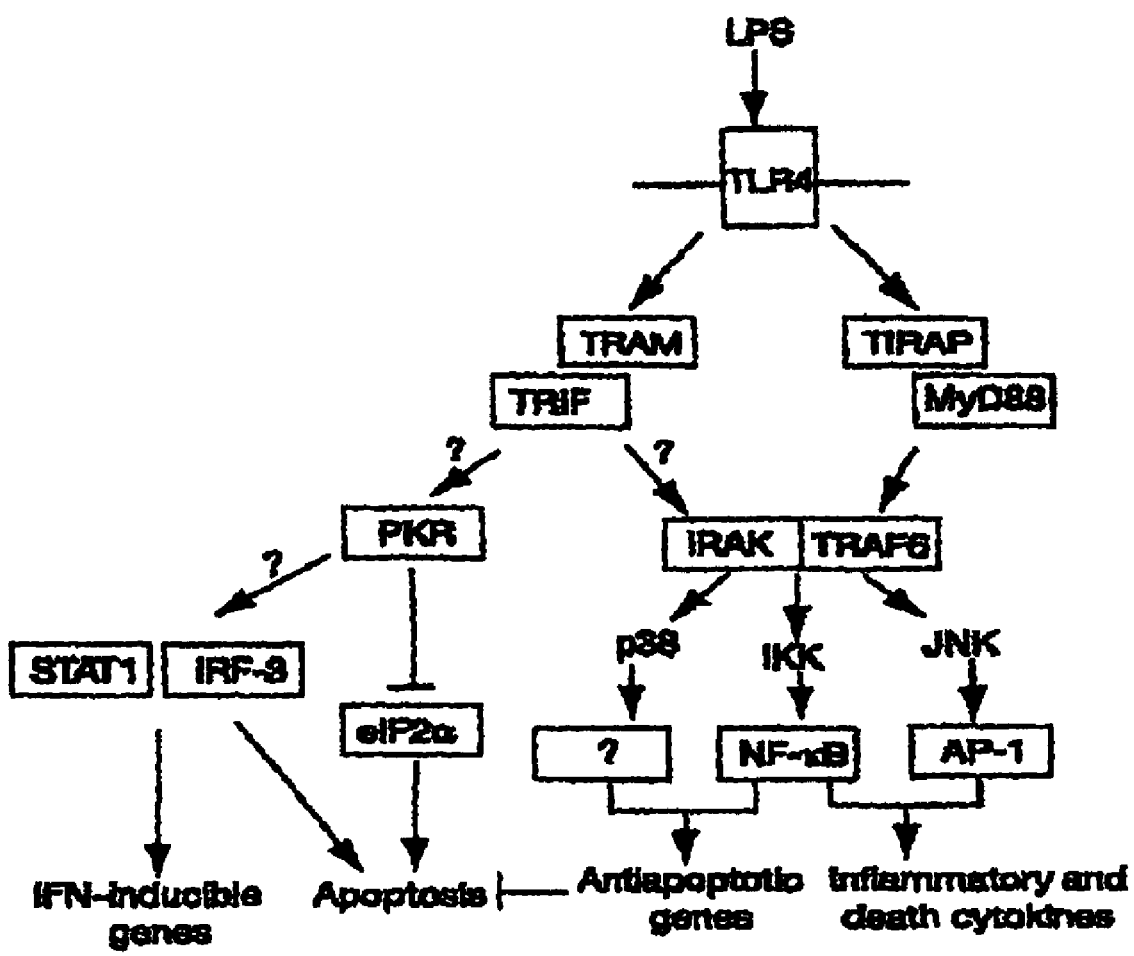
FIG. 14 shows exemplary embodiments demonstrating the role of effector molecules in TLR4-induced apoptosis; including interferon response factor 3 (IRF-3).

A diagram of a TLR4-stimulated and PKR mediated signaling pathways in macrophages; including interferon response factor 3 (IRF-3) is shown in FIG. 14. Question marks denote connections that have not been fully established.

Example 16

Protein Kinase R Acts Downstream of TRIF

Since dsRNA responsive kinase Protein Kinase R (PKR), is involved in TLR signalling (Horng, et al. Nature Immunol. 2, 835-841, 2001), PKR was suggested to mediate apoptosis in fibroblasts in response to viral infection and inflammatory cytokines (Kaufman, Proc. Natl. Acad. Sci. USA 96, 116935, 1999). However, since PKR also activates IKK and NF-κβ16 and thereby suppresses apoptosis the following experiment was performed in order to demonstrate whether PKR mediated apoptosis involved Toll-Like Receptor (TLR) signaling mediated through TRIF (TIR domain containing adaptor inducing interferon-β).

Figure 15:
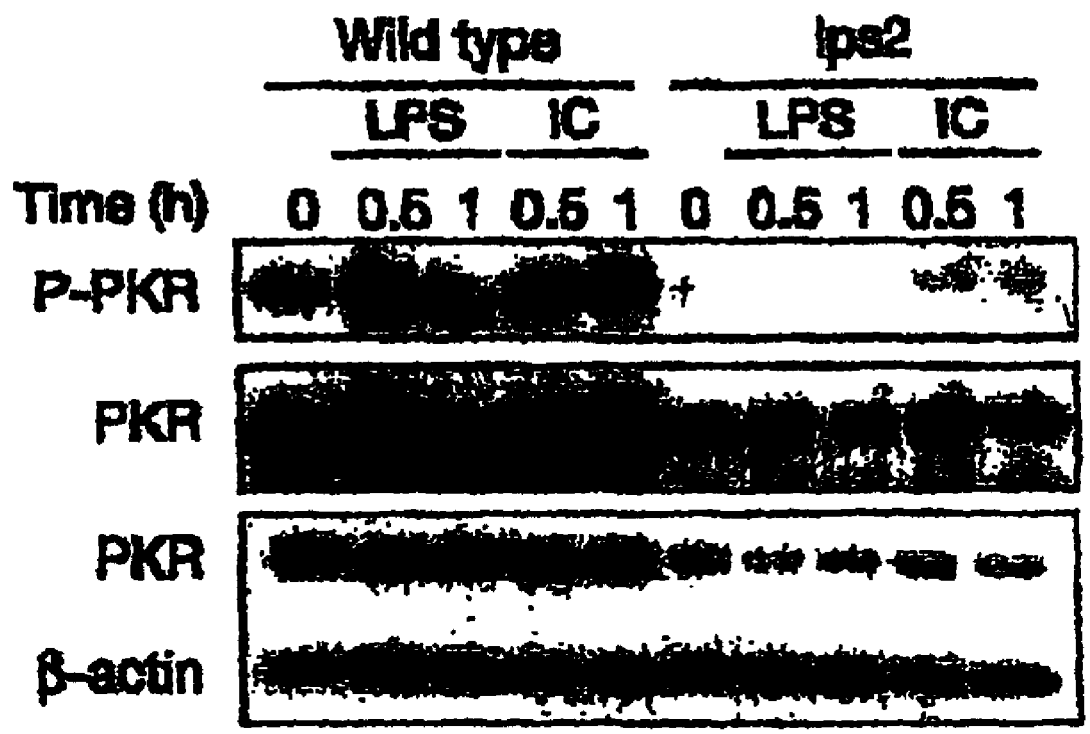
FIG. 15 shows an exemplary embodiment in which PKR acts downstream of TRIF (TIR domain containing adaptor inducing interferon-β).

Wild-type and lps2 (TRIF-deficient) bone marrow derived macrophages (BMDMs) were stimulated with LPS or poly (IC). PKR activation was monitored by autophosphorylation. The same lysates were examined for PKR and β-actin content by immunoblotting. (FIG. 15)

It is shown here that PKR rapidly activated by either LPS or poly(IC) (FIGS. 3a and 15) depended on reducing TRIF. (FIG. 15)

Example 17 eIF2α Phosphorylation is Directly Involved in Induction of Macrophage Apoptosis

To examine directly the role of eIF2α phosphorylation in macrophage apoptosis, the inventor's transplanted fetal liver haematopoietic progenitors from eIF2α (S51A) knockin mice, which die shortly after birth, to lethally irradiated wild-type mice, in order to obtain macrophages that express an eIF2α variant in which serine 51, the major PKR phosphorylation site, was replaced with an alanine (Scheuner, et al. Mol. Cell 7, 1165-1176, 2001). Bone marrow derived macrophages (BMDMs) derived from lethally irradiated mice reconstituted with fetal liver stem cells from either wild-type or eIF2α (S51A) mice (Scheuner, et al. Mol. Cell. 7, 1165-1176, 2001) were incubated with LPS with or without SB202190 and the extent of apoptosis was analyzed.

These results demonstrate that eIF2α (S51A) impaired BMDMs were considerably less sensitive than wildtype BMDMs to apoptosis caused by incubation with LPS and SB202190. (FIG. 16) The inset shows the absence of eIF2α phosphorylation in knockin macrophages. (FIG. 16)

Example 18

IRF-3 is Directly Involved in Induction of Macrophage Apoptosis

The residual apoptotic response in eIF2α (S51A) macrophages suggested the existence of another PKR-dependent pro-apoptotic pathway. It was proposed that Interferon Response Factor 3 (IRF-3), a transcription factor activated by dsRNA, is an important mediator of virus-induced apoptosis (Heylbroeck, et al., J. Virol. 74, 3781-3792, 2000). The inventor's found that BMDMs from IRF3−/− mice (Sato, et al., Immunity 13, 539-548, 2000) showed increased resistance to LPS and SB202190 (FIG. 17).

Bone marrow derived macrophages (BMDMs) from wild-type or IRF3−/− mice were incubated with or without LPS in the presence or absence of SB202190 for 18 hours and the extent of apoptosis was determined. (FIG. 17)

These results demonstrate that reducing IRF-3 BMDMs reduces macrophage apoptosis induced by LPS and SB202190. (FIG. 17)

Example 19 eIF2α-Deficient Macrophages are Resistant to Pathogen-Induced Apoptosis

Since eIF2α (S51A) impaired BMDMs were considerably less sensitive than wildtype BMDMs to apoptosis caused by incubation with LPS and SB202190, similar experiments were done using pathogen induced apoptosis.

Figure 6:
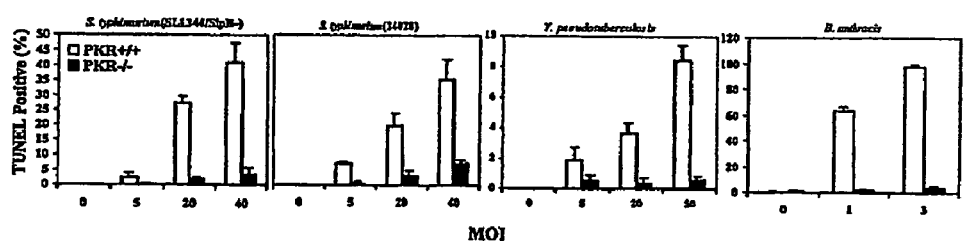
FIG. 6 shows an exemplary embodiment in which PKR-deficient macrophages are resistant to pathogen-induced apoptosis.
Figure 6:
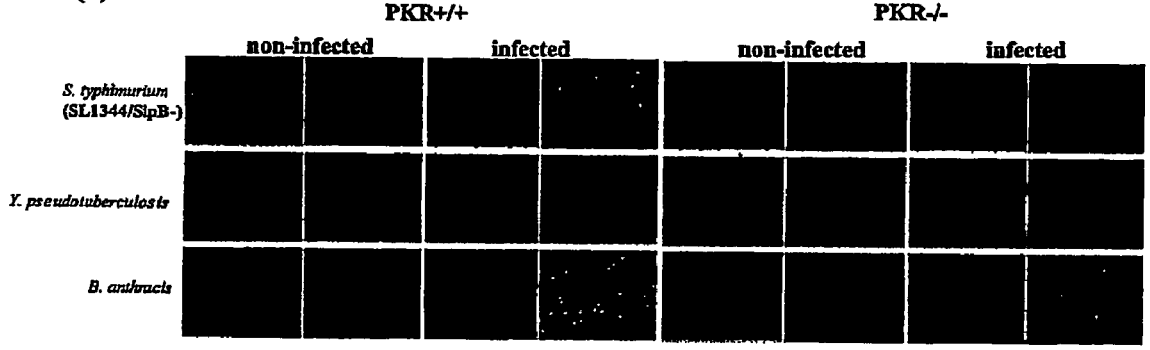
Figure 6:
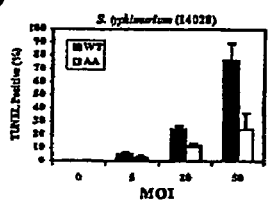
Figure 6:
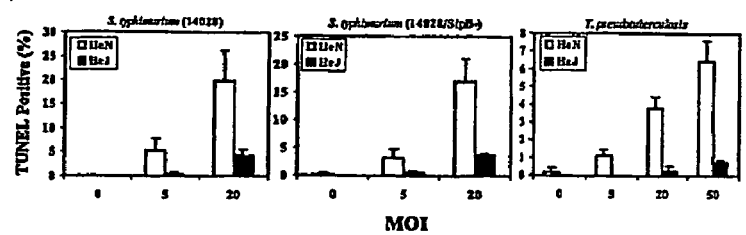

Wild-type and eIF2α (S51A) BMDMs were infected with *S. typhimurium* (14028) as in FIG. 6 and the extent of apoptosis was determined 18 hours later. (FIG. 18)

These results demonstrate that reducing eIF2α reduces macrophage apoptosis induced by a *S. typhimurium* pathogen.

Example 20

Interferon Response Factor 3 Deficient Macrophages are Resistant to *S. typhimurium*-Induced Apoptosis Since Interferon Response Factor 3 impaired BMDMs were considerably less sensitive than wild type BMDMs to apoptosis caused by incubation with LPS and SB202190, similar experiments were done using pathen induced apoptosis.

Wild-type and IRF3−/− bone marrow derived macrophages (BMDMs) were infected with *S. typhimurium* (14028) as in FIG. 6. and the extent of apoptosis was determined 18 hours later. (FIG. 19).

These results demonstrate that reducing IRF-3 reduces *S. typhimurium*-induced apoptosis.

Example 21

Type I IFN Receptor (IFNRI) does not Prevent PKR Activation Induced by LPS

Since PKR activation induces Type I IFNs such as IFN-β, and IFN-β renders myeloid cells susceptable to apoptosis induced by LPS with or without SB202190, experiments were done to see if reducing a Type I IFN R and reducing a Type I IFN R in the presence of IFN-β would impair LPS induced PKR activation.

Bone marrow derived macrophages (BMDMs) from 129/SvEv (wt) or A129 (IFNRI-1−/−) mice were stimulated with LPS (100 ng/ml) or IFN-β (1000 U/ml). At the indicated time points cells were lysed and PKR activation was monitored by autophosphorylation. Gel loading was controlled by immunoblotting for PKR.

Figure 20:
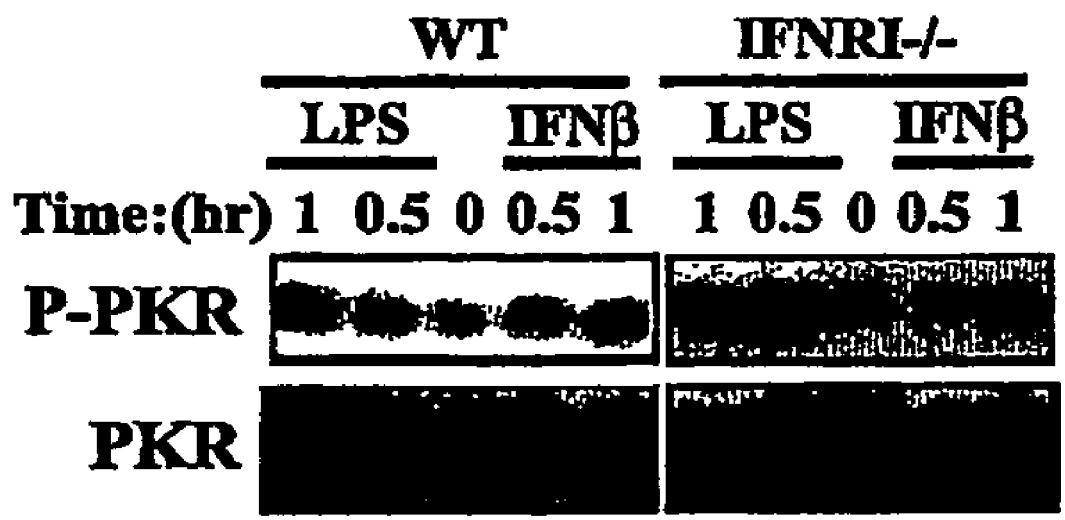
FIG. 20 shows an exemplary embodiment in which type I IFN receptor (IFNRI) is not involved in PKR activation induced by LPS.

These results demonstrate that reducing IFNRI does not prevent PKR activation. (FIG. 20)

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

The invention claimed is:

1. A method for identifying a test agent as reducing apoptosis of a macrophage cell comprising:
   (a) providing:
      (i) macrophage cells; and
      (ii) a test agent; and
   (b) contacting said macrophage cells in the presence of said test agent to produce contacted macrophage cells and in the absence of said test agent to produce control cells; and
   (c) detecting reduced activity of Protein Kinase R in said treated cells compared to Protein Kinase R in said control cells, wherein said detecting identifies said test agent as reducing apoptosis of macrophage cells.

2. A method for identifying a test agent as potentially antibacterial, comprising:
   (a) providing:
      (i) macrophage cells; and
      (ii) test agent;
   (b) contacting said macrophage cells in the presence of said test agent to produce contacted macrophage cells and in the absence of said test agent to produce control cells; and
   (c) detecting reduced activity of Protein Kinase R in said treated cells compared to Protein Kinase R in said control cells, wherein said detecting identifies said test agent as potentially anti-bacterial.

* * * * *

SEQUENCE LISTING

<160> NUMBER OF SEQ ID NOS: 4

<210> SEQ ID NO 1
<211> LENGTH: 551
<212> TYPE: PRT
<213> ORGANISM: Homo sapiens

<400> SEQUENCE: 1

```
Met Ala Gly Asp Leu Ser Ala Gly Phe Phe Met Glu Glu Leu Asn Thr
 1               5                  10                  15

Tyr Arg Gln Lys Gln Gly Val Val Leu Lys Tyr Gln Glu Leu Pro Asn
                20                  25                  30

Ser Gly Pro Pro His Asp Arg Arg Phe Thr Phe Gln Val Ile Ile Asp
            35                  40                  45

Gly Arg Glu Phe Pro Glu Gly Glu Gly Arg Ser Lys Lys Glu Ala Lys
    50                  55                  60

Asn Ala Ala Ala Lys Leu Ala Val Glu Ile Leu Asn Lys Glu Lys Lys
65                  70                  75                  80

Ala Val Ser Pro Leu Leu Leu Thr Thr Thr Asn Ser Ser Glu Gly Leu
                85                  90                  95

Ser Met Gly Asn Tyr Ile Gly Leu Ile Asn Arg Ile Ala Gln Lys Lys
            100                 105                 110

Arg Leu Thr Val Asn Tyr Glu Gln Cys Ala Ser Gly Val His Gly Pro
        115                 120                 125

Glu Gly Phe His Tyr Lys Cys Lys Met Gly Gln Lys Glu Tyr Ser Ile
    130                 135                 140

Gly Thr Gly Ser Thr Lys Gln Glu Ala Lys Gln Leu Ala Ala Lys Leu
145                 150                 155                 160

Ala Tyr Leu Gln Ile Leu Ser Glu Glu Thr Ser Val Lys Ser Asp Tyr
                165                 170                 175

Leu Ser Ser Gly Ser Phe Ala Thr Thr Cys Glu Ser Gln Ser Asn Ser
            180                 185                 190

Leu Val Thr Ser Thr Leu Ala Ser Glu Ser Ser Ser Glu Gly Asp Phe
        195                 200                 205

Ser Ala Asp Thr Ser Glu Ile Asn Ser Asn Ser Asp Ser Leu Asn Ser
    210                 215                 220

Ser Ser Leu Leu Met Asn Gly Leu Arg Asn Asn Gln Arg Lys Ala Lys
225                 230                 235                 240

Arg Ser Leu Ala Pro Arg Phe Asp Leu Pro Asp Met Lys Glu Thr Lys
                245                 250                 255

Tyr Thr Val Asp Lys Arg Phe Gly Met Asp Phe Lys Glu Ile Glu Leu
            260                 265                 270

Ile Gly Ser Gly Gly Phe Gly Gln Val Phe Lys Ala Lys His Arg Ile
        275                 280                 285

Asp Gly Lys Thr Tyr Val Ile Lys Arg Val Lys Tyr Asn Asn Glu Lys
    290                 295                 300

Ala Glu Arg Glu Val Lys Ala Leu Ala Lys Leu Asp His Val Asn Ile
305                 310                 315                 320

Val His Tyr Asn Gly Cys Trp Asp Gly Phe Asp Tyr Asp Pro Glu Thr
                325                 330                 335

Ser Asp Asp Ser Leu Glu Ser Ser Asp Tyr Asp Pro Glu Asn Ser Lys
            340                 345                 350

Asn Ser Ser Arg Ser Lys Thr Lys Cys Leu Phe Ile Gln Met Glu Phe
```

```
                355                 360                 365
Cys Asp Lys Gly Thr Leu Glu Gln Trp Ile Glu Lys Arg Gly Glu
        370                 375                 380

Lys Leu Asp Lys Val Leu Ala Leu Glu Leu Phe Glu Gln Ile Thr Lys
385                 390                 395                 400

Gly Val Asp Tyr Ile His Ser Lys Lys Leu Ile His Arg Asp Leu Lys
                405                 410                 415

Pro Ser Asn Ile Phe Leu Val Asp Thr Lys Gln Val Lys Ile Gly Asp
                420                 425                 430

Phe Gly Leu Val Thr Ser Leu Lys Asn Asp Gly Lys Arg Thr Arg Ser
            435                 440                 445

Lys Gly Thr Leu Arg Tyr Met Ser Pro Glu Gln Ile Ser Ser Gln Asp
    450                 455                 460

Tyr Gly Lys Glu Val Asp Leu Tyr Ala Leu Gly Leu Ile Leu Ala Glu
465                 470                 475                 480

Leu Leu His Val Cys Asp Thr Ala Phe Glu Thr Ser Lys Phe Phe Thr
                485                 490                 495

Asp Leu Arg Asp Gly Ile Ile Ser Asp Ile Phe Asp Lys Lys Glu Lys
            500                 505                 510

Thr Leu Leu Gln Lys Leu Leu Ser Lys Lys Pro Glu Asp Arg Pro Asn
        515                 520                 525

Thr Ser Glu Ile Leu Arg Thr Leu Thr Val Trp Lys Lys Ser Pro Glu
    530                 535                 540

Lys Asn Glu Arg His Thr Cys
545                 550

<210> SEQ ID NO 2
<211> LENGTH: 2808
<212> TYPE: DNA
<213> ORGANISM: Homo sapiens

<400> SEQUENCE: 2
gcggcggcgg cggcgcagtt tgctcatact ttgtgacttg cggtcacagt ggcattcagc    60
tccacacttg gtagaaccac aggcacgaca agcatagaaa catcctaaac aatcttcatc   120
gaggcatcga ggtccatccc aataaaaatc aggagaccct ggctatcata gaccttagtc   180
ttcgctggta tactcgctgt ctgtcaacca gcggttgact ttttttaagc cttctttttt   240
ctcttttacc agtttctgga gcaaattcag tttgccttcc tggatttgta aattgtaatg   300
acctcaaaac tttagcagtt cttccatctg actcaggttt gcttctctgg cggtcttcag   360
aatcaacatc cacacttccg tgattatctg cgtgcatttt ggacaaagct tccaaccagg   420
atacgggaag aagaaatggc tggtgatctt tcagcaggtt tcttcatgga ggaacttaat   480
acataccgtc agaagcaggg agtagtactt aaatatcaag aactgcctaa ttcaggacct   540
ccacatgata ggaggtttac atttcaagtt ataatagatg aagagaatt ccagaaggt   600 gaaggtagat caaagaagga agcaaaaaat gccgcagcca aattagctgt tgagatactt   660
aataaggaaa agaaggcagt tagtcctta ttattgacaa caacgaattc ttcagaagga   720
ttatccatgg ggaattacat aggccttatc aatagaattg cccagaagaa aagactaact   780
gtaaattatg aacagtgtgc atcgggggtg catgggccag aaggatttca ttataaatgc   840
aaaatgggac agaaagaata tagtattggt acaggttcta ctaaacagga agcaaaacaa   900
ttggccgcta aacttgcata tcttcagata ttatcagaag aaacctcagt gaaatctgac  960
tacctgtcct ctggttcttt tgctactacg tgtgagtccc aaagcaactc tttagtgacc  1020
```

-continued

```
agcacactcg cttctgaatc atcatctgaa ggtgacttct cagcagatac atcagagata   1080
aattctaaca gtgacagttt aaacagttct tcgttgctta tgaatggtct cagaaataat   1140
caaaggaagg caaaaagatc tttggcaccc agatttgacc ttcctgacat gaagaaaca    1200 aagtatactg tggacaagag gtttggcatg gattttaaag aaatagaatt aattggctca   1260
ggtggatttg gccaagtttt caaagcaaaa cacagaattg acggaaagac ttacgttatt   1320
aaacgtgtta atataataa cgagaaggcg agcgtgaag taaaagcatt ggcaaaactt     1380
gatcatgtaa atattgttca ctacaatggc tgttgggatg gatttgatta tgatcctgag   1440
accagtgatg attctcttga gagcagtgat tatgatcctg agaacagcaa aaatagttca   1500
aggtcaaaga ctaagtgcct tttcatccaa atggaattct gtgataaagg gaccttggaa   1560
caatggattg aaaaaagaag aggcgagaaa ctagacaaag ttttggcttt ggaactcttt   1620
gaacaaataa caaaggggt ggattatata cattcaaaaa aattaattca tagagatctt    1680
aagccaagta atatattctt agtagataca aaacaagtaa agattggaga ctttggactt   1740
gtaacatctc tgaaaaatga tggaaagcga acaaggagta agggaacttt gcgatacatg   1800
agcccagaac agatttcttc gcaagactat ggaaaggaag tggacctcta cgctttgggg   1860
ctaattcttg ctgaacttct tcatgtatgt gacactgctt ttgaaacatc aaagttttc    1920 acagacctac gggatggcat catctcagat atatttgata aaaagaaaa aactcttcta    1980 cagaaattac tctcaaagaa acctgaggat cgacctaaca catctgaaat actaaggacc   2040
ttgactgtgt ggaagaaaag cccagagaaa atgaacgac acacatgtta gagcccttct    2100
gaaaaagtat cctgcttctg atatgcagtt ttccttaaat tatctaaaat ctgctaggga   2160
atatcaatag atatttaccct tttatttaa tgtttccttt aatttttac tatttttact    2220 aatctttctg cagaaacaga aaggttttct tctttttgct tcaaaaacat tcttacattt   2280 tacttttttcc tggctcatct ctttattctt tttttttttt ttaaagacag agtctcgctc   2340
tgttgcccag gctggagtgc aatgacacag tcttggctca ctgcaacttc tgcctcttgg   2400
gttcaagtga ttctcctgcc tcagcctcct gagtagctgg attacaggca tgtgccaccc   2460
acccaactaa ttttttgtgtt tttaataaag acagggtttc accatgttgg ccaggctggt   2520
ctcaaactcc tgacctcaag taatccacct gcctcggcct cccaaagtgc tgggattaca   2580
gggatgagcc accgcgccca gcctcatctc tttgttctaa agatggaaaa accaccccca   2640
aattttcttt ttatactatt aatgaatcaa tcaattcata tctatttatt aaatttctac   2700
cgcttttagg ccaaaaaaat gtaagatcgt tctctgcctc acatagctta caagccagct   2760
ggagaaatat ggtactcatt aaaaaaaaaa aaaaagtgat gtacaacc                2808
```

```
<210> SEQ ID NO 3
<211> LENGTH: 515
<212> TYPE: PRT
<213> ORGANISM: Mus musculus

<400> SEQUENCE: 3

Met Ala Ser Asp Thr Pro Gly Phe Tyr Met Asp Lys Leu Asn Lys Tyr
1               5                   10                  15

Arg Gln Met His Gly Val Ala Ile Thr Tyr Lys Glu Leu Ser Thr Ser
                20                  25                  30

Gly Pro Pro His Asp Arg Arg Phe Thr Phe Gln Val Leu Ile Asp Glu
            35                  40                  45

Lys Glu Phe Pro Glu Ala Lys Gly Lys Ser Lys Gln Glu Ala Arg Asn
```

```
                50                  55                  60
Ala Ala Ala Lys Leu Ala Val Asp Ile Leu Asp Asn Glu Asn Lys Val
 65                  70                  75                  80

Asp Cys His Thr Ser Ala Ser Glu Gln Gly Leu Pro Tyr Gly Asn Tyr
                     85                  90                  95

Ile Gly Leu Val Asn Ser Phe Ala Gln Lys Lys Leu Ser Val Asn
                100                 105                 110

Tyr Glu Gln Cys Glu Pro Asn Ser Glu Leu Pro Gln Arg Phe Ile Cys
                115                 120                 125

Lys Cys Lys Ile Gly Gln Thr Met Tyr Gly Thr Gly Ser Gly Val Thr
130                 135                 140

Lys Gln Glu Ala Lys Gln Leu Ala Ala Lys Glu Ala Tyr Gln Lys Leu
145                 150                 155                 160

Leu Lys Ser Pro Pro Lys Thr Ala Gly Thr Ser Ser Val Val Thr
                165                 170                 175

Ser Thr Phe Ser Gly Phe Ser Ser Ser Ser Met Thr Ser Asn Gly
                180                 185                 190

Val Ser Gln Ser Ala Pro Gly Ser Phe Ser Ser Glu Asn Val Phe Thr
                195                 200                 205

Asn Gly Leu Gly Glu Asn Lys Arg Lys Ser Gly Val Lys Val Ser Pro
210                 215                 220

Asp Val Gln Arg Asn Lys Tyr Thr Leu Asp Ala Arg Phe Asn Ser
225                 230                 235                 240

Asp Phe Glu Asp Ile Glu Glu Ile Gly Leu Gly Gly Phe Gly Gln Val
                245                 250                 255

Phe Lys Ala Lys His Arg Ile Asp Gly Lys Arg Tyr Ala Ile Lys Arg
                260                 265                 270

Val Lys Tyr Asn Thr Glu Lys Ala Glu His Glu Val Gln Ala Leu Ala
                275                 280                 285

Glu Leu Asn His Val Asn Ile Val Gln Tyr His Ser Cys Trp Glu Gly
                290                 295                 300

Val Asp Tyr Asp Pro Glu His Ser Met Ser Asp Thr Ser Arg Tyr Lys
305                 310                 315                 320

Thr Arg Cys Leu Phe Ile Gln Met Glu Phe Cys Asp Lys Gly Thr Leu
                325                 330                 335

Glu Gln Trp Met Arg Asn Arg Asn Gln Ser Lys Val Asp Lys Ala Leu
                340                 345                 350

Ile Leu Asp Leu Tyr Glu Gln Ile Val Thr Gly Val Glu Tyr Ile His
                355                 360                 365

Ser Lys Gly Leu Ile His Arg Asp Leu Lys Pro Gly Asn Ile Phe Leu
370                 375                 380

Val Asp Glu Arg His Ile Lys Ile Gly Asp Phe Gly Leu Ala Thr Ala
385                 390                 395                 400

Leu Glu Asn Asp Gly Lys Ser Arg Thr Arg Thr Gly Thr Leu Gln
                405                 410                 415

Tyr Met Ser Pro Glu Gln Leu Phe Leu Lys His Tyr Gly Lys Glu Val
                420                 425                 430

Asp Ile Phe Ala Leu Gly Leu Ile Leu Ala Glu Leu Leu His Thr Cys
                435                 440                 445

Phe Thr Glu Ser Glu Lys Ile Lys Phe Phe Glu Ser Leu Arg Lys Gly
                450                 455                 460

Asp Phe Ser Asn Asp Ile Phe Asp Asn Lys Glu Lys Ser Leu Leu Lys
465                 470                 475                 480
```

-continued

Lys Leu Leu Ser Glu Lys Pro Lys Asp Arg Pro Glu Thr Ser Glu Ile
            485                 490                 495

Leu Lys Thr Leu Ala Glu Trp Arg Asn Ile Ser Glu Lys Lys Lys Arg
        500                 505                 510

Asn Thr Cys
        515

<210> SEQ ID NO 4
<211> LENGTH: 2380
<212> TYPE: DNA
<213> ORGANISM: Mus musculus

<400> SEQUENCE: 4

| | | | | | |
|---|---|---|---|---|---|
| accggccagg | cccggacttc | catgggcagc | agcagcggca | gggaacggag | ggcgaataga | 60 |
| tttcagagcc | tgcacctgaa | gtacaattcg | aatcctgctc | cagggagcga | gccactgtcc | 120 |
| ggatccagaa | actttggcca | ctgggaggaa | aaatggccag | tgatacccca | ggtttctaca | 180 |
| tggacaaact | taataaatac | cgccagatgc | acggagtagc | cattacgtat | aaagaactta | 240 |
| gtacttcggg | acctccacat | gacagaaggt | ttacatttca | agttttaata | gatgagaagg | 300 |
| aatttccaga | agccaaaggt | aaatcaaagc | aggaggcaag | aaacgctgca | gccaaattag | 360 |
| ctgttgatat | acttgataac | gaaaacaagg | tggattgtca | cacgagtgca | tctgagcaag | 420 |
| gcttgcccta | tggtaactac | ataggccttg | tcaatagctt | tgcccagaag | aaaaagctgt | 480 |
| ctgtaaatta | tgaacagtgt | gagcccaact | ctgagttgcc | tcaaagattt | atttgtaaat | 540 |
| gcaaaattgg | gcagacgatg | tatggtactg | gttcaggtgt | caccaaacag | gaggcaaagc | 600 |
| agttggctgc | gaaagaagcc | tatcagaagc | tgttaaagag | cccgccgaaa | actgccggaa | 660 |
| catcctctag | cgttgtcaca | tctacattca | gtggcttttc | cagcagctcg | tctatgacaa | 720 |
| gtaatggtgt | ttcccagtca | gcacctggaa | gtttttcctc | agagaacgtg | tttacgaacg | 780 |
| gtctcggaga | aaataaaagg | aaatcaggag | taaaagtatc | ccctgatgat | gtgcaaagaa | 840 |
| ataaatatac | cttggacgcc | aggtttaaca | gcgattttga | agacatagaa | gaaattggct | 900 |
| taggtggatt | tggtcaagtt | ttcaaagcga | aacacagaat | tgatggaaag | agatacgcta | 960 |
| ttaagcgcgt | taaatataac | acggagaagg | cggagcacga | agtacaagcg | ctggcagaac | 1020 |
| tcaatcacgt | caacattgtc | caataccata | gttgttggga | gggagttgac | tatgatcctg | 1080 |
| agcacagcat | gagtgataca | agtcgataca | aaacccggtg | cctctttatt | caaatggaat | 1140 |
| tctgtgataa | aggaactttg | gagcaatgga | tgagaaacag | aaatcagagt | aaagtggaca | 1200 |
| aagctttgat | tttggactta | tatgaacaaa | tcgtgaccgg | agtggagtat | atacactcga | 1260 |
| aagggttaat | tcacagagat | cttaagccag | taatatatt | tttagtagat | gaaagacaca | 1320 |
| ttaagatcgg | agactttggc | cttgcaacag | ccctggaaaa | tgatggaaaa | tcccgaacaa | 1380 |
| ggagaacagg | aactcttcaa | tatatgagtc | cagaacagtt | attttttaaag | cactatggaa | 1440 |
| aagaagtgga | catctttgct | ttgggcctta | ttctagctga | acttcttcac | acgtgcttca | 1500 |
| cggagtcaga | gaaaataaag | tttttcgaaa | gtctaagaaa | aggcgacttc | tctaatgata | 1560 |
| tattcgacaa | caaagaaaaa | agccttctaa | aaaaactact | ctcagagaaa | cccaaggacc | 1620 |
| gacctgagac | atctgaaatc | ctgaagacct | tggctgaatg | gaggaacatc | tcagagaaaa | 1680 |
| agaaaagaaa | cacatgttag | ggcctttctg | agaaaacatt | cctctgccgt | ggttttcctt | 1740 |
| taacgatctg | cagtctgagg | ggagtatcag | tgaatattat | ccttcttttc | ttaataccac | 1800 |
| tctcccagac | aggttttggt | tagggtgacc | cacagacatt | gtatttatta | ggctatgaaa | 1860 |

```
aagtatgccc atttcctcaa ttgttaattg ctgggcctgt ggctggctag ctagccaaat    1920
atgtaaatgc ttgtttctcg tctgcccaaa gagaaaggca ggctcctgtg tgggaagtca    1980
cagagccccc aaagccaact ggatgaggaa ggactctggc ttttggcata aaaaagagct    2040
ggtagtcaga gctggggcag aaggtcctgc agacagacag acagacagac agacagacag    2100
agacacaaag acatggacta gaatggagga gggagggagg aagggaggga gggagagaga    2160
gagagagaaa gaaagagaga gagaccacat ggagagacaa aatggcttaa gttagctggg    2220
ctaactgaga gactgtccca gaaaacaggc caacaacctt ccttatgcta tatagatgtc    2280
tcagtgtctt tatcattaaa caccaagcag gactgctaaa aactctgcaa tagggttttt    2340
ttttcctgtt acttcaaaag caaaaaaaaa aaaaaaaaa                           2380
```